United States Patent
Ochiai et al.

(10) Patent No.: US 9,575,408 B2
(45) Date of Patent: Feb. 21, 2017

(54) PHOTORESIST COMPOSITION AND METHOD FOR PRODUCING PHOTORESIST PATTERN

(71) Applicant: SUMITOMO CHEMICAL COMPANY, LIMITED, Tokyo (JP)

(72) Inventors: Mitsuyoshi Ochiai, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/987,303

(22) Filed: Jan. 4, 2016

(65) Prior Publication Data
US 2016/0195809 A1    Jul. 7, 2016

(30) Foreign Application Priority Data

Jan. 7, 2015 (JP) .................................. 2015-001322

(51) Int. Cl.

| | | |
|---|---|---|
| *G03F 7/004* | (2006.01) | |
| *G03F 7/38* | (2006.01) | |
| *C07C 303/32* | (2006.01) | |
| *C07C 309/04* | (2006.01) | |
| *C07C 309/06* | (2006.01) | |
| *C07C 309/12* | (2006.01) | |
| *C07C 309/17* | (2006.01) | |
| *C07C 309/19* | (2006.01) | |
| *C07C 381/12* | (2006.01) | |
| *C07D 327/02* | (2006.01) | |
| *C07D 327/04* | (2006.01) | |
| *C07D 327/06* | (2006.01) | |
| *C07D 333/46* | (2006.01) | |
| *C07D 335/02* | (2006.01) | |
| *G03F 7/038* | (2006.01) | |
| *G03F 7/16* | (2006.01) | |
| *G03F 7/20* | (2006.01) | |
| *G03F 7/32* | (2006.01) | |
| *C07C 25/18* | (2006.01) | |
| *C07D 313/10* | (2006.01) | |
| *G03F 7/039* | (2006.01) | |

(52) U.S. Cl.
CPC ............. *G03F 7/0045* (2013.01); *C07C 25/18* (2013.01); *C07C 303/32* (2013.01); *C07C 309/04* (2013.01); *C07C 309/06* (2013.01); *C07C 309/12* (2013.01); *C07C 309/17* (2013.01); *C07C 309/19* (2013.01); *C07C 381/12* (2013.01); *C07D 313/10* (2013.01); *G03F 7/0046* (2013.01); *G03F 7/038* (2013.01); *G03F 7/168* (2013.01); *G03F 7/20* (2013.01); *G03F 7/32* (2013.01); *G03F 7/38* (2013.01); *C07C 2103/74* (2013.01); *C07D 327/02* (2013.01); *C07D 327/04* (2013.01); *C07D 327/06* (2013.01); *C07D 333/46* (2013.01); *C07D 335/02* (2013.01); *G03F 7/0392* (2013.01); *G03F 7/0397* (2013.01); *G03F 7/2041* (2013.01)

(58) Field of Classification Search
CPC .... G03F 7/0045; G03F 7/0046; G03F 7/0392; G03F 7/0397; G03F 7/2041; G03F 7/38; C07C 303/32; C07C 309/04; C07C 309/06; C07C 309/12; C07C 309/17; C07C 309/19; C07C 381/12; C07D 327/02; C07D 327/04; C07D 327/06; C07D 333/46; C07D 335/02
USPC ......... 430/270.1, 326, 921, 922; 549/13, 14; 560/149, 256; 562/100, 109, 110, 113
See application file for complete search history.

(56) References Cited

U.S. PATENT DOCUMENTS

| | | | | |
|---|---|---|---|---|
| 7,449,573 B2* | 11/2008 | Kodama | ............... | G03F 7/0382 |
| | | | | 430/270.1 |
| 7,803,511 B2* | 9/2010 | Inabe | .................... | G03F 7/0045 |
| | | | | 430/270.1 |
| 7,960,087 B2* | 6/2011 | Kodama | ............... | G03F 7/0045 |
| | | | | 430/270.1 |

(Continued)

FOREIGN PATENT DOCUMENTS

| JP | 2005-227645 A | 8/2005 |
|---|---|---|
| JP | 2014-215549 A | 11/2014 |

OTHER PUBLICATIONS

Cho et al., "Environmentally Friendly Natural Materials-Based Photoacid Generators for Next-Generation Photolithography," SPIE Proceedings, vol. 7972, Advances in Resist Materials and Processing Technology XXVIII, 1 page, Apr. 15, 2011.

(Continued)

*Primary Examiner* — John S Chu
(74) *Attorney, Agent, or Firm* — Birch, Stewart, Kolasch & Birch, LLP

(57) ABSTRACT

A photoresist composition comprising
a resin having an acid-labile group;
a salt represented by the formula (I); and
a salt represented by the formula (B1).

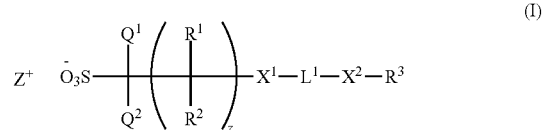

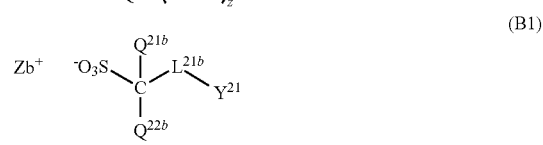

13 Claims, No Drawings

(56) References Cited

U.S. PATENT DOCUMENTS

| 8,906,589 | B2* | 12/2014 | Ichikawa | C07C 25/18 |
|---|---|---|---|---|
| | | | | 430/270.1 |
| 2010/0233617 | A1 | 9/2010 | Wada | |
| 2010/0316952 | A1 | 12/2010 | Ichikawa et al. | |
| 2013/0022917 | A1* | 1/2013 | Ichikawa | G03F 7/0045 |
| | | | | 430/281.1 |
| 2013/0022920 | A1* | 1/2013 | Ichikawa | G03F 7/0397 |
| | | | | 430/281.1 |
| 2013/0149644 | A1* | 6/2013 | Maruyama | C07C 25/18 |
| | | | | 430/270.1 |

OTHER PUBLICATIONS

Sun et al., "Biodegradability, Cytotoxicity, and Physicochemical Treatability of Two Novel Perfluorooctane Sulfonate-Free Photoacid Generators," Arch Environ Contam Toxicol, vol. 64, pp. 187-197 (13 pages), 2013 (published online Oct. 27, 2012).

Yi et al., "Sulfonium Salts of Alicyclic Group Functionalized Semifluorinated Alkyl Ether Sulfonates as Photoacid Generators," Chemistry of Materials, vol. 21, No. 17, pp. 4037-4046, 2009 (published online Aug. 14, 2009).

* cited by examiner

PHOTORESIST COMPOSITION AND METHOD FOR PRODUCING PHOTORESIST PATTERN

CROSS REFERENCE TO RELATED APPLICATIONS

This nonprofessional application claims priority under 35 U.S.C. §119(a) on Patent Application No. 2015-001322 filed in JAPAN on Jan. 7, 2015, the entire contents of which are hereby incorporated by reference.

TECHNICAL FIELD

The present invention relates to a photoresist composition and a method for producing a photoresist pattern.

BACKGROUND ART

US2010/316952A1 discloses a salt represented by the following formula:

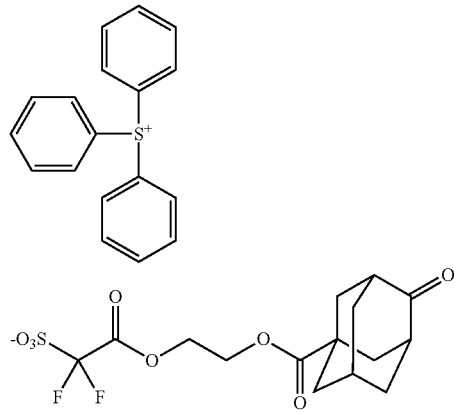

and a photoresist composition which contains the salt as an acid generator.

SUMMARY OF THE INVENTION

The invention of the disclosure relates to the followings.
[1] A photoresist composition comprising
a resin having an acid-labile group;
a salt represented by the formula (I) and
a salt represented by the formula (B1):

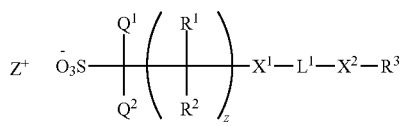

wherein $Q^1$ and $Q^2$ each independently represent a fluorine atom or a C1 to C6 perfluoroalkyl group;
$R^1$ and $R^2$ each independently represent a hydrogen atom, a fluorine atom or a C1 to C6 perfluoroalkyl group;
"z" represents an integer of 0 to 6;
$X^1$ and $X^2$ each independently represent a group having at least one of *—CO—O—, *—O—CO— and *—O— where * represents a binding site to $L^1$;
$L^1$ represents a C1 to C8 fluoroalkanediyl group; and
$R^3$ represents a C5 to C18 alicyclic hydrocarbon group in which a hydrogen atom can be replaced by a hydroxy group and a methylene group can be replaced by an oxygen atom, a sulfonyl group or a carbonyl group, and which alicyclic hydrocarbon group may have a cyclic ketal structure optionally having a fluorine atom; and
$Z^+$ represents an organic cation represented by any one of formulae (b2-1) and (b2-2):

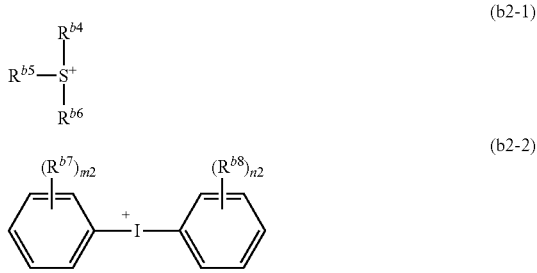

wherein $R^{b4}$, $R^{b5}$ and $R^{b6}$ independently represent a C1 to C30 aliphatic hydrocarbon group in which a hydrogen atom can be replaced by a hydroxy group, a C1 to C12 alkoxy group, a C3 to C12 alicyclic hydrocarbon group, or a C6 to C18 aromatic hydrocarbon group, a C3 to C36 alicyclic hydrocarbon group in which a hydrogen atom can be replaced by a halogen atom, a C2 to C4 acyl group or a glycidyloxy group, or
a C6 to C36 aromatic hydrocarbon group in which a hydrogen atom can be replaced by a halogen atom, a hydroxy group, or a C1 to C12 alkoxy group; or $R^{b4}$ and $R^{b5}$ each independently represent a ring together with $S^+$;
$R^{b7}$ and $R^{b8}$ each independently represent a hydroxy group, a C1 to C12 alkyl group or a C1 to C12 alkoxy group; and
m2 and n2 each independently represent an integer of 0 to 5;

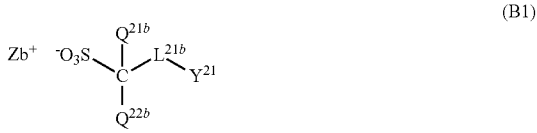

wherein $Q^{21b}$ and $Q^{22b}$ each independently represent a fluorine atom or a C1 to C6 perfluoroalkyl group,
$L^{b21}$ represents a single bond or a C1 to C24 divalent saturated hydrocarbon group where a methylene group can be replaced by an oxygen atom or a carbonyl group and where a hydrogen atom can be replaced by a hydroxy group,
$Y^{21}$ represents a C3 to C18 alicyclic hydrocarbon group where a methylene group can be replaced by an oxygen atom or a carbonyl group and where a hydrogen atom can be replaced by a hydroxyl group or a fluorine atom, and
$Zb^+$ represents an organic cation represented by any one of the formula (b2-1) and the formula (b2-2).
[2] The photoresist composition according to [1] wherein $X^1$ represents * —CO—O—.
[3] The photoresist composition according to [1] or [2] wherein $X^2$ represents * —CO—O—.
[4] The photoresist composition according to any one of [1] to [3] wherein $L^1$ represents —$CH_2$—$(CF_2)_n$—$CH_2$— where n represents integer of 1 to 6.

[5] The photoresist composition according to any one of [1] to [4] wherein the alicyclic hydrocarbon group for $R^3$ is an adamantyl group.

[6] The photoresist composition according to any one of [1] to [5] wherein $L^{b21}$ represents a group represented by formula (b1-4):

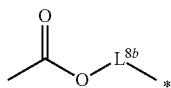

(b1-4)

wherein $L^{b8}$ represents a single bond or a C1 to C22 divalent saturated hydrocarbon group where a hydrogen atom can be replaced by a hydroxy group, and * represents a binding site to $Y^{21}$.

[7] The photoresist composition according to any one of [1] to [6], which further comprises a salt which generates an acid weaker in acidity than an acid generated from the salt represented by the formula (B1) and an acid generated from the salt represented by the formulae (I).

[8] A salt represented by the formula (Ia):

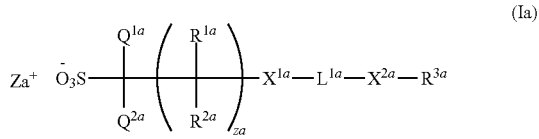

(Ia)

wherein $Q^{1a}$ and $Q^{2a}$ each independently represent a fluorine atom or a C1 to C6 perfluoroalkyl group;
$R^{1a}$ and $R^{2a}$ each independently represent a hydrogen atom, a fluorine atom or a C1 to C6 perfluoroalkyl group;
"za" represents an integer of 0 to 6;
$X^{1a}$ and $X^{2a}$ each independently represent a group having at least one of *—CO—O—, *—O—CO— and *—O— where * represents a binding site to $L^{1a}$, provided that at least one of $X^{1a}$ and $X^{2a}$ represents *—CO—O— or *—O—CO—;
$L^{1a}$ represents —$CH_2$—$(CF_2)_{na}$—$CH_2$— where "na" represents an integer of 2 to 6;
$R^{3a}$ represents a C5 to C18 alicyclic hydrocarbon group in which a hydrogen atom can be replaced by a hydroxy group, and in which a methylene group can be replaced by an oxygen atom, a sulfonyl group or a carbonyl group, and which alicyclic hydrocarbon group may have a cyclic ketal structure optionally having a fluorine atom; and
$Za^+$ represents an organic cation.

[9] The salt according to [8] wherein $X^{1a}$ represents *—CO—O—.

[10] The salt according to [8] or [9] wherein $X^{2a}$ represents *—O—CO—

[11] The salt according to any one of [8] to [10] wherein the alicyclic hydrocarbon group for $R^{3a}$ is an adamantyl group.

[12] A photoresist composition which contains the salt according to any one of [8] to [11] and a resin having an acid-labile group.

[13] A process for producing a photoresist pattern having the following steps (1) to (5):
  (1) a step of applying the photoresist composition according [1] or [12] on a substrate,
  (2) a step of forming a composition film by conducting drying,
  (3) a step of exposing the composition film to radiation,
  (4) a step of baking the exposed composition film, and
  (5) a step of developing the baked composition film.

DESCRIPTION OF PREFERRED EMBODIMENTS

Herein, the term "(meth)acrylic monomer" means a monomer having a structure of "$CH_2$=CH—CO—" or "$CH_2$=$C(CH_3)$—CO—", as well as "(meth)acrylate" and "(meth)acrylic acid" mean "an acrylate or methacrylate" and "anacrylic acidormethacrylic acid", respectively.

Herein, chain structure groups include those having a linear structure and those having a branched structure. Unless otherwise specified, the term "aliphatic hydrocarbon group" means a chain aliphatic hydrocarbon group.

The indefinite articles "a" and "an" are taken as the same meaning as "one or more".

The term "solid components" means components other than solvents in a resist composition.

One aspect of the invention is a photoresist composition containing a resin having an acid-labile group, a salt represented by the formula (I), and a salt represented by the formula (B1).

The photoresist composition may further contain a quencher, or a solvent.

The photoresist composition preferably further contains a quencher, or a solvent, more preferably both of them.

The resin having an acid-labile group is sometimes referred to as "Resin (A)". The salt represented by formula (I) is sometimes referred to as "Salt (I)". The photoresist composition is sometimes referred to as "photoresist composition (I)".

<Salt (I)>

Salt (I) is represented by formula (I):

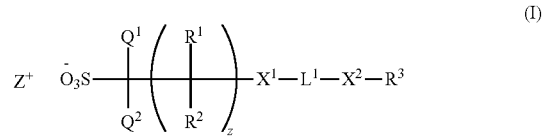

(I)

In the formula, $Q^1$ and $Q^2$ each independently represent a fluorine atom or a C1 to C6 perfluoroalkyl group;
$R^1$ and $R^2$ each independently represent a hydrogen atom, a fluorine atom or a C1 to C6 perfluoroalkyl group;
"z" represents an integer of 0 to 6;
$X^1$ and $X^2$ each independently represent a group having at least one of *—CO—O—, *—O—CO— and *—O— where * represents a binding site to $L^1$;
$L^1$ represents a C1 to C8 fluoroalkanediyl group; and
$R^3$ represents a C5 to C18 alicyclic hydrocarbon group in which a hydrogen atom can be replaced by a hydroxy group, and in which a methylene group can be replaced by an oxygen atom, a sulfonyl group or a carbonyl group, and which alicyclic hydrocarbon group may have a cyclic ketal structure optionally having a fluorine atom; and
$Z^+$ represents an organic cation represented by any one of formulae (b2-1) and (b2-2) as described later.

Examples of the perfluoroalkyl groups for $Q^1$, $Q^2$, $R^1$ and $R^2$ include a trifluoromethyl group, a perfluoroethyl group, a perfluoropropyl group, a perfluoroisopropyl group, a perfluorobutyl group, a perfluoro(sec-butyl) group, a perfluoro(tert-butyl) group, a perfluoropentyl group, a perfluorohexyl group.

$Q^1$ and $Q^2$ are each independently, preferably a trifluoromethyl group or a fluorine atom, more preferably a fluorine atom.

Preferably, $R^1$ and $R^2$ are each independently a hydrogen atom or a fluorine atom.

"z" is preferably 0 or 1, more preferably 0.

$X^1$ and $X^2$ each independently represent a group having at least one of *—CO—O—, *—O—CO— and *—O—. Here, * represents a binding site to $L^1$. The group having at least one of *—CO—O—, *—O—CO— and *—O— is generally such a group that a methylene group in a C1 to C6 alkanediyl group has been replaced, preferably at each end, by an oxygen atom and optionally by a carbonyl group.

Examples of $X^1$ include —CO—O—*, —CO—O—CH$_2$—CO—O—* and —O—CO—O—*. Among them, $X^1$ preferably represents —CO—O—* where * represents a binding site to $L^1$.

$X^2$ preferably represents *—O—CO—, *—CO—O—CH$_2$—CH$_2$—O—CO— and *—CO—O—CH$_2$—CO—O—, and more preferably *—O—CO— where * represents a binding site to $L^1$.

Examples of $L^1$ include a linear fluoroalkanediyl group such as a fluoromethylene group, a fluoroethylene group, a fluoropropane-1,3-diyl group, a fluorobutane-1,4-diyl group, a fluoropentane-1,5-diyl group, a fluorohexane-1,6-diyl group, a fluoroheptane-1,7-diyl group, and a fluorooctane-1,8-diyl group; and a branched alkanediyl group such as a fluoroethane-1,1-diyl group, a fluoropropane-1,2-diyl group, a fluorobutane-1,3-diyl group, a 2-methyl-fluoropropane-1,3-diyl group, a 2-methyl-fluoropropane-1,2-diyl group, a 2-methyl-fluoropropane-1,3-diyl group, a 2-trifluoromethylfluoropropane-1,2-diyl group, a fluoropentane-1,4-diyl group, and a 2-methylfluorobutane-1,4-diyl group. Among them, —CH$_2$—(CF$_2$)$_n$—CH$_2$—, in which "n" is preferably an integer of 1 to 6, more preferably an integer of 1 to 4, still more preferably an integer of 2 to 4 is preferred as $L^1$.

Examples of the alicyclic hydrocarbon group for $R^3$ include C5 to C10 cycloalkyl groups such as a cyclopentyl group and a cyclohexyl group, and C8 to C12 polycyclic alicyclic hydrocarbon groups such as a norbornyl group and an adamantyl group.

Among them, a cyclopentyl group, a cyclohexyl group, a norbornyl group and an adamantyl group are preferred, an adamantyl group, a norbornyl group and a cyclohexyl group are more preferred, an adamantyl group and a norbornyl group are still more preferred, and an adamantyl group is particularly preferred, as the alicyclic hydrocarbon group.

The alicyclic hydrocarbon group for $R^3$ may have a cyclic ketal structure which is represented by —O-(alkanediyl group)-O—.

The cyclic ketal structure for $R^3$ can be formed by replacing two hydrogen atoms on the alicyclic hydrocarbon group respectively by oxygen atoms which are bonded to each other via one alkanediyl group.

Examples of the alkanediyl group in the cyclic ketal structure include a linear alkanediyl group such as a methylene group, an ethylene group, a propane-1,3-diyl group, a butane-1,4-diyl group, a pentane-1,5-diyl group and a hexane-1,6-diyl group, and a branched alkanediyl group such as an ethane-1,1-diyl group, a propane-1,2-diyl group, a butane-1,3-diyl group, a 2-methylpropane-1,3-diyl group, a 2-methylpropane-1,2-diyl group, a pentane-1,4-diyl group, and a 2-methylbutane-1,4-diyl group. Examples of the cyclic ketal structure include —O—(CH$_2$)$_2$—O—, —O—(CH$_2$)$_3$—O—, —O—(CH$_2$)$_4$—O—, —O—CH$_2$—(CF$_2$)$_2$—CH$_2$—O—, —O—CH$_2$—(CF$_2$)$_3$—CH$_2$—O— and —O—CH$_2$—(CF$_2$)$_4$—CH$_2$—O—.

Among them, a cyclic ketal structure having 1 to 6 carbon atoms and a fluorine atom is preferred. Specifically, —O—CH$_2$—(CF$_2$)$_2$—CH$_2$—O—, —O—CH$_2$—(CF$_2$)$_3$—CH$_2$—O—, and —O—CH$_2$—(CF$_2$)$_4$—CH$_2$—O— are preferred, —O—CH$_2$—(CF$_2$)$_2$—CH$_2$—O—, and —O—CH$_2$—(CF$_2$)$_3$—CH$_2$—O— are more preferred, and —O—CH$_2$—(CF$_2$)$_2$—CH$_2$—O— is still more preferred.

Examples of the anions for the salt (I) include the anions represented below.

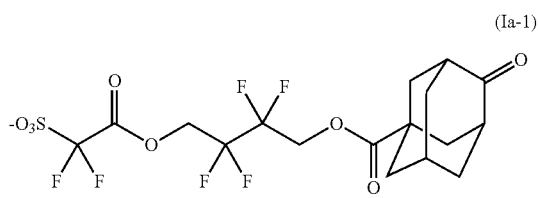

(Ia-1)

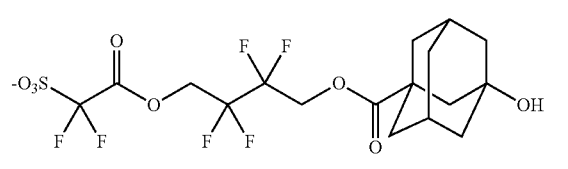

(Ia-2)

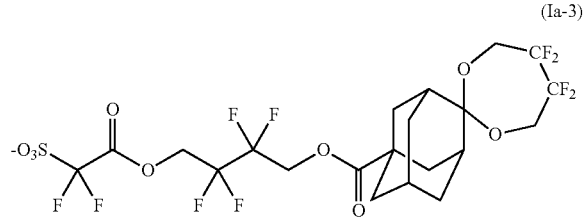

(Ia-3)

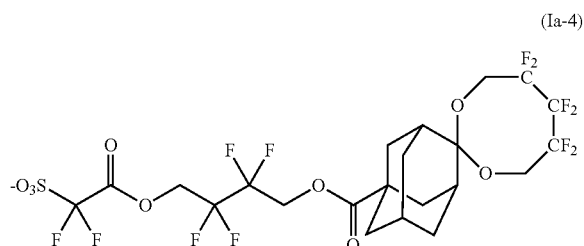

(Ia-4)

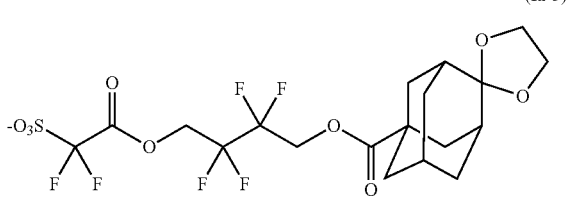

(Ia-5)

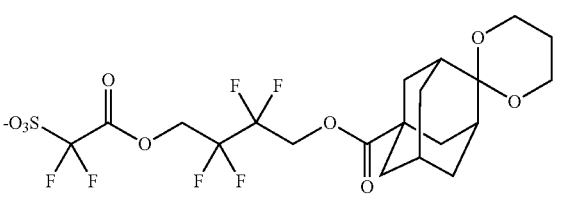

(Ia-6)

(Ia-7)
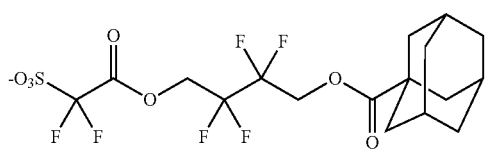

(Ia-8)
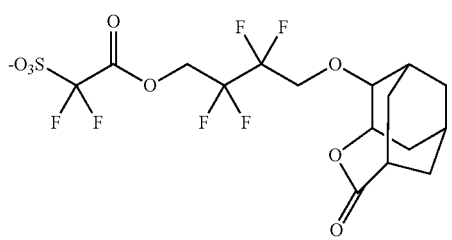

(Ia-9)
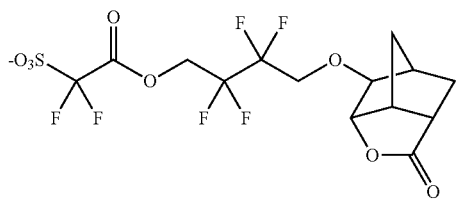

(Ia-10)
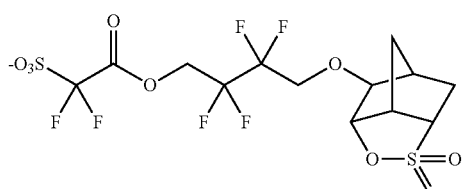

(Ia-11)
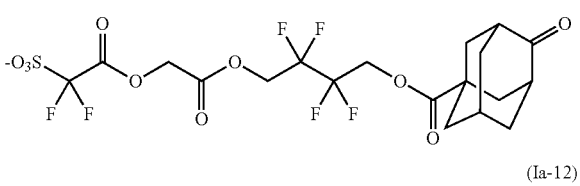

(Ia-12)
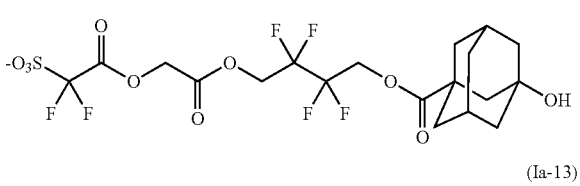

(Ia-13)
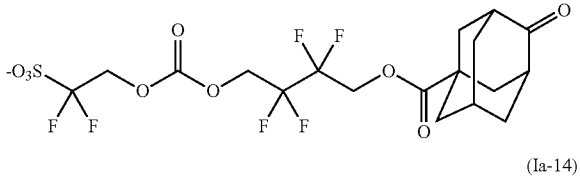

(Ia-14)
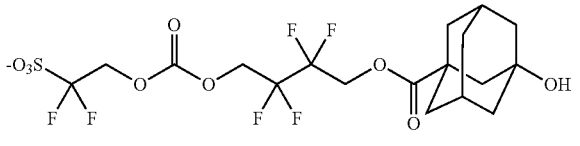

(Ia-15)
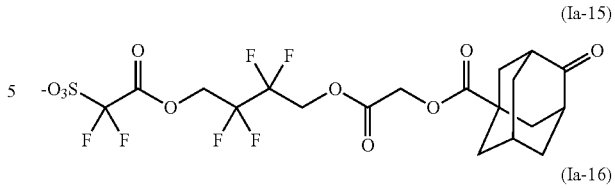

(Ia-16)
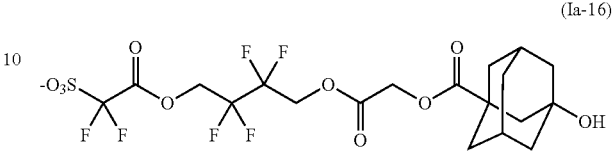

Among them, the anions represented by formulae (Ia-1) to (Ia-6) are preferred, and those represented by formulae (Ia-1) to (Ia-4) are more preferred.

In formula (I), $Z^+$ represents an organic cation represented by any one of formulae (b2-1) and (b2-2).

(b2-1)
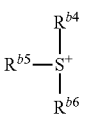

(b2-2)
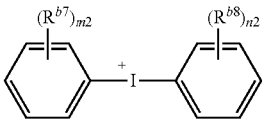

In formula (b2-1), $R^{b4}$, $R^{b5}$ and $R^{b6}$ independently represent a C1 to C30 aliphatic hydrocarbon group in which a hydrogen atom can be replaced by a hydroxy group, a C1 to C12 alkoxy group or a C3 to C12 alicyclic hydrocarbon group; a C3 to C36 alicyclic hydrocarbon group in which a hydrogen atom can be replaced by a halogen atom, a C2-C4 acyl group or a glycidyloxy group; or a C6 to 036 aromatic hydrocarbon group in which a hydrogen atom can be replaced by a halogen atom, a hydroxy group, or C1 to C12 alkoxy group; or two of $R^{b4}$, $R^{b5}$ and $R^{b6}$ can be bonded each other to form a ring containing $S^+$.

In formula (b2-2), $R^{b7}$ and $R^{b8}$ each independently represent a hydroxy group, a C1 to C12 aliphatic hydrocarbon group or a C1 to C12 alkoxy group, and m2 and n2 each independently represent an integer of 0 to 5. Examples of the aliphatic hydrocarbon group represented by $R^{b4}$, $R^{b5}$ and $R^{b6}$ include an alkyl group such as a methyl group, an ethyl group, a propyl group, an isopropyl group, a butyl group, a sec-butyl group, a tert-butyl group, a pentyl group, a hexyl group, an octyl group, and a 2-ethylhexyl group.

Examples of the aliphatic hydrocarbon group represented by $R^{b7}$ and $R^{b8}$ include an alkyl group such as a methyl group, an ethyl group, a propyl group, an isopropyl group, a butyl group, a sec-butyl group, a tert-butyl group, a pentyl group, a hexyl group, an octyl group, and a 2-ethylhexyl group.

The alicyclic hydrocarbon group represented by $R^{b4}$, $R^{b5}$ and $R^{b6}$ may be monocyclic or polycyclic, a hydrogen atom of which can be replaced by an alkyl group.

Examples of the monocyclic alicyclic hydrocarbon group include a cycloalkyl group such as a cyclopropyl group, a cyclobutyl group, a cyclopentyl group, a cyclohexyl group, a cycloheptyl group and a cyclodecyl group.

Examples of the polycyclic alicyclic hydrocarbon group include a decahydronaphtyl group, an adamantyl group, a norbornyl group, and the following ones.

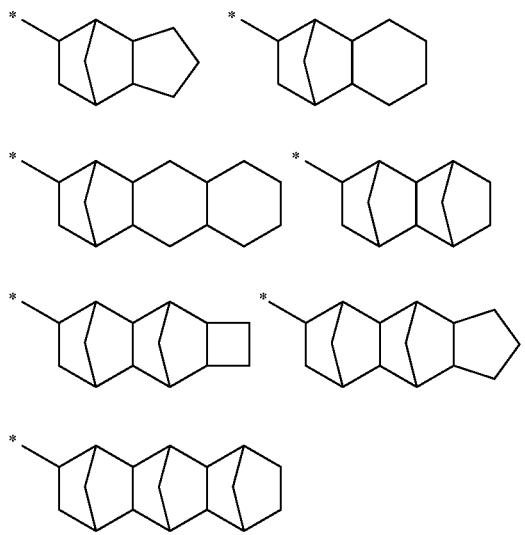

Examples of the alicyclic hydrocarbon group where a hydrogen atom has been replaced by an alkyl group include a methylcyclohexyl group, a 2-alkyladamantane-2-yl group, a methylnorbornyl group, and an isobornyl group.

The alicyclic hydrocarbon group where a hydrogen atom has been replaced by an alkyl group has preferably 20 or less of carbon atoms in total.

Preferred examples of the aromatic hydrocarbon group include an aryl group such as a phenyl group, a tolyl group, a xylyl group, a cumenyl group, a mesityl group, a (p-ethyl) phenyl group, a (p-tert-butyl)phenyl group, a (p-cyclohexyl) phenyl group, a (p-adamantyl)phenyl group, a biphenylyl group, a naphthyl group, a phenanthryl group, a 2,6-diethylphenyl group and a 2-methyl-6-ethylphenyl group.

Preferred examples of the aromatic hydrocarbon group where a hydrogen atom has been replaced by an alkoxy group include 4-methoxyphenyl group.

When an aromatic hydrocarbon group has an aliphatic hydrocarbon group or an alicyclic hydrocarbon group, the aliphatic hydrocarbon group has preferably 1 to 18 carbon atoms and the alicyclic hydrocarbon group has preferably 3 to 18 carbon atoms.

Examples of the aromatic hydrocarbon group in which a hydrogen atom has been replaced by an alkoxy group include a p-methoxyphenyl group.

Examples of the aliphatic hydrocarbon group in which a hydrogen atom has been replaced by an aromatic hydrocarbon group include aralkyl groups such as a benzyl group, a phenethyl group, a phenylpropyl group, a trityl group, a naphthylmethyl group and a naphthylethyl group.

Examples of the alkoxy group presented in the formulae (b2-1) and (b2-2) include a methoxy group, an ethoxy group, a propoxy group, a butoxy group, a pentyloxy group, a hexyloxy group, a heptyloxy group, an octyloxy group, a decyloxy group and a dodecyloxy group. Examples of the acyl group include an acetyl group, a propionyl group and a butyryl group.

Examples of the halogen atom include a fluorine atom, a chlorine atom, a bromine atom and an iodine atom.

The ring represented by two of $R^{b4}$, $R^{b5}$ and $R^{b6}$ together with $S^+$ may be a monocyclic ring, a polycyclic ring, an aromatic ring, a non-aromatic ring, a saturated ring or a unsaturated ring. The ring may contain a sulfur atom or oxygen atom in addition to S.

The ring preferably has 3 to 18 carbon atoms, and more preferably has 4 to 13 carbon atoms. Examples of such ring include 3 to 12-membered rings, preferably 3 to 7-membered rings, specifically the following ones.

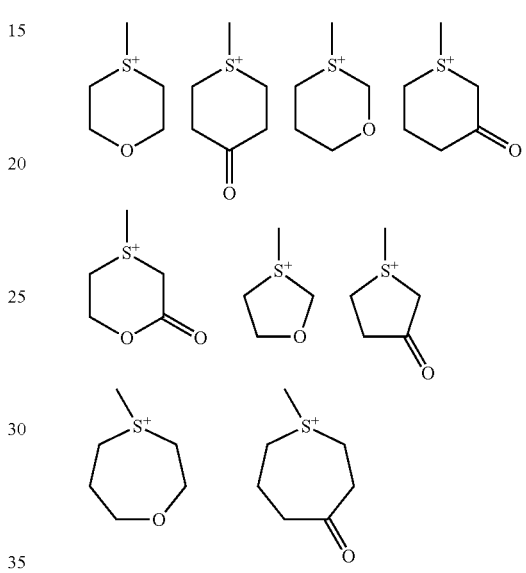

Among the cations represented by the formulae (b2-1) and (b2-2), preferred is the cation represented by the formula (b2-1). Examples of the cation represented by the formula (b2-1) include the following ones.

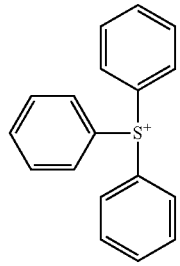

(b2-c-1)

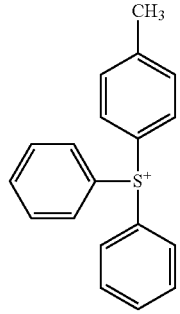

(b2-c-2)

-continued
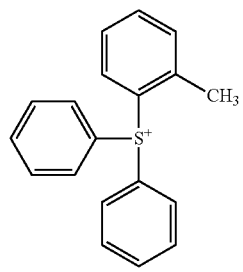
(b2-c-3)
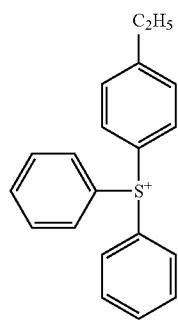
(b2-c-4)
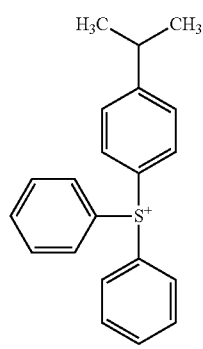
(b2-c-5)
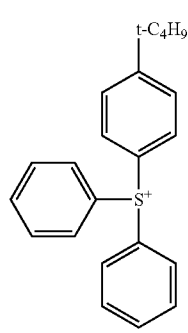
(b2-c-6)
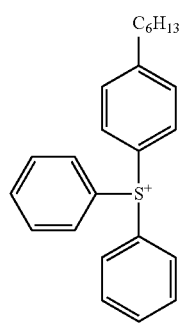
(b2-c-7)
-continued
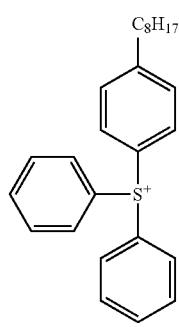
(b2-c-8)
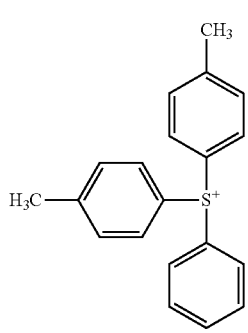
(b2-c-9)
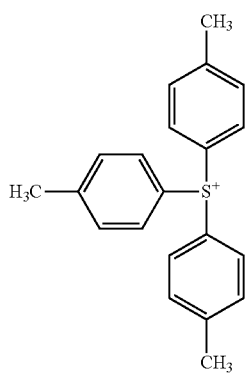
(b2-c-10)
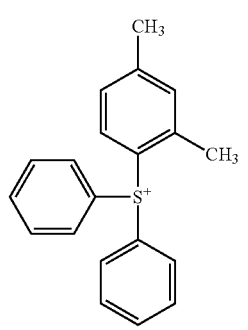
(b2-c-11)
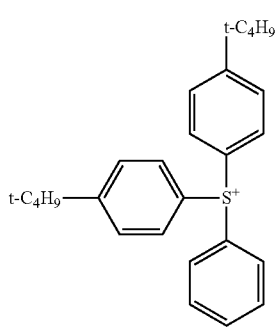
(b2-c-12)

(b2-c-13)
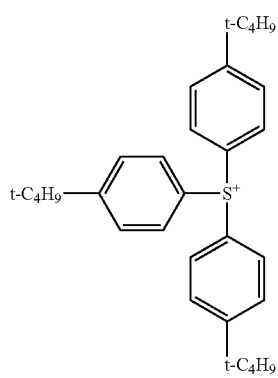
(b2-c-14)
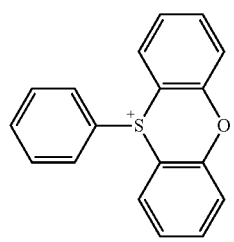
(b2-c-15)
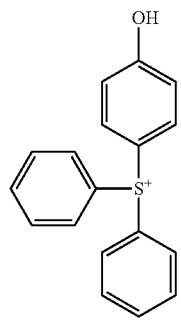
(b2-c-16)
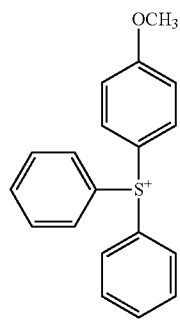
(b2-c-17)
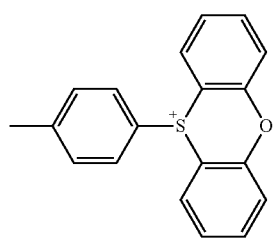
(b2-c-18)
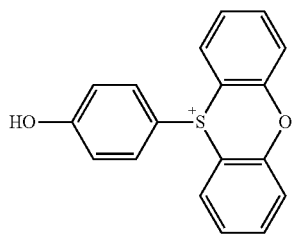
(b2-c-19)
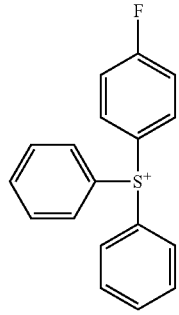
(b2-c-20)
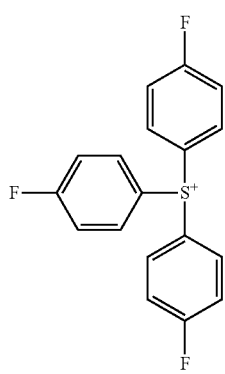
(b2-c-21)
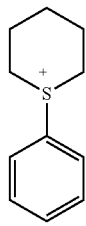
(b2-c-22)
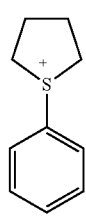
(b2-c-23)
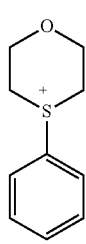

-continued

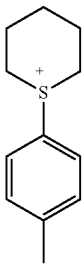
(b2-c-24)

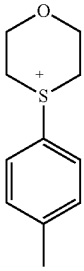
(b2-c-25)

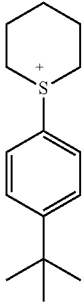
(b2-c-26)

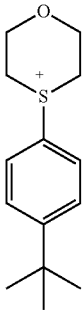
(b2-c-27)

Examples of the cation represented by the formula (b2-2) include the following ones.

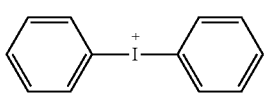
(b2-c-28)

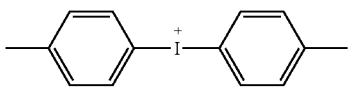
(b2-c-29)

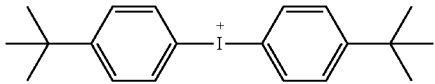
(b2-c-30)

Among them, the cations represented by formulae (b2-c-1), (b2-c-10), (b2-c-12), (b2-c-14), (b2-c-25), (b2-c-27), (b2-c-29) and (b2-c-30) are preferred, and those represented by formulae (b2-c-1), (b2-c-10), (b2-c-12), (b2-c-14), (b2-c-27) and (b2-c-30) are more preferred. Specific examples of the salt (I) are presented in Tables 1 to 3. In each of the tables, the symbols recited in each of the columns represent the symbol of formula representing a cation or an anion. For example, in Table 1, the salt (I-1) is a salt as shown below.

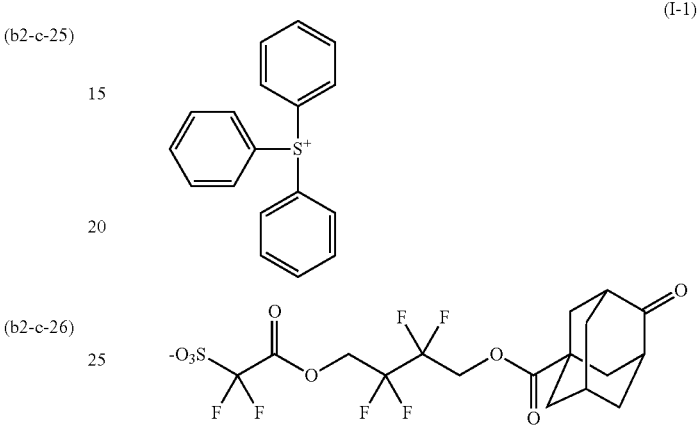
(I-1)

TABLE 1

| Salt (I) | Sulfonic acid anion | Cation |
| --- | --- | --- |
| (I-1) | (Ia-1) | (b2-c-1) |
| (I-2) | (Ia-2) | (b2-c-1) |
| (I-3) | (Ia-3) | (b2-c-1) |
| (I-4) | (Ia-4) | (b2-c-1) |
| (I-5) | (Ia-5) | (b2-c-1) |
| (I-6) | (Ia-6) | (b2-c-1) |
| (I-7) | (Ia-7) | (b2-c-1) |
| (I-8) | (Ia-8) | (b2-c-1) |
| (I-9) | (Ia-9) | (b2-c-1) |
| (I-10) | (Ia-10) | (b2-c-1) |
| (I-11) | (Ia-11) | (b2-c-1) |
| (I-12) | (Ia-12) | (b2-c-1) |
| (I-13) | (Ia-13) | (b2-c-1) |
| (I-14) | (Ia-14) | (b2-c-1) |
| (I-15) | (Ia-15) | (b2-c-1) |
| (I-16) | (Ia-16) | (b2-c-1) |
| (I-17) | (Ia-1) | (b2-c-10) |
| (I-18) | (Ia-2) | (b2-c-10) |
| (I-19) | (Ia-3) | (b2-c-10) |
| (I-20) | (Ia-4) | (b2-c-10) |
| (I-21) | (Ia-5) | (b2-c-10) |
| (I-22) | (Ia-6) | (b2-c-10) |
| (I-23) | (Ia-7) | (b2-c-10) |
| (I-24) | (Ia-8) | (b2-c-10) |
| (I-25) | (Ia-9) | (b2-c-10) |
| (I-26) | (Ia-10) | (b2-c-10) |
| (I-27) | (Ia-11) | (b2-c-10) |
| (I-28) | (Ia-12) | (b2-c-10) |
| (I-29) | (Ia-13) | (b2-c-10) |
| (I-30) | (Ia-14) | (b2-c-10) |

TABLE 2

| Salt (I) | Sulfonic acid anion | Cation |
| --- | --- | --- |
| (I-31) | (Ia-15) | (b2-c-10) |
| (I-32) | (Ia-16) | (b2-c-10) |
| (I-33) | (Ia-1) | (b2-c-12) |
| (I-34) | (Ia-2) | (b2-c-12) |

TABLE 2-continued

| Salt (I) | Sulfonic acid anion | Cation |
|---|---|---|
| (I-35) | (Ia-3) | (b2-c-12) |
| (I-36) | (Ia-4) | (b2-c-12) |
| (I-37) | (Ia-5) | (b2-c-12) |
| (I-38) | (Ia-6) | (b2-c-12) |
| (I-39) | (Ia-7) | (b2-c-12) |
| (I-40) | (Ia-8) | (b2-c-12) |
| (I-41) | (Ia-9) | (b2-c-12) |
| (I-42) | (Ia-10) | (b2-c-12) |
| (I-43) | (Ia-11) | (b2-c-12) |
| (I-44) | (Ia-12) | (b2-c-12) |
| (I-45) | (Ia-13) | (b2-c-12) |
| (I-46) | (Ia-14) | (b2-c-12) |
| (I-47) | (Ia-15) | (b2-c-12) |
| (I-48) | (Ia-16) | (b2-c-12) |
| (I-49) | (Ia-1) | (b2-c-14) |
| (I-50) | (Ia-2) | (b2-c-14) |
| (I-51) | (Ia-3) | (b2-c-14) |
| (I-52) | (Ia-4) | (b2-c-14) |
| (I-53) | (Ia-5) | (b2-c-14) |
| (I-54) | (Ia-6) | (b2-c-14) |
| (I-55) | (Ia-7) | (b2-c-14) |
| (I-56) | (Ia-8) | (b2-c-14) |
| (I-57) | (Ia-9) | (b2-c-14) |
| (I-58) | (Ia-10) | (b2-c-14) |
| (I-59) | (Ia-11) | (b2-c-14) |
| (I-60) | (Ia-12) | (b2-c-14) |
| (I-61) | (Ia-13) | (b2-c-14) |
| (I-62) | (Ia-14) | (b2-c-14) |
| (I-63) | (Ia-15) | (b2-c-14) |
| (I-64) | (Ia-16) | (b2-c-14) |
| (I-65) | (Ia-1) | (b2-c-27) |
| (I-66) | (Ia-2) | (b2-c-27) |
| (I-67) | (Ia-3) | (b2-c-27) |
| (I-68) | (Ia-4) | (b2-c-27) |
| (I-69) | (Ia-5) | (b2-c-27) |
| (I-70) | (Ia-6) | (b2-c-27) |
| (I-71) | (Ia-7) | (b2-c-27) |
| (I-72) | (Ia-8) | (b2-c-27) |
| (I-73) | (Ia-9) | (b2-c-27) |
| (I-74) | (Ia-10) | (b2-c-27) |
| (I-75) | (Ia-11) | (b2-c-27) |
| (I-76) | (Ia-12) | (b2-c-27) |

TABLE 3

| Salt (I) | Sulfonic acid anion | Cation |
|---|---|---|
| (I-77) | (Ia-13) | (b2-c-27) |
| (I-78) | (Ia-14) | (b2-c-27) |
| (I-79) | (Ia-15) | (b2-c-27) |
| (I-80) | (Ia-16) | (b2-c-27) |
| (I-81) | (Ia-1) | (b2-c-30) |
| (I-82) | (Ia-2) | (b2-c-30) |
| (I-83) | (Ia-3) | (b2-c-30) |
| (I-84) | (Ia-4) | (b2-c-30) |
| (I-85) | (Ia-5) | (b2-c-30) |
| (I-86) | (Ia-6) | (b2-c-30) |
| (I-87) | (Ia-7) | (b2-c-30) |
| (I-88) | (Ia-8) | (b2-c-30) |
| (I-89) | (Ia-9) | (b2-c-30) |
| (I-90) | (Ia-10) | (b2-c-30) |
| (I-91) | (Ia-11) | (b2-c-30) |
| (I-92) | (Ia-12) | (b2-c-30) |
| (I-93) | (Ia-13) | (b2-c-30) |
| (I-94) | (Ia-14) | (b2-c-30) |
| (I-95) | (Ia-15) | (b2-c-30) |
| (I-96) | (Ia-16) | (b2-c-30) |

Among them, preferred are the salt which consists of one of the anions represented by formulae (Ia-1) to (Ia-6) and one of the cations represented by formulae (b2-c-1), (b2-c-10), (b2-c-12), (b2-c-14), (b2-c-25), (b2-c-27), (b2-c-29) and (b2-c-30).

Among them, the salt (I) is preferably the salt (I-1), the salt (I-2), the salt (I-3), the salt (I-4), the salt (I-17), the salt (I-18), the salt (I-19), the salt (I-20), the salt (I-33), the salt (I-34), the salt (I-35), the salt (I-36), the salt (I-49), the salt (I-50), the salt (I-51), the salt (I-52), the salt (I-65), the salt (I-66), the salt (I-67), the salt (I-68), the salt (I-81), the salt (I-82), the salt (I-83), and the salt (I-84).

In the photoresist composition, the content of Salt (I) is usually 1 part by mass or more, preferably 2 parts by mass or more, with respect to 100 parts by mass of the resin (A). The content of Salt (I) is usually 40 parts by mass or less, preferably 35 parts by mass or less, with respect to 100 parts by mass of the resin (A). As the method for producing the salt (I), for example, the salt of formula (I) in which $X^1$ and $X^2$ each independently represent —CO—O—* (* represents a bonding site to $L^1$) and which salt is represented by the formula (I1) can be produced by reacting the salt represented by the formula (I1-a) and the compound of the formula (I1-b) in a solvent such as acetonitrile:

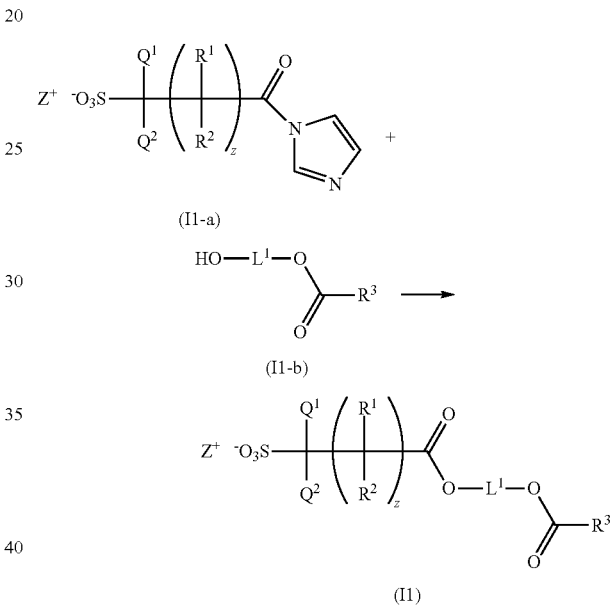

in which $Q^1$, $Q^2$, $R^1$, $R^2$, $R^3$, $L^1$, z and $Z^+$ are as defined above. The reaction of the compounds represented by the formulae (I1-a) and (I1-b) can be conducted at temperature of preferably 15° C. to 80° C., for 0.5 to 12 hours.

The compound of the formula (I1-a) can be obtained by reacting the compound of the formula (I1-c) and the compound of the formula (I1-d) in a solvent such as acetonitrile:

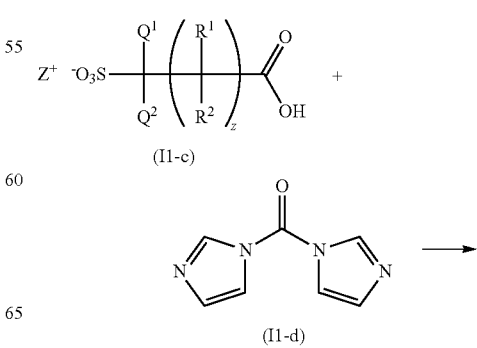

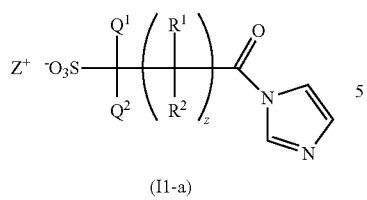

(I1-a)

in which $Q^1$, $Q^2$, $R^1$, $R^2$ and z are as defined above.

The reaction of the compounds represented by the formulae (I1-c) and (I1-d) can be conducted at temperature of preferably 15° C. to 80° C., for 0.5 to 12 hours.

Examples of the compound represented by the formula (I1-c) include the compound as follows, which can be produced by the method described in JP2008-127367A1.

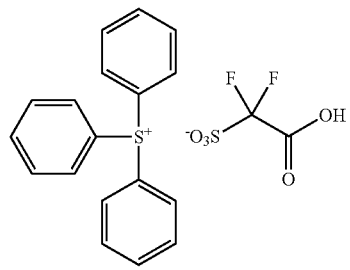

The compound of the formula (I1-b) can be obtained by reacting the compound of the formula (I1-e) and the compound of the formula (I1-f) in the presence of a catalyst and a solvent such as acetonitrile:

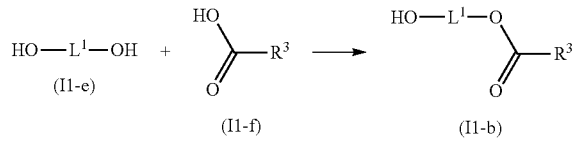

in which $L^1$ and $R^3$ are as defined above.

Examples of the catalyst include carbonyldiimidazole.

Examples of the compounds represented by the formula (I1-e) include the compound represented as follow, which are readily available on the market.

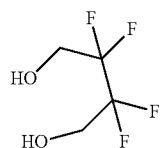

Examples of the compounds represented by the formula (I1-f) include the compounds represented as follow, which are readily available from the market.

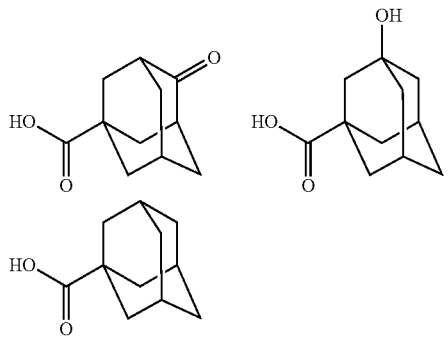

The salt (I) in which $R^2$ is an alicyclic hydrocarbon group having a cyclic ketal structure can be produced by reacting the salt (I) having an oxoadamantyl group as the group represented by $R^2$ with diol in the presence of an acid such as p-toluenesulfonic acid.

The reaction with an acid can be conducted at temperature of preferably 15° C. to 100° C., for 0.5 to 12 hours. Examples of diol include ethylene glycol, propane-1,3-diol, butane-1,4-diol and fluorobutane-1,4-diol.

The salt (I) in which $Z^+$ has a ring represented by formula (b2-x) can be produced by reacting a salt (I) which has the cation represented by formula (b2-2) with a compound represented by formula (I-65-a), in the presence of a catalyst such as copper (II) acetate, in a solvent such as chloroform:

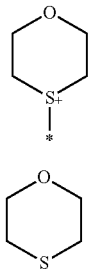

(b2-x)

(I-65-a)

The reaction can be conducted at temperature of preferably 15° C. to 120° C., for 0.5 to 12 hours.

The photoresist composition of the disclosure further contains a salt represented by the formula (B1), which is sometimes referred to as "Salt (B1)".

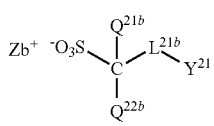

(B1)

In formula (B1) $Q^{21b}$ and $Q^{22b}$ each independently represent a fluorine atom or a C1-C6 perfluoroalkyl group, $L^{b21}$ represents a C1-C24 divalent saturated hydrocarbon group where a methylene group can be replaced by an oxygen atom or a carbonyl group and where a hydrogen atom can be replaced by a hydroxy group, $Y^{21}$ represents a C3-C18 alicyclic hydrocarbon group where a methylene group can be replaced by an oxygen atom, a sulfonyl group or a carbonyl group and where a hydrogen atom can be replaced by a hydroxy group or a fluorine atom, and $Zb^+$ represents an organic cation represented by any one of the formulae (b2-1) and (b2-2) as described above.

Examples of the perfluoroalkyl group represented by $Q^{21b}$ and $Q^{22b}$ include a trifluoromethyl group, a pentafluoroethyl group, a heptafluoropropyl group, a nonafluorobutyl group, an undecafluoropentyl group and a tridecafluorohexyl group. It is preferred that $Q^{21b}$ and $Q^{22b}$ each independently represent a fluorine atom or a trifluoromethyl group, and it is more preferred that $Q^{21b}$ and $Q^{22b}$ are fluorine atoms.

Examples of the divalent saturated hydrocarbon group represented by $L^{21b}$ include linear alkanediyl groups, branched chain alkanediyl groups, a monocyclic divalent alicyclic hydrocarbon group, a polycyclic divalent alicyclic hydrocarbon group and combinations of them.

Specific examples of them include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group;

branched chain alkanediyl groups including a group formed by attaching a side chain to a linear alkanediyl group, such as a butan-1,3-diyl group, a 2-methylpropane-1,3-diyl group, a 2-methylpropane-1,2-diyl group, a pentane-1,4-diyl group, and a 2-methylbutane-1,4-diyl group;

a monocyclic divalent alicyclic hydrocarbon group such as a cyclobutan-1,3-diyl group, cyclopentane-1,3-diyl group, a cyclohexane-1, 2-diyl group, a 1-methylcyclohexane-1, 2-diyl group, cyclohexane-1,4-diyl group, cyclooctane-1,2-diyl group, and a cyclooctane-1,5-diyl group; and a polycyclic divalent alicyclic hydrocarbon group such as a norbornane-2,3-diyl group, norbornane-1,4-diyl group, a norbornane-2,5-diyl group, an adamantane-1,2-diyl group, an adamantane-1,5-diyl group and an adamantane-1,6-diyl group.

When $L^{21b}$ represents a divalent saturated hydrocarbon group in which a methylene group has been replaced by an oxygen atom or a carbonyl group, examples of $L^{21b}$ include the moiety represented by any one of formulae (b1-1) to (b1-3) as follow;

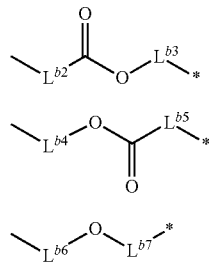

(b1-1)

(b1-2)

(b1-3)

wherein $L^{b2}$ represents a single bond or a C1 to C22 divalent saturated hydrocarbon group, and $L^{b3}$ represents a single bond or a C1 to C22 divalent saturated hydrocarbon group in which a hydrogen atom can be replaced by a hydroxyl group and in which a methylene group can be replaced by an oxygen atom or a carbonyl group, provided that $L^{b2}$ and $L^{b3}$ have 22 or less carbon atoms in total;

$L^{b4}$ represents a single bond or a C1 to C22 divalent saturated hydrocarbon group, and $L^{b5}$ represents a single bond or a C1 to C22 divalent saturated hydrocarbon group in which a hydrogen atom can be replaced by a hydroxyl group and in which a methylene group can be replaced by an oxygen atom or a carbonyl group, provided that $L^{b4}$ and $L^{b5}$ have 22 or less carbon atoms in total;

$L^{b6}$ represents a C1 to C15 divalent saturated hydrocarbon group in which a hydrogen atom can be replaced by a hydroxyl group, and $L^{b7}$ represents a single bond or a C1 to C15 divalent saturated hydrocarbon group in which a hydrogen atom can be replaced by a hydroxyl group and in which a methylene group can be replaced by an oxygen atom or a carbonyl group, provided that $L^{b6}$ and $L^{b7}$ have 23 or less carbon atoms in total; and * represents a binding site to Y In formula (b1-1) to formula (b1-3), when a methylene group has been replaced by an oxygen atom or a carbonyl group, the number of carbon atoms in the saturated hydrocarbon group corresponds to the number of the carbon atom before replacement.

Examples of the divalent saturated hydrocarbon group presented in formulae (b1-1) to formula (b1-3) are the same examples as the divalent saturated hydrocarbon group of $L^{b1}$.

$L^{b2}$ is preferably a single bond.

$L^{b3}$ is preferably a C1 to C4 divalent saturated hydrocarbon group.

$L^{b4}$ is preferably a C1 to C8 divalent saturated hydrocarbon group.

$L^{b5}$ is preferably a single bond or a C1 to C8 divalent saturated hydrocarbon group.

$L^{b6}$ is preferably a C1 to C4 divalent saturated hydrocarbon group.

$L^{b7}$ is preferably a single bond or a C1 to C18 divalent saturated hydrocarbon group where a hydrogen atom can be replaced by a hydroxy group, and where a methylene group can be replaced by an oxygen atom or a carbonyl group.

Among these, the group represented by the formula (b1-1) or the formula (b1-3) is preferred, and the group represented by the formula (b1-1) is more preferred.

Examples of the divalent group represented by the formula (b1-1) include the following groups represented by formula (b1-4) to formula (b1-8):

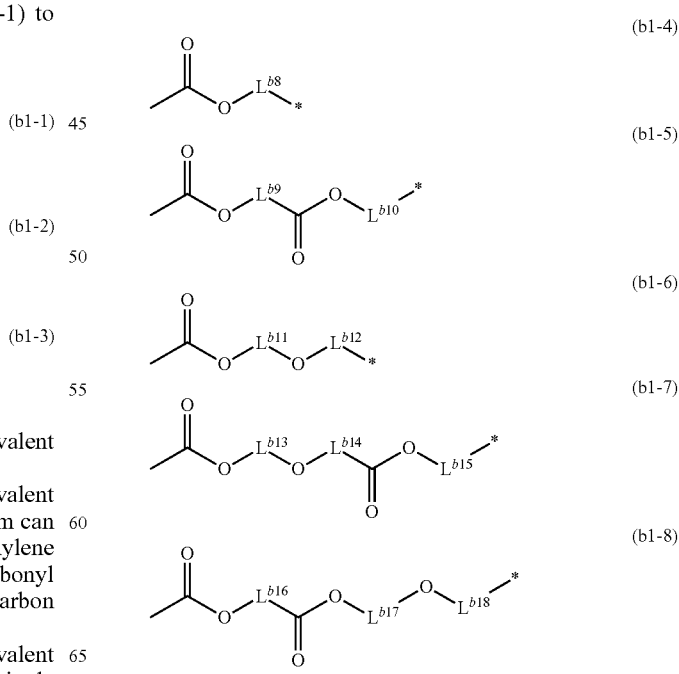

(b1-4)

(b1-5)

(b1-6)

(b1-7)

(b1-8)

wherein $L^{b8}$ represents a single bond or a C1 to C22 divalent saturated hydrocarbon group where a hydrogen atom can be replaced by a hydroxy group;

$L^{b9}$ represents a C1 to C20 divalent saturated hydrocarbon group, and $L^{b10}$ represents a single bond or a C1 to C19 divalent saturated hydrocarbon group where a hydrogen atom can be replaced by a hydroxy group, provided that $L^{b9}$ and $L^{b10}$ have 20 or less carbon atoms in total;

$L^{b11}$ represents a C1 to C21 divalent saturated hydrocarbon group, and $L^{b12}$ represents a single bond or a C1 to C20 divalent saturated hydrocarbon group where a hydrogen atom can be replaced by a hydroxy group, provided that $L^{b11}$ and $L^{b12}$ have 21 or less carbon atoms in total;

$L^{b13}$ represents a C1 to C19 divalent saturated hydrocarbon group, $L^{b14}$ represents a single bond or a C1 to C18 divalent saturated hydrocarbon group, and $L^{b15}$ represents a single bond or a C1 to C18 divalent saturated hydrocarbon group where a hydrogen atom can be replaced by a hydroxy group, provided that $L^{b13}$, $L^{b14}$ and $L^{b15}$ have 19 or less carbon atoms in total;

$L^{b16}$ represents a C1 to C18 divalent saturated hydrocarbon group, $L^{b17}$ represents a C1 to C18 divalent saturated hydrocarbon group, and $L^{b18}$ represents a single bond or a C1 to C17 divalent saturated hydrocarbon group where a hydrogen atom can be replaced by a hydroxy group, provided that $L^{b16}$, $L^{b17}$ and $L^{b18}$ have 19 or less carbon atoms in total; and * represents a binding site to $Y^{21}$.

$L^{b8}$ is preferably a C1 to C4 divalent saturated hydrocarbon group.

$L^{b9}$ is preferably a C1 to C8 divalent saturated hydrocarbon group.

$L^{b10}$ is preferably a single bond or a C1 to C19 divalent saturated hydrocarbon group, and more preferably a single bond or a C1 to C8 divalent saturated hydrocarbon group.

$L^{b11}$ is preferably a C1 to C8 divalent saturated hydrocarbon group.

$L^{b12}$ is preferably a single bond or a C1 to C8 divalent saturated hydrocarbon group.

$L^{b13}$ is preferably a C1 to C12 divalent saturated hydrocarbon group.

$L^{b14}$ is preferably a single bond or a C1 to C6 divalent saturated hydrocarbon group.

$L^{b15}$ is preferably a single bond or a C1 to C18 divalent saturated hydrocarbon group, and more preferably a single bond or a C1 to C8 divalent saturated hydrocarbon group.

$L^{b16}$ is preferably a C1 to C12 divalent saturated hydrocarbon group.

$L^{b17}$ is preferably a C1 to C6 divalent saturated hydrocarbon group.

$L^{b18}$ is preferably a single bond or a C1 to C17 divalent saturated hydrocarbon group, and more preferably a single bond or a C1 to C4 divalent saturated hydrocarbon group.

Examples of the divalent group represented by the formula (b1-3) include the following groups represented by formula (b1-9) to formula (b1-11):

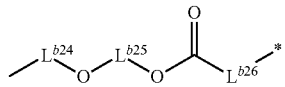

(b1-9)

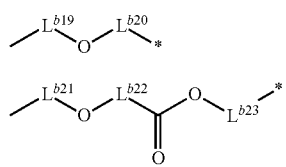

(b1-10)

(b1-11)

wherein $L^{b19}$ represents a single bond or a C1 to C23 divalent saturated hydrocarbon group, and $L^{b20}$ represent a single bond or a C1 to C23 divalent saturated hydrocarbon group where a hydrogen atom can be replaced by a hydroxy group or an acyloxy group, and a methylene group contained in an acyloxy group can be replaced by an oxygen atom or a carbonyl group, and a hydrogen atom contained in an acyloxy group can be replaced by a hydroxy group, provided $L^{b19}$ and $L^{b20}$ have 23 or less carbon atoms in total;

$L^{b21}$ represents a single bond or a C1 to C21 divalent saturated hydrocarbon group, $L^{b22}$ represents a single bond or a $C_1$ to $C_{21}$ divalent saturated hydrocarbon group, and $L^{b23}$ represents a single bond or a C1 to C21 divalent saturated hydrocarbon group where a hydrogen atom can be replaced by a hydroxy group or an acyloxy group, and a methylene group contained in an acyloxy group can be replaced by an oxygen atom or a carbonyl group, and a hydrogen atom contained in an acyloxy group can be replaced by a hydroxy group, provided that $L^{b21}$, $L^{b22}$ and $L^{b23}$ have 21 or less carbon atoms in total;

$L^{b24}$ represents a single bond or a C1 to C20 divalent saturated hydrocarbon group, $L^{b25}$ represents a single bond or a C1 to C21 divalent saturated hydrocarbon group, and $L^{b26}$ represents a single bond or a C1 to C20 divalent saturated hydrocarbon group where a hydrogen atom can be replaced by a hydroxy group or an acyloxy group, and a methylene group contained in an acyloxy group can be replaced by an oxygen atom or a carbonyl group, and a hydrogen atom contained in an acyloxy group can be replaced by a hydroxy group, provided that the total number of carbon atoms contained in the group of $L^{b24}$, $L^{b25}$ and $L^{b26}$ is 21 or less;

and * represents a binding site to $Y^{21}$.

In formula (b1-9) to formula (b1-11), when a hydrogen atom has been replaced by an acyloxy group, the number of the carbon atoms in the saturated hydrocarbon group corresponds to the number of the carbon atom, CO and O in addition to the number of the carbon atom in the saturated hydrocarbon group.

Examples of the acyloxy group include acetyloxy, propionyloxy, butyryloxy, cyclohexylcarbonyloxy and adamantyl carbonyloxy groups.

Examples of the acyloxy group having a substituent include oxoadamantylcarbonyloxy, hydroxyadamantylcarbonyloxy, oxocyclohexylcarbonyloxy and hydroxycyclohexylcarbonyloxy groups.

Examples of the group represented by the formula (b1-4) include the following ones:

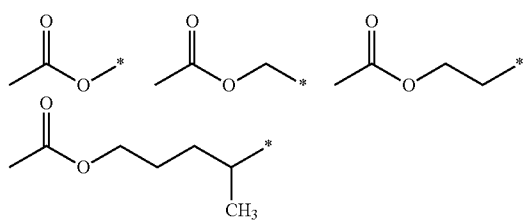

where * represents a binding site to $Y^{21}$.

Examples of the group represented by the formula (b1-5) include the following ones:
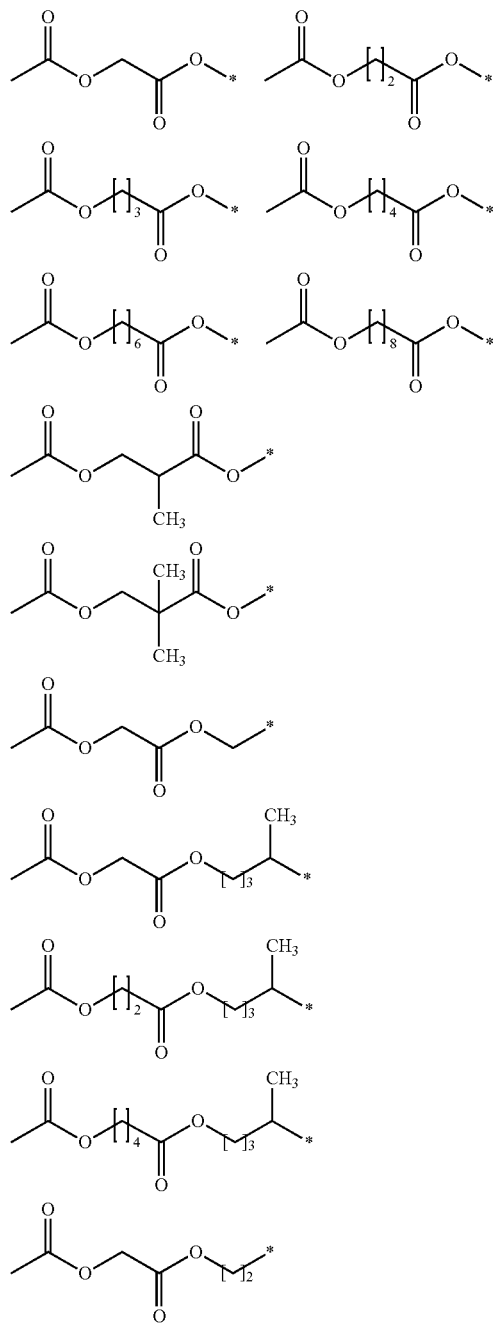
where * represents a binding site to $Y^{21}$.
Examples of the group represented by the formula (b1-6) include the following ones:
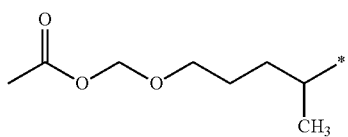
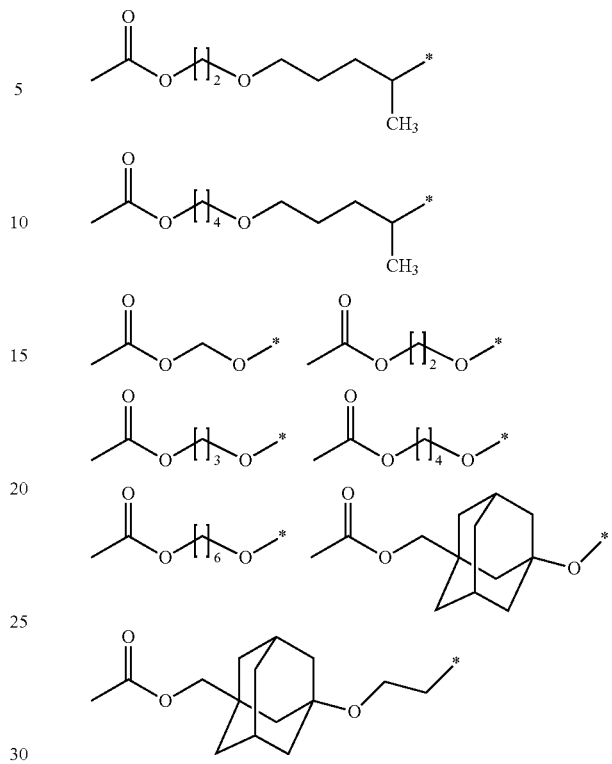
where * represents a binding site to $Y^{21}$.
Examples of the group represented by the formula (b1-7) include the following ones:
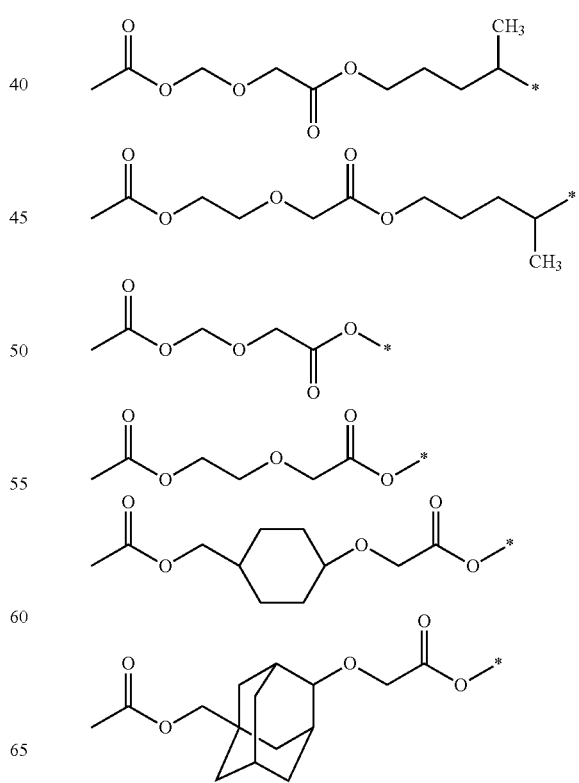

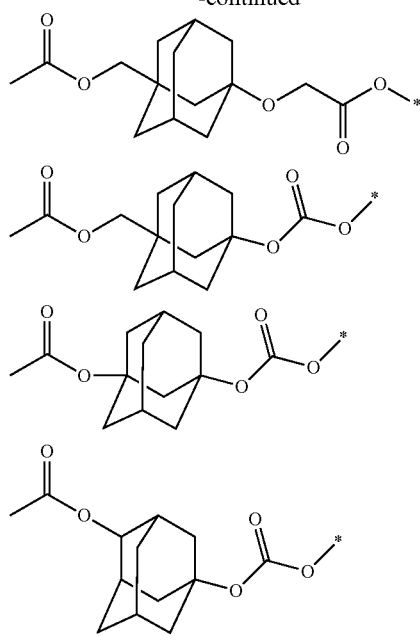

where * represents a binding site to $Y^{21}$.

Examples of the group represented by the formula (b1-8) include the following ones:

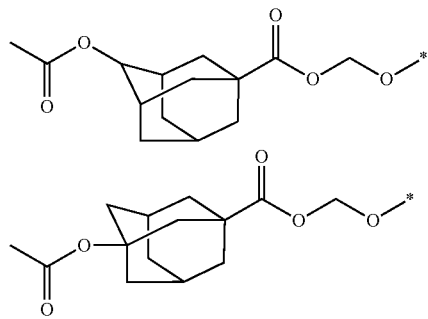

where * represents a binding site to $Y^{21}$.

Examples of the group represented by the formula (b1-2) include the following ones:

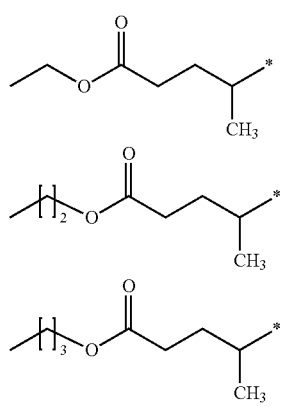

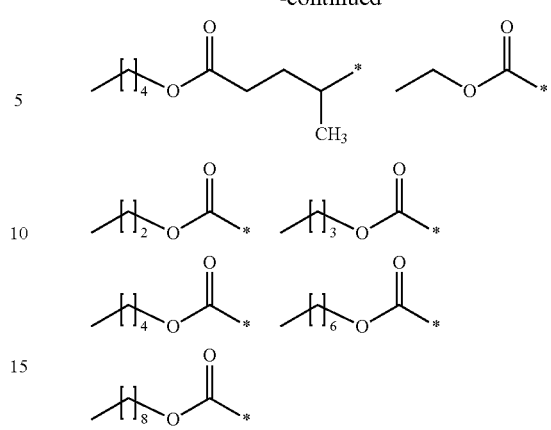

where * represents a binding site to $Y^{21}$.

Examples of the group represented by the formula (b1-9) include the following ones:

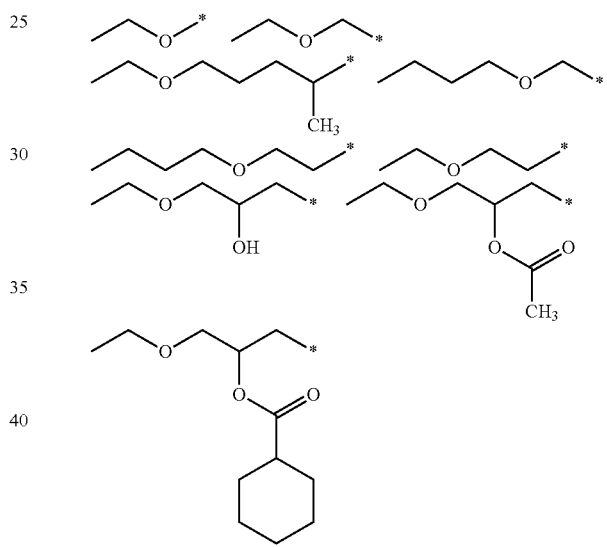

where * represents a binding site to $Y^{21}$.

Examples of the group represented by the formula (b1-10) include the following ones:

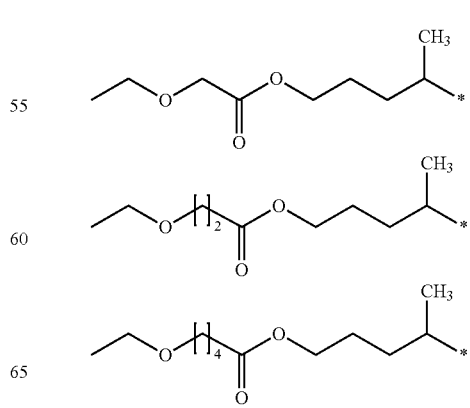

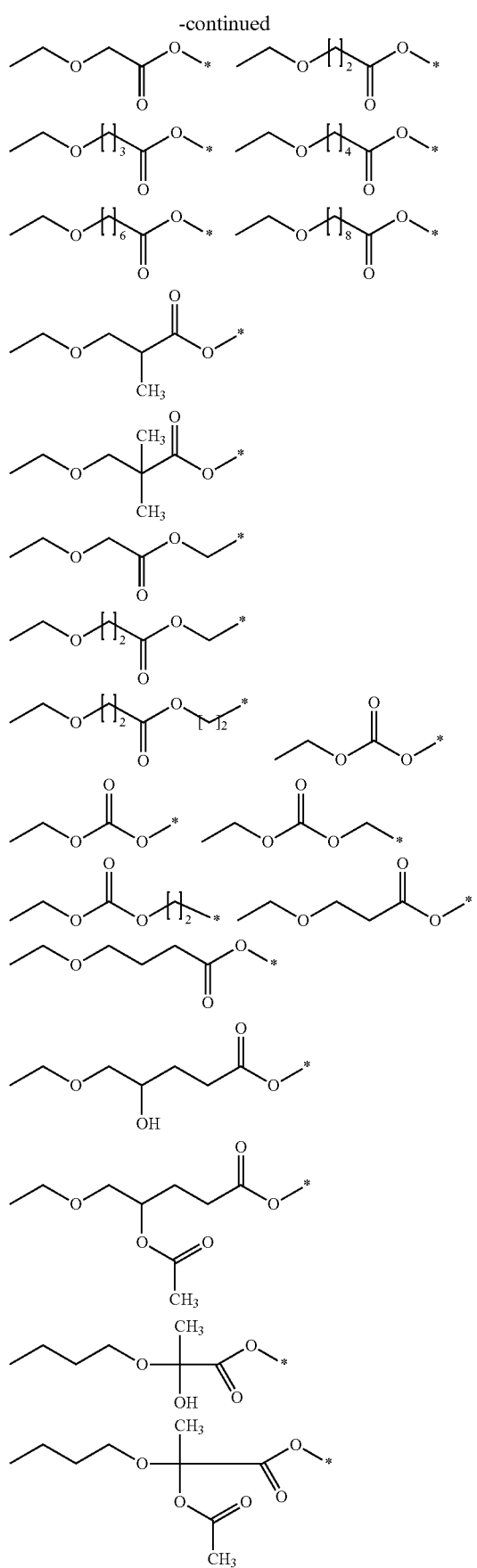
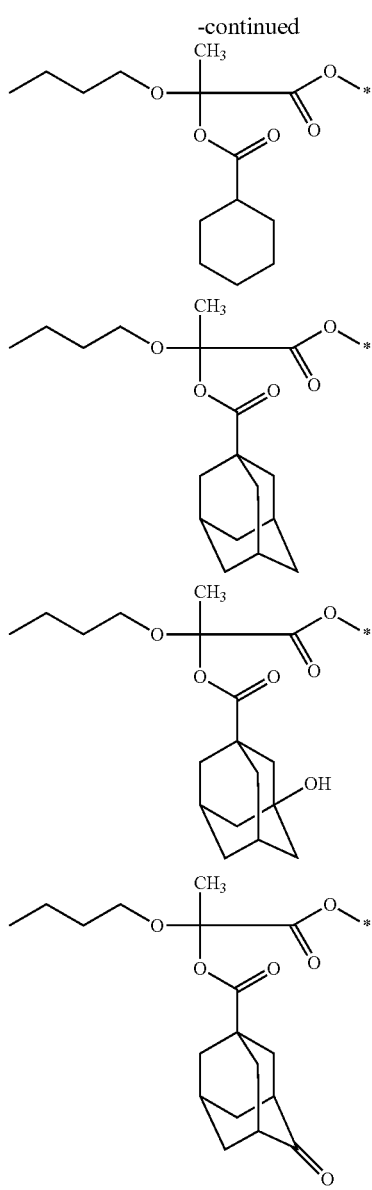
where * represents a binding site to $Y^{21}$.
Examples of the group represented by the formula (b1-11) include the following ones:
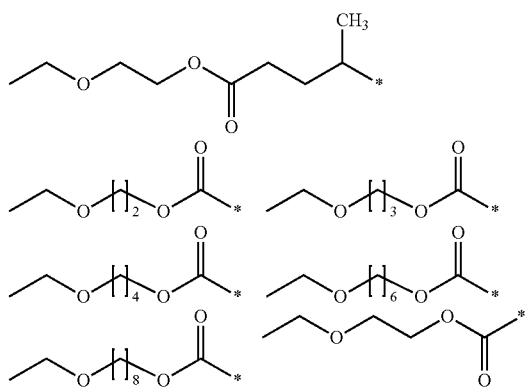

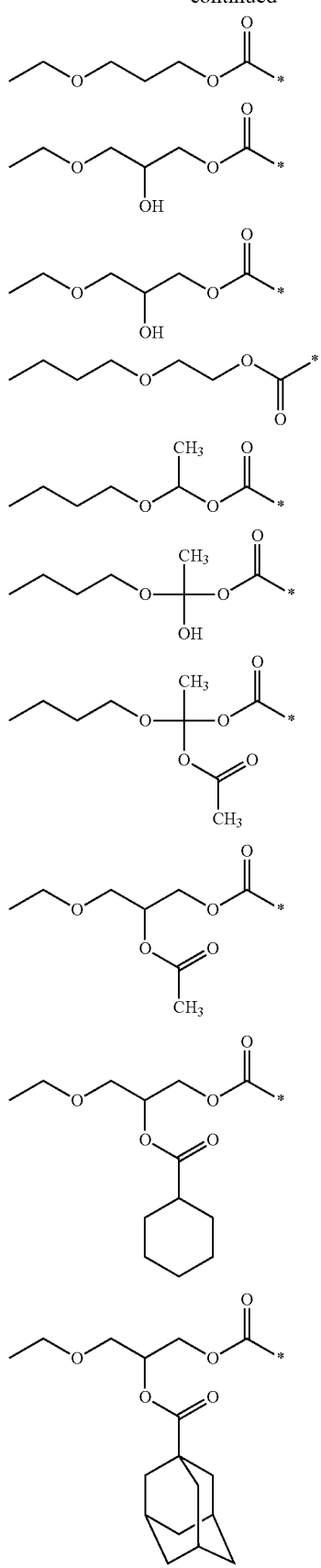

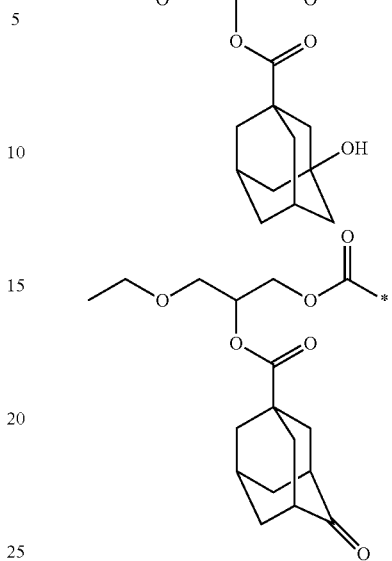

where * represents a binding site to $Y^{21}$.

$L^{21b}$ is preferably the group represented by the formula (b1-1), more preferably the group represented by the formula (b1-4), and still more preferably the group represented by the formula (b1-4) where $L^{b8}$ represents a single bond or a C1 to C22 divalent saturated hydrocarbon group.

Examples of the alicyclic hydrocarbon group represented by $Y^{21}$ include those represented by formulae (Y1) to (Y11).

Examples of the alicyclic hydrocarbon group represented by $Y^{21}$, in which a methylene group can be replaced by an oxygen atom, a sulfonyl group or a carbonyl group, include those represented by formulae (Y12) to (Y27).

 (Y1)

 (Y2)

 (Y3)

 (Y4)

 (Y5)

 (Y6)

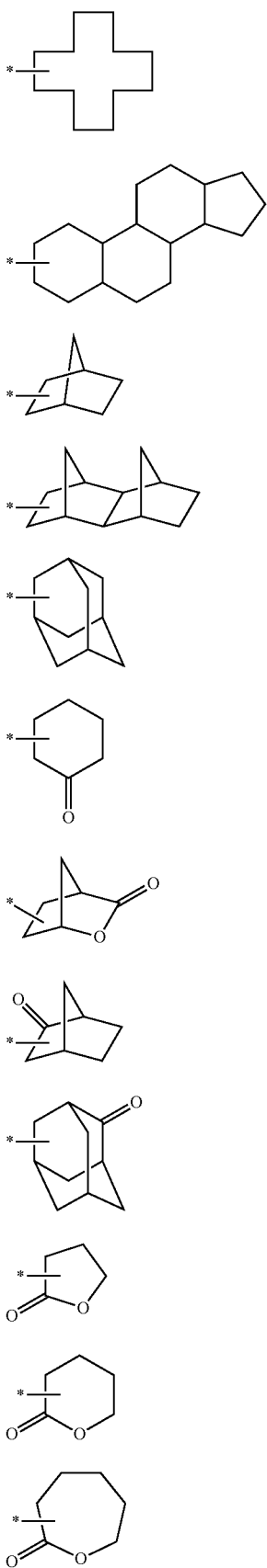
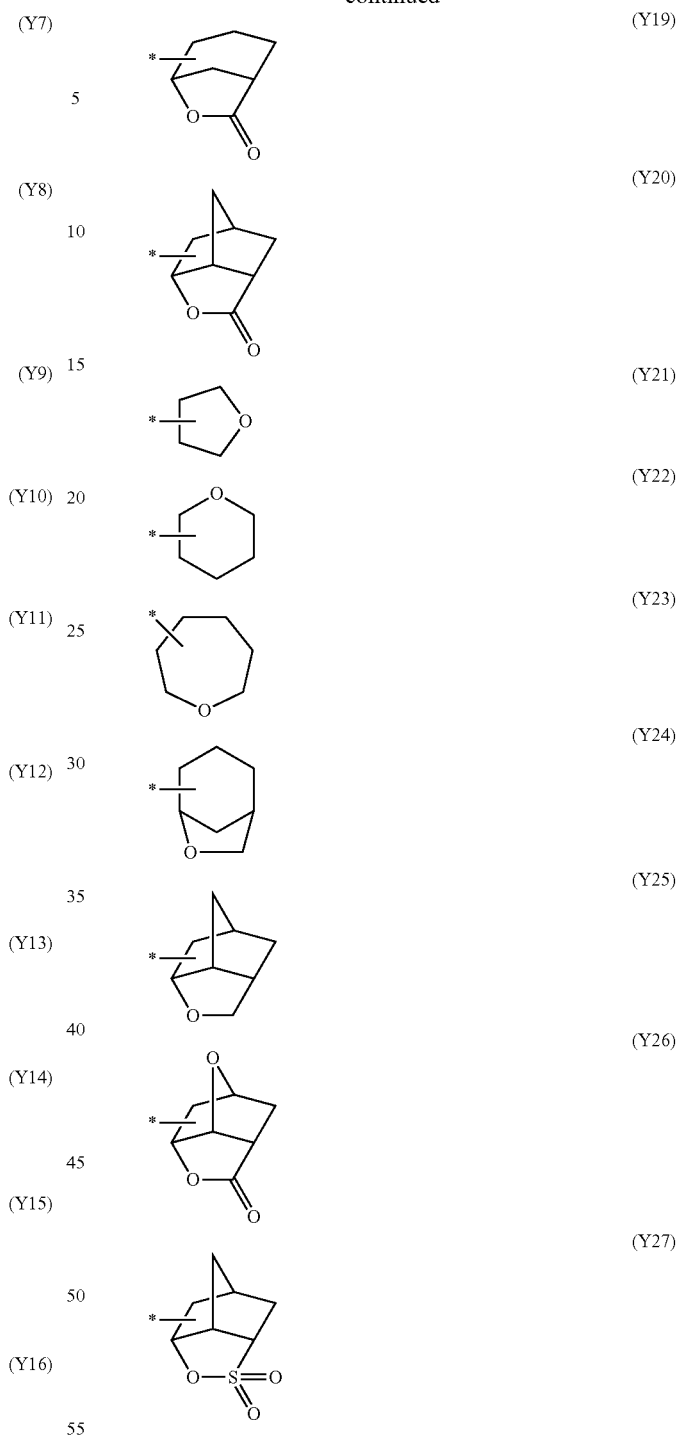

Among them, preferred are those represented by formulae (Y1) to (Y20), more preferred are those represented by formulae (Y11), (Y15), (Y16) and (Y20), and still more preferred are those represented by formulae (Y11) and (Y15).

Examples of the substituents for the alicyclic hydrocarbon group represented by $Y^{21}$ include a halogen atom, a hydroxy group, an oxo group, a C1 to C12 alkyl group, a C1 to C12 hydroxy-containing alkyl group, a C3 to C16 alicyclic hydrocarbon group, a C1 to C12 alkoxy group, a C6 to C18 aromatic hydrocarbon group optionally substituted with a C1-C4 alkyl group, a C7-C21 aralkyl group, a C2 to C4 acyl group, a glycidyloxy group, or —(CH$_2$)$_{j2}$O—CO—R$_{b1}$ group where R$_{b1}$ represents a C1 to C16 alkyl group, a C3 to C16 alicyclic hydrocarbon group, or a C6 to C18 aromatic hydrocarbon group optionally substituted with a C1 to C4 alkyl group. The symbol j2 represents an integer of 0 to 4.

Examples of the halogen atom include a fluorine atom, a chlorine atom, a bromine atom and an iodine atom.

Examples of the hydroxyl-containing methyl group include a hydroxymethyl group and a hydroxyethyl group.

Examples of alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of an aromatic hydrocarbon group include aryl groups such as aphenyl group, anaphthyl group, anantolyl group, a p-methylphenyl group, p-tert-butylphenyl group, p-adamantylphenyl group, a tolyl group, a xylyl group, a cumenyl group, a mesityl group, a biphenyl group, a phenanthryl group, a 2,6-diethylphenyl group, and 2-methyl-6-ethylphenyl group.

Examples of an aralkyl group include a benzyl group, a phenethyl group, a phenylpropyl group, a naphthylmethyl group and a naphthylethyl group.

Examples of an acyl group include an acetyl group, a propionyl group and a butyryl group.

Examples of the group represented by Y$^{21}$ include the following ones.

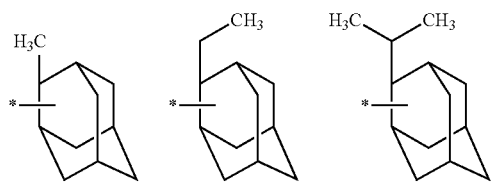

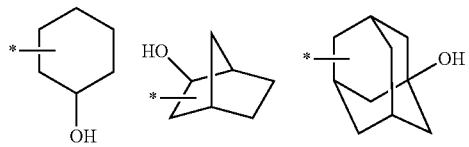

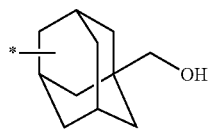

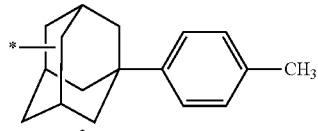

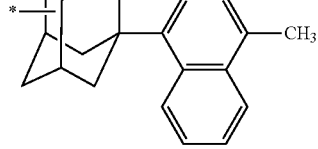

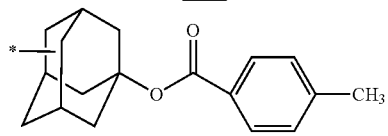

Y$^{21}$ is preferably a C3-C18 alicyclic hydrocarbon group which can have a substituent, more preferably an adamantyl group which can have a substituent such as oxo group or a hydroxyl group, more preferably an adamantyl group, a hydroxyadamantyl group, or an oxoadamantyl group.

Preferred examples of the sulfonic acid anion of the salt represented by formula (B1) include an anion represented by formulae (B1-A-1) to (B1-A-13).

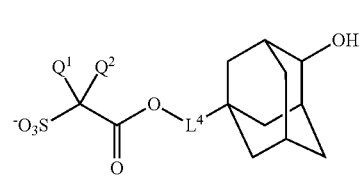
(B1-A-1)

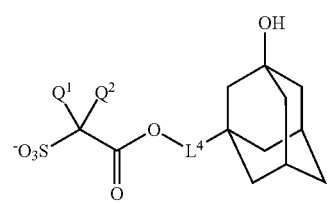
(B1-A-2)

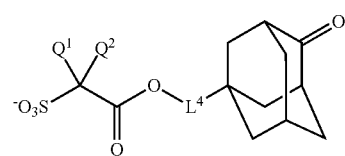
(B1-A-3)

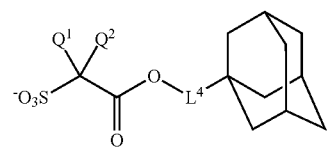
(B1-A-4)

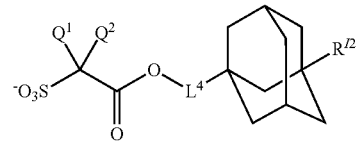
(B1-A-5)

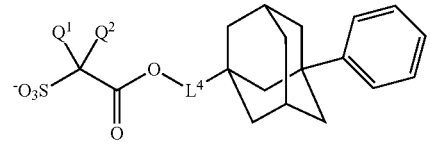
(B1-A-6)

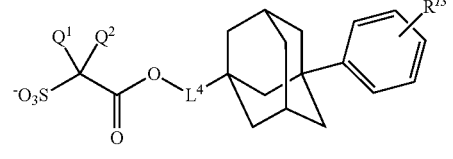
(B1-A-7)

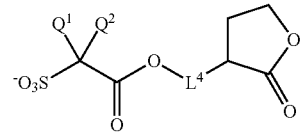
(B1-A-8)

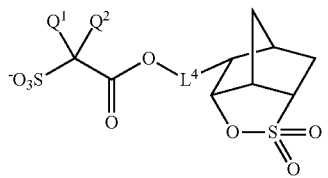
(B1-A-9)

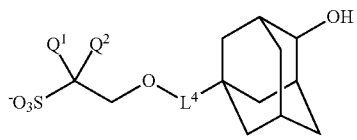
(B1-A-10)

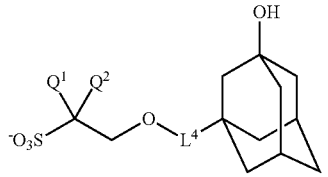
(B1-A-11)

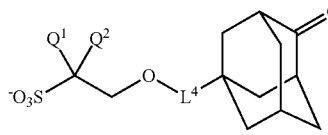
(B1-A-12)

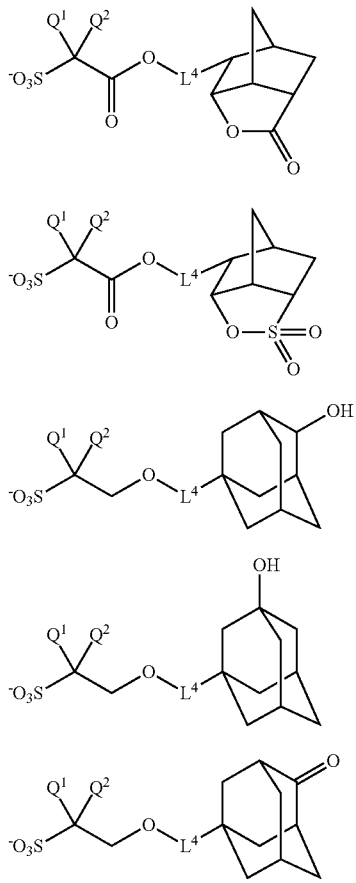
(B1-A-13)

In formula (B1-A-1) to formula (B1-A-13), $L^4$ represents a single bond or a $C_1$ to $C_4$ alkanediyl group. $Q^1$ and $Q^2$ represent the same meaning as $Q^{21b}$ and $Q^{22b}$ defined above, respectively.

In formula (B1), $Zb^+$ represents an organic cation represented by any one of formulae (b2-1) and (b2-2) as described above. Specific examples of the Salt (B1) include those represented by any of formulae (B1-1) to (B1-14) and (B1-17) to (B1-28).

Among them, the salt represented by formula (B1) preferably contains an arylsulfonium cation, and is more preferably a salt represented by any of formula (B1-1), formula (B1-2), formula (B1-3), formula (B1-6), formula (B1-7), formula (B1-11), formula (B1-12), formula (B1-13), formula (B1-14), formula (B1-20), formula (B1-21), formula (B1-22), formula (B1-23), formula (B1-24), formula (B1-25), and formula (B1-26).

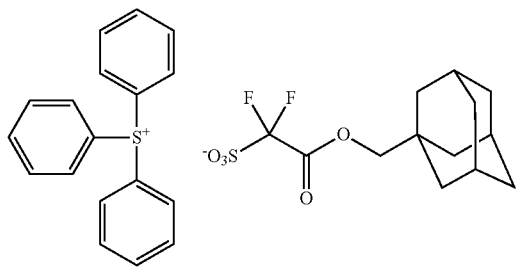
(B1-1)

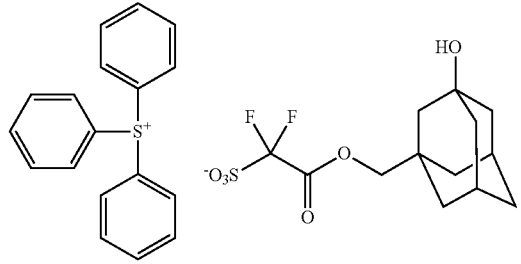
(B1-2)

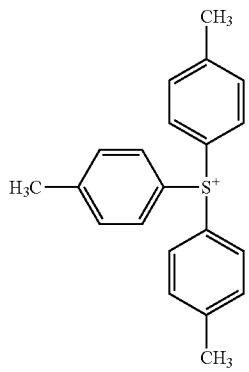

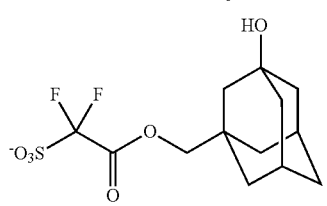
(B1-3)

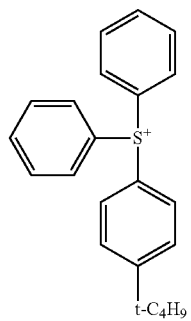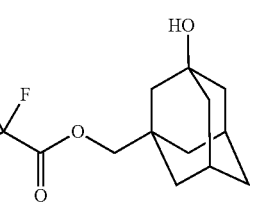
(B1-4)

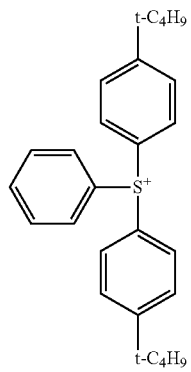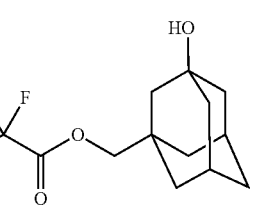
(B1-5)

(B1-6)
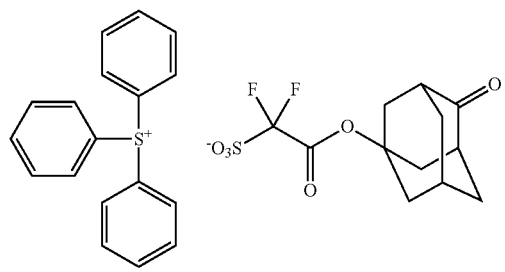
(B1-7)
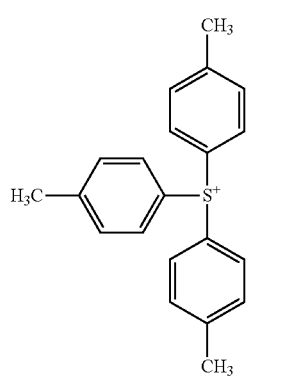
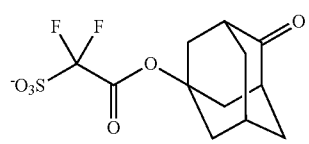
(B1-8)
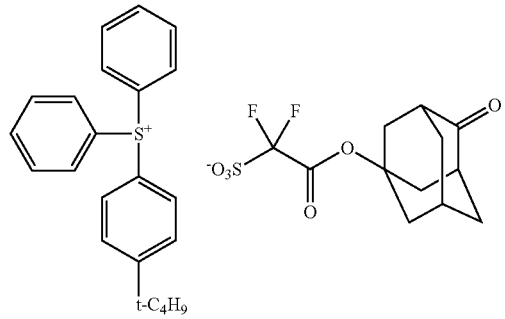
(B1-9)
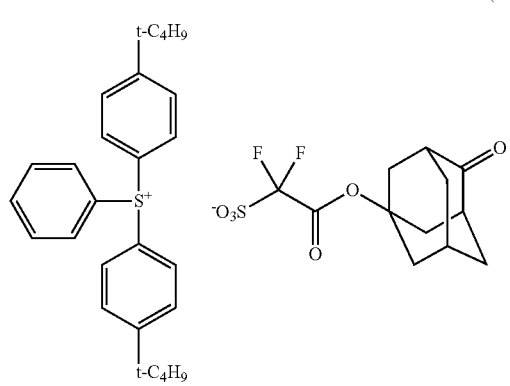
(B1-10)
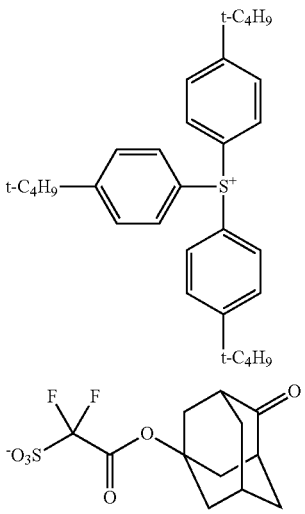
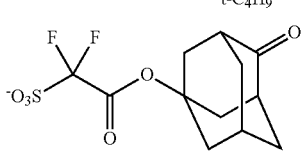
(B1-11)
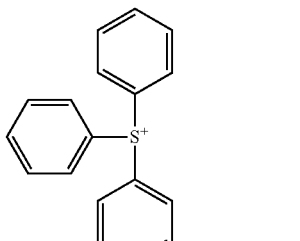
(B1-12)
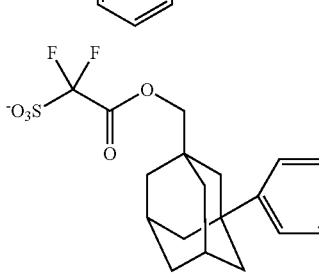
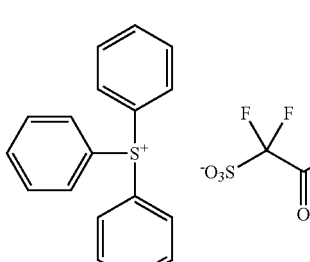
(B1-13)
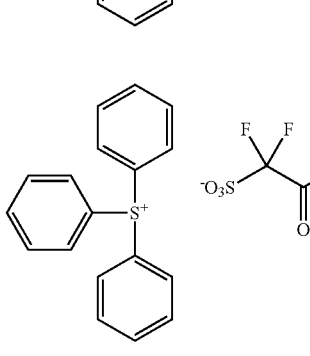

-continued
(B1-14)
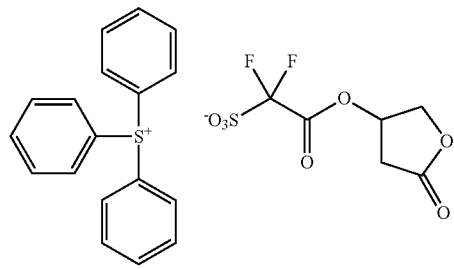
(B1-17)
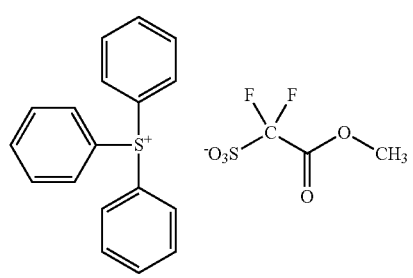
(B1-18)
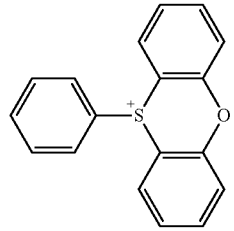
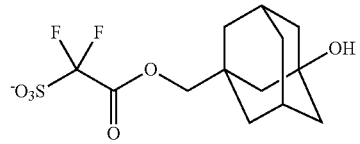
(B1-19)
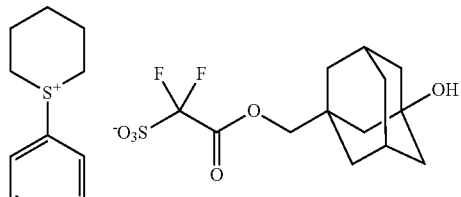
(B1-20)
(B1-21)
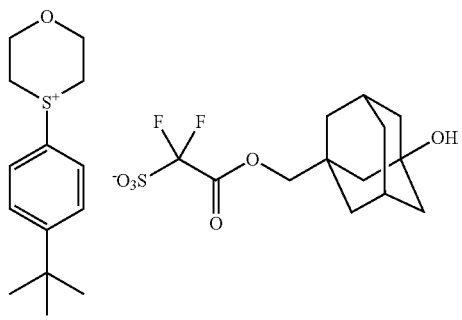
(B1-22)
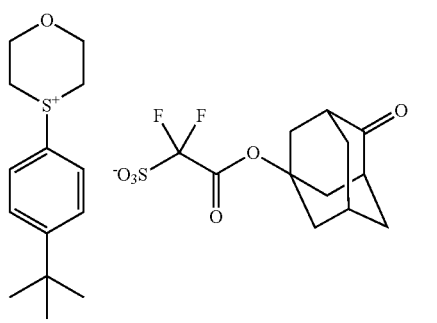
(B1-23)
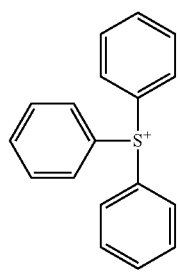
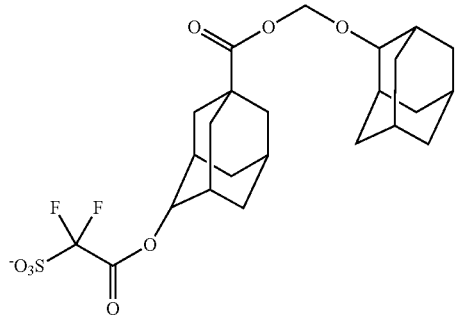
(B1-24)
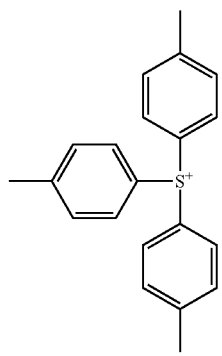

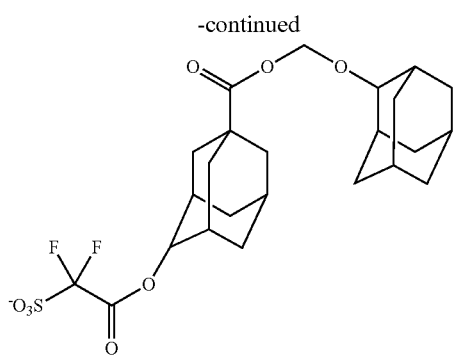

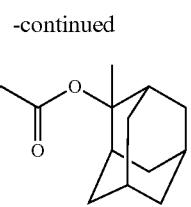

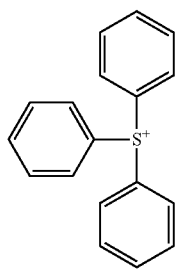

(B1-25)

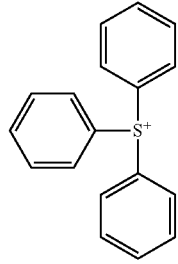

(B1-28)

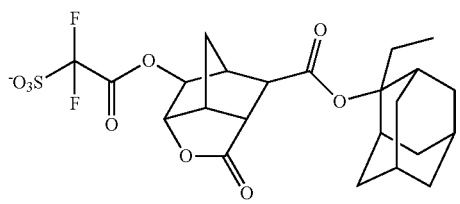

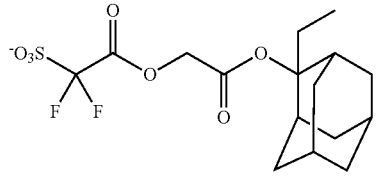

(B1-26)

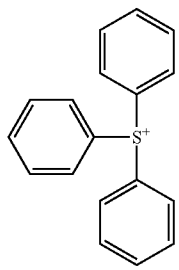

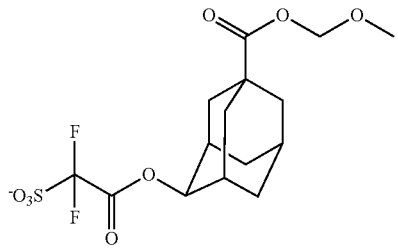

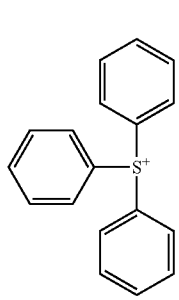

(B1-27)

In the photoresist composition of the disclosure, the amount of the Salt (B1) is preferably 1 part by mass to 40 parts by mass, more preferably 2 parts by mass to 35 parts by mass, and still more preferably 3 parts by mass to 35 parts with respect to 100 parts by mass of the resin (A).

In the photoresist composition of the disclosure, the amount ratio of the Salt (I) and the Salt (B1) [the Salt (I): the Salt (B1), weight ratio] is usually 1:99 to 99:1, preferably 2:98 to 98:2, more preferably 5:95 to 95:5.

In the photoresist composition of the disclosure, the total amount of the salt (I) and the Salt (B1) is preferably 1 parts by mass or more and more preferably 3 parts by mass or more, and preferably 40 parts by mass or less and more preferably 35 parts by mass or less with respect to 100 parts by mass of the resin (A).

<Resin (A)>

Resin (A) usually has a structural unit having an acid-labile group.

Hereinafter, the structural unit is sometimes referred to as "structural unit (a1)".

Preferably Resin (A) further has another structural unit than the structural unit (a1), i.e. a structural unit having no acid-labile group, which is sometimes referred to as "structural unit (s)".

In this specification, "an acid-labile group" means a functional group having a leaving group which is removed therefrom by the action of an acid to thereby form a hydrophilic group, such as a hydroxyl group or a carboxy group.

Examples of the acid-labile group include
a group represented by the formula (1):

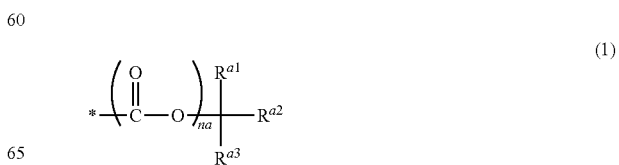

wherein $R^{a1}$, $R^{a2}$ and $R^{a3}$ independently each represent a C1-C8 alkyl group, a C3-C20 alicyclic hydrocarbon group or a group consisting of them, and $R^{a1}$ and $R^{a2}$ can be bonded each other to form a C2-C20 divalent alicyclic hydrocarbon group, "na" represents an integer of 0 or 1, and * represents a binding site; and a group represented by the formula (2):

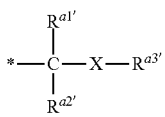
(2)

wherein $R^{a1'}$ and $R^{a2'}$ independently each represent a hydrogen atom or a C1-C12 hydrocarbon group, and $R^{a3'}$ represents a C1-C20 hydrocarbon group, and $R^{a2'}$ and $R^{a1'}$ can be bonded each other to form a C2-C20 divalent heterocyclic group, and one or more —$CH_2$— in the hydrocarbon group and the divalent heterocyclic group can be replaced by —O— or —S—, X represents an oxygen atom or a sulfur atom, and * represents a binding site.

For $R^{a1}$, $R^{a2}$ and $R^{a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings.

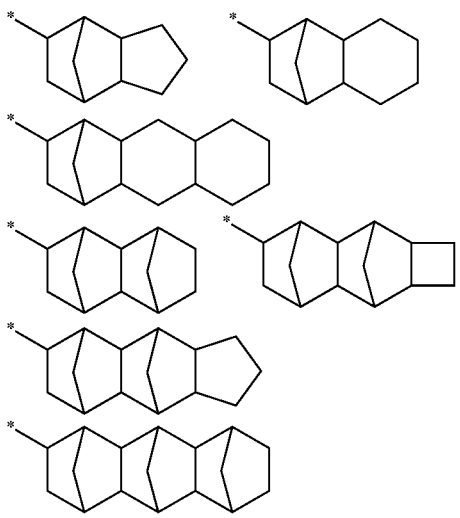

The alicyclic hydrocarbon group preferably has 3 to 16 carbon atoms. Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "na" is preferably 0.

When the divalent alicyclic hydrocarbon group is formed by bonding $R^{a1}$ and $R^{a2}$ each other, examples of the moiety —C($R^{a1}$)($R^{a2}$)($R^{a3}$) include the following groups and the divalent hydrocarbon group preferably has 3 to 12 carbon atoms.

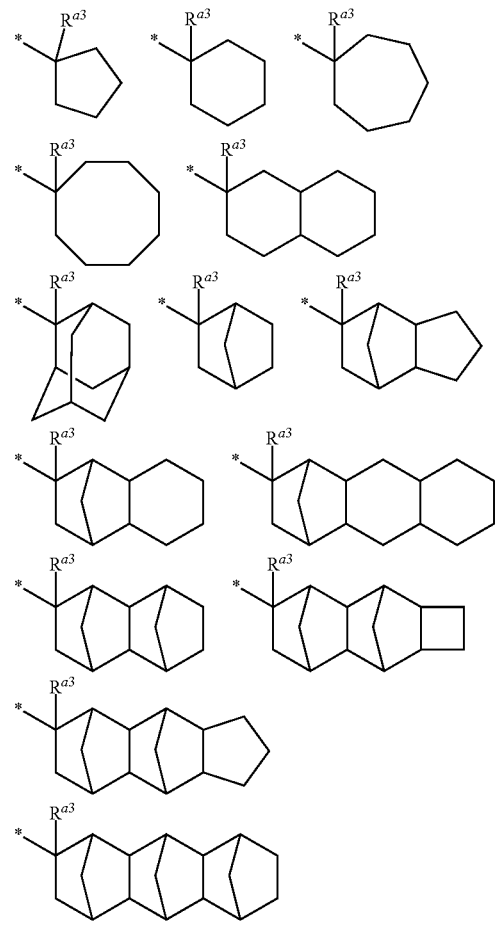

In each formula, $R^{a3}$ is the same as defined above.

Preferred are 1,1'-dialkylalkoxycarbonyl group, i.e., the group represented by the formula (1) wherein $R^{a1}$, $R^{a2}$ and $R^{a3}$ independently each represent a C1-C8 alkyl group such as a tert-butyl group;

2-alkyladamantane-2-yloxylcarbonyl group, i.e., the group represented by the formula (1) wherein $R^{a1}$ and $R^{a2}$ are bonded each other to form an adamantyl ring and $R^{a3}$ is a C1 to C8 alkyl group such as a 2-alkyl-2-adamantyl group; and 1-(adamantane-1-yl)-1-alkylalkoxycarbonyl group, i.e., the group represented by the formula (1) wherein $R^{a1}$ and $R^{a2}$ are C1 to C8 alkyl groups and $R^{a3}$ is an adamantyl group.

For formula (2), examples of the hydrocarbon group include an alkyl group, an alicyclic hydrocarbon group, an aromatic hydrocarbon group and a group consisting of two or more of them.

Examples of the alkyl group and the alicyclic hydrocarbon group include the same as described above. Examples of the aromatic hydrocarbon group include an aryl group such as a phenyl group, a naphthylgroup, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

When the divalent hydrocarbon group is formed by bonding $R^{a2'}$ and $R^{a3'}$ each other, examples of the moiety —C($R^{a1'}$) ($R^{a2'}$) ($R^{a3'}$) include the following groups.

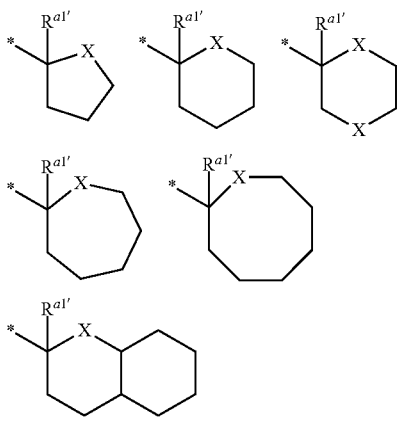

In each formula, $R^{a1'}$ and X are as defined above.

It is preferred that at least one of $R^{a1'}$ and $R^{a2'}$ is a hydrogen atom.

Examples of the group represented by the formula (2) include the following.

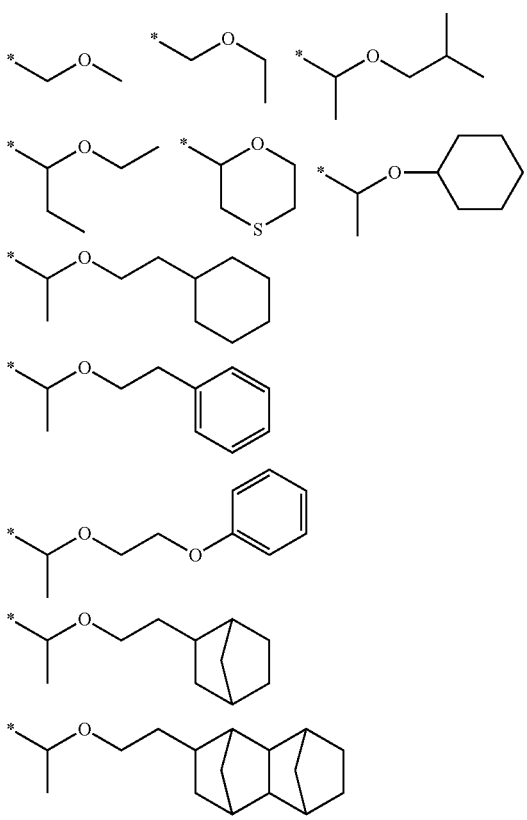

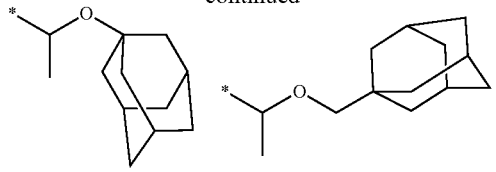

The structural unit (a1) is derived from a compound having an acid-labile group which compound is sometimes referred to as "Monomer (a1)"

Monomer (a1) is preferably a monomer having an acid-labile group and an ethylenic unsaturated group, more preferably a (meth)acrylate monomer having an acid-labile group, and still more preferably a (meth)acrylate monomer having the group represented by formula (1) or (2).

The (meth)acrylate monomer having an acid-labile group is preferably those which have a C5-C20 alicyclic hydrocarbon group. The resin which has a structural unit derived from such monomers can provide improved resolution for a photoresist pattern to be prepared therefrom.

The structural unit derived from a (meth)acrylate monomer having the group represented by formula (1) is preferably one of structural units represented by formulae (a1-0), (a1-1) and (a1-2):

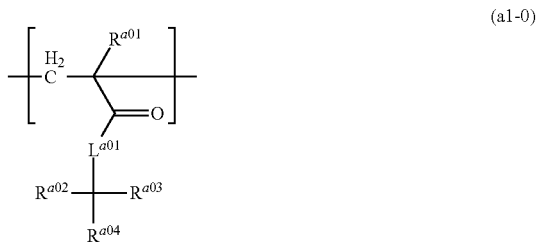

(a1-0)

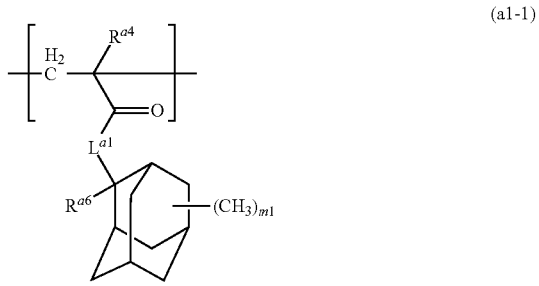

(a1-1)

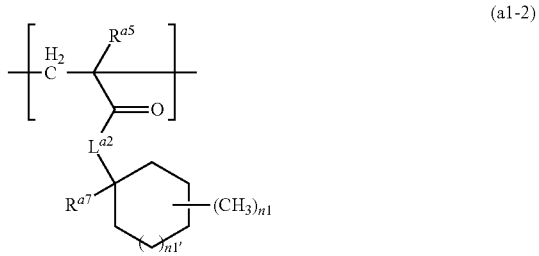

(a1-2)

where $L^{a01'}$, $L^{a1}$ and $L^{a2}$ each independently represent —O— or *—O—$(CH_2)_{k1}$—CO—O— in which k1 represents an integer of 1 to 7 and * represents a binding site to —CO—, $R^{a01}$, $R^{a4}$ and $R^{a5}$ each independently represent a hydrogen atom or a methyl group, $R^{a02}$, $R^{a03}$, $R^{a04}$, $R^{a6}$ and $R^{a7}$ each independently represent a C1 to C8 alkyl group, a C3-C18 alicyclic hydrocarbon group, or a group formed by combining them, m1 represents an integer of 0 to 14,
n1 represents an integer of 0 to 10, and
n1' represents an integer of 0 to 3.

Hereinafter, the structural units represented by formulae (a1-0), (a1-1) and (a1-2) are respectively referred to as "structural unit (a1-0)", "structural unit (a1-1)" and "structural unit (a1-2)". Resin (A) may have two or more of these structural units.

$L^{a01}$ is preferably *—O— or *—O—$(CH_2)_{f1}$—CO—O— in which * represents a binding site to —CO—, and f1 represents an integer of 1 to 4, and is more preferably *—O— or *—O—$CH_2$—CO—O—, and is especially preferably *—O—.

$R^{a01}$ is preferably a methyl group.

For $R^{a02}$, $R^{a03}$ and $R^{a04}$, examples of the alkyl group, the alicyclic hydrocarbon group and the group formed by combining them include the same as referred for $R^{a1}$, $R^{a2}$ and $R^{a3}$.

The alkyl group preferably has 1 to 6 carbon atoms.

The alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

The group formed by combining them preferably has 18 carbon atoms or less in total, examples of which include a methylcyclohexyl group, a dimethylcyclohexyl group, and a methylnorbornyl group. Each of $R^{a02}$ and $R^{a03}$ is preferably a C1-C6 alkyl group, more preferably a methyl group and an ethyl group.

$R^{a04}$ is preferably a C1-C6 alkyl group and a C5-C12 alicyclic hydrocarbon group, more preferably a methyl group, an ethyl group, a cyclohexyl group, and an adamantyl group.

Each of $L^{a1}$ and $L^{a2}$ is preferably *—O— or *—O—$(CH_2)_{f1}$—CO—O— in which * represents a binding site to —CO—, and f1 is the same as defined above, and is more preferably *—O— or * —O—$CH_2$—CO—O—, and is especially preferably *—O—.

Each of $R^{a4}$ and $R^{a5}$ is preferably a methyl group.

For $R^{a6}$ and $R^{a7}$, examples of the alkyl group include a methyl group, an ethyl group, a propyl group, an isopropyl group, a butyl group, a tert-butyl group, a pentyl group, a heptyl group, a 2-ethylheptyl group and an octyl group.

For $R^{a6}$ and $R^{a7}$, examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, a methylnorbornyl group.

For $R^{a6}$ and $R^{a7}$, examples of the group consisting of an alkyl group and an alicyclic hydrocarbon group include an aralkyl group such as a benzyl group, and a phenethyl group.

The alkyl group represented by $R^{a6}$ and $R^{a7}$ is preferably a C1 to C6 alkyl group.

The alicyclic hydrocarbon group represented by $R^{a6}$ and $R^{a7}$ is preferably a C3 to C8 alicyclic hydrocarbon group, more preferably a C3 to C6 alicyclic hydrocarbon group.

The "m1" is preferably an integer of 0 to 3, and is more preferably 0 or 1.

The "n1" is preferably an integer of 0 to 3, and is more preferably 0 or 1.

The "n1'" is preferably 0 or 1.

Examples of the structural unit (a1-0) include those represented by formulae (a1-0-1) to (a1-0-12), preferably those represented by formulae (a1-0-1) to (a1-0-10).

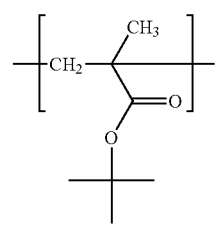

(a1-0-1)

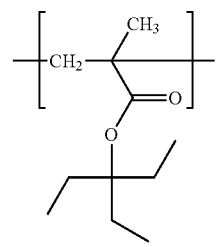

(a1-0-2)

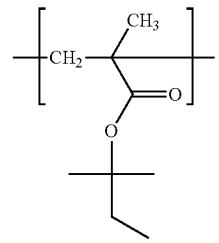

(a1-0-3)

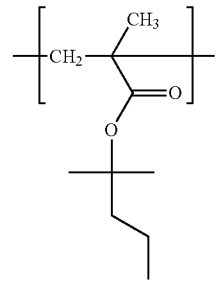

(a1-0-4)

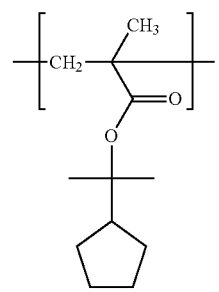

(a1-0-5)

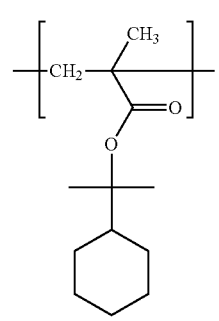

(a1-0-6)

-continued (a1-0-7)
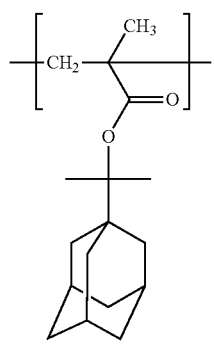

(a1-0-8)
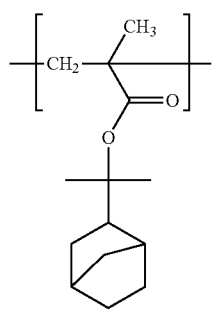

(a1-0-9)
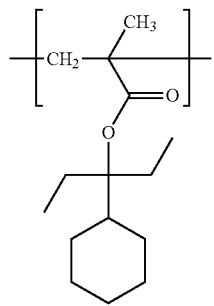

(a1-0-10)
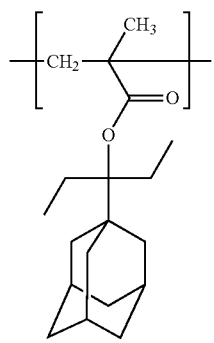

(a1-0-11)
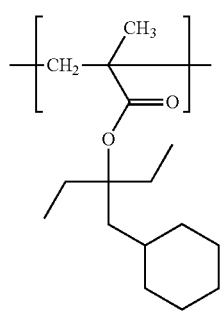

-continued (a1-0-12)
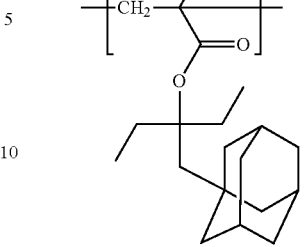

Examples of the structural unit (a1-0) further include such groups of formulae (a1-0-1) to (a1-0-12) in which a methyl group has been replaced by a hydrogen atom.

Examples of the monomer from which the structural unit (a1-1) is derived include the monomers described in JP2010-204646A1, and the following monomers represented by the formulae (a1-1-1) to (a1-1-8), preferably the following monomers represented by the formulae (a1-1-1) to (a1-1-4).

(a1-1-1)
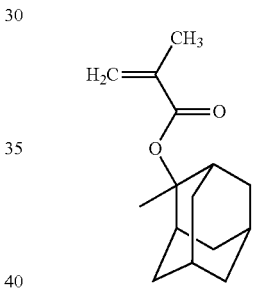

(a1-1-2)
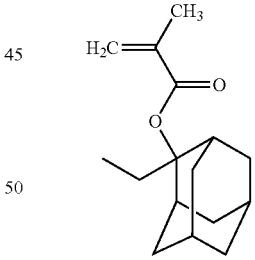

(a1-1-3)
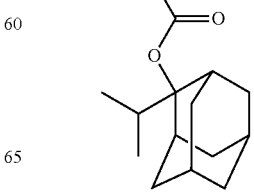

-continued

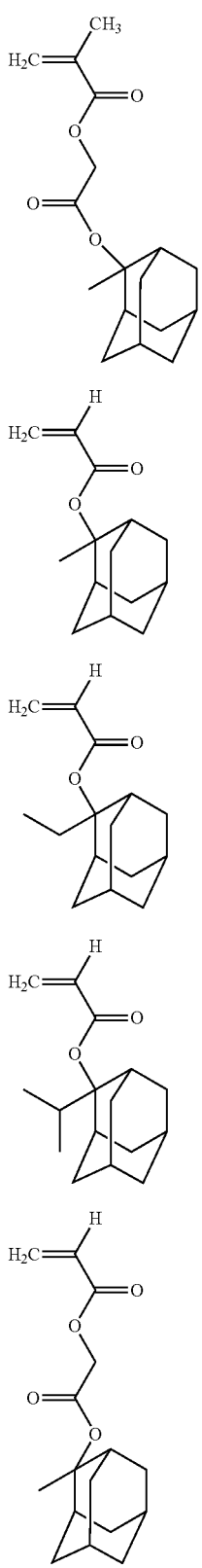

(a1-1-4)

(a1-1-5)

(a1-1-6)

(a1-1-7)

(a1-1-8)

Examples of the monomer from which the structural unit (a1-2) is derived include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcy-cloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-ylmethacrylate, preferably the monomers represented by the formulae (a1-2-1) to (a1-2-12), more preferably the monomers represented by the formulae (a1-2-3), (a1-2-4), (a1-2-9) and (a1-2-10), still more preferably the monomers represented by the formulae (a1-2-3) and (a1-2-9).

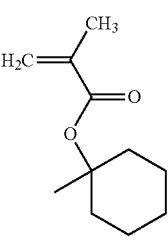

(a1-2-1)

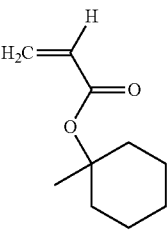

(a1-2-2)

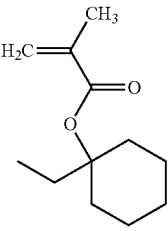

(a1-2-3)

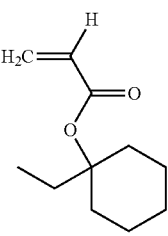

(a1-2-4)

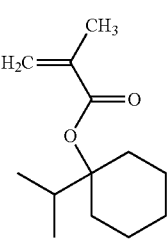

(a1-2-5)

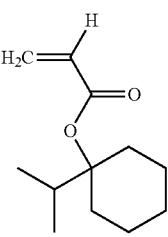

(a1-2-6)

(a1-2-7)
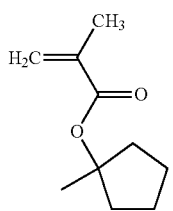

(a1-2-8)
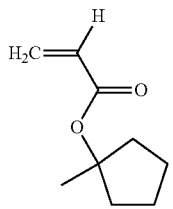

(a1-2-9)
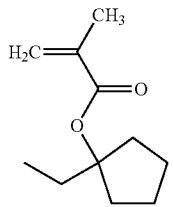

(a1-2-10)
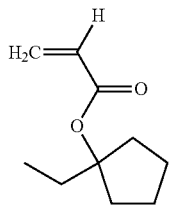

(a1-2-11)
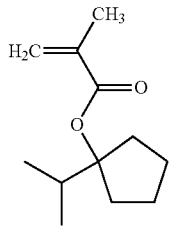

(a1-2-12)
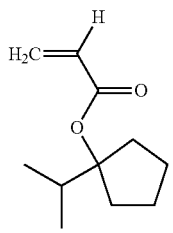

When the resin has one or more of the structural units represented by the formulae (a1-0), (a1-1) and (a1-2), the total content of the structural units is preferably 10 to 95% by mole and more preferably 15 to 90% by mole and still more preferably 20 to 85% by mole based on all the structural units of the resin.

Other examples of the structural unit (a) having a group of formula (1) include one represented by the formula (a1-3):

(a1-3)
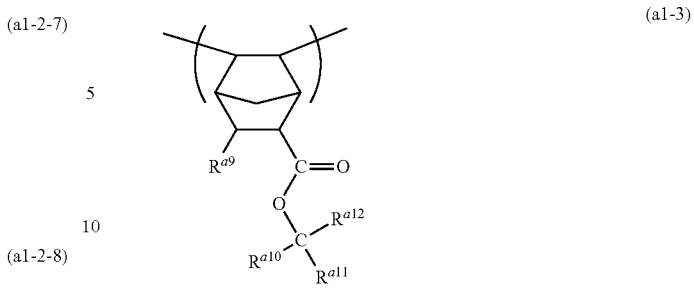

wherein $R^{a9}$ represents a hydrogen atom, a carboxyl group, a cyano group, a C1-C3 aliphatic hydrocarbon group which can have a hydroxyl group, or a group represented by —COOR$^{a13}$ group in which $R^{a13}$ represents a C1-C8 aliphatic hydrocarbon group or a C3-C20 alicyclic hydrocarbon group, and a group composed of a C1-C8 aliphatic hydrocarbon group and a C3-C20 alicyclic hydrocarbon group, and the aliphatic hydrocarbon group and the alicyclic hydrocarbon group can have a hydroxyl group, and a methylene in the aliphatic hydrocarbon group and the alicyclic hydrocarbon group can be replaced by —O— or —CO—, $R^{a10}$, $R^{a11}$ and $R^{a12}$ each independently represent a C1-C8 alkyl group or a C3-C20 alicyclic hydrocarbon group, and $R^{a10}$ and $R^{a11}$ can be bonded each other to form a C3-C20 ring together with the carbon atom to which $R^{a10}$ and $R^{a11}$ are bonded, and the alkyl group and the alicyclic hydrocarbon group can have a hydroxyl group, and amethylene group in the alkyl group and the alicyclic hydrocarbon group can be replaced by —O— or —CO—.

As $R^{a9}$, examples of the alkyl group which can have a hydroxyl group include a methyl group, an ethyl group, a propyl group, a hydroxymethyl group and a 2-hydroxyethyl group.

Examples of the aliphatic hydrocarbon group represented by $R^{a13}$ include a methyl group, an ethyl group and a propyl group.

Examples of the alicylic hydrocarbon group represented by $R^{a13}$ include a cyclopropyl group, a cyclobutyl group, an adamantyl group, an adamantylmethyl group, a 1-adamantyl-1-methylethyl group, a 2-oxo-oxolan-3-yl group and a 2-oxo-oxolan-4-yl group.

Examples of the alkyl group represented by $R^{a10}$, $R^{a11}$ and $R^{a12}$ include a methyl group, an ethyl group, n-propyl group, an isopropyl group, n-butyl group, sec-butyl group, tert-butyl group, a pentyl group, a hexyl group, a heptyl group, a 2-ethylhexyl group and an octyl group.

The alicyclic hydrocarbon group represented by $R^{a10}$, $R^{a11}$ and $R^{a12}$ may be a monocyclic or polycyclic group. Examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a hydronaphthyl group, an adamantyl group, a 2-alkyladamantane-2-yl group, a 1-(adamantane-1-yl)alkane-1-yl group, a norbornyl group, a methylnorbornyl group, and an isobornyl group.

When the divalent hydrocarbon group is formed by bonding $R^{a10}$ and $R^{a11}$, examples of —C($R^{a10}$) ($R^{a11}$) ($R^{a12}$) include the following ones;

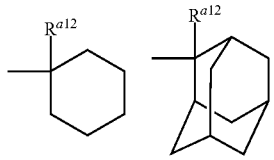

where $R^{a12}$ is as defined above.

Examples of the monomer from which the structural unit represented by the formula (a1-3) is derived include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit represented by the formula (a1-3), the photoresist composition having excellent resolution and higher dry-etching resistance tends to be obtained.

When Resin (A) has the structural unit represented by the formula (a1-3), the content of the structural unit is usually 10 to 95% by mole and preferably 15 to 90% by mole and more preferably 20 to 85% by mole based on all the structural units of the resin.

Other examples of the structural unit (a) having a group of formula (2) include one represented by the formula (a1-4):

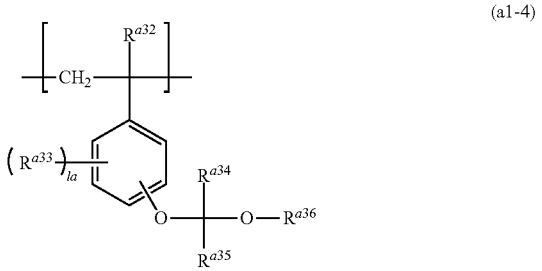

(a1-4)

wherein $R^{a32}$ represents a hydrogen atom, a halogen atom, a C1-C6 alkyl group or a C1-C6 halogenated alkyl group, $R^{a33}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, 1a represents an integer of 0 to 4,
$R^{a34}$ and $R^{a35}$ each independently represent a hydrogen atom or a C1-C12 hydrocarbon group, $R^{a36}$ represents a C1-C20 hydrocarbon group in which a methylene group can be replaced by —O— or —S—, and $R^{a35}$ and $R^{a36}$ are bonded to each other to jointly represent a C2-C20 divalent hydrocarbon group in which a methylene group can be replaced by —O— or —S—.

Examples of the alkyl group represented by $R^{a32}$ and $R^{a33}$ include a methyl group, an ethyl group, a propyl group, a butyl group, a pentyl group, and a hexyl group, preferably a C1-C4 alkyl group, more preferably a methyl group and an ethyl group, and still more preferably a methyl group.

Examples of halogen atom represented by $R^{a32}$ and $R^{a33}$ include a fluorine atom, a chlorine atom, and a bromine atom.

Examples of the alkoxy group represented by $R^{a33}$ include a methoxy group, an ethoxy group, a propoxy group, an isopropoxy group, a butoxy group, an isobutoxy group, a sec-butoxy group, a tert-butoxy group, a pentyloxy group and a hexyloxy group.

Examples of the acyl group represented by $R^{a33}$ include an acetyl group, a propyonyl group and a butyryl group, and examples of the acyloxy group represented by $R^{a33}$ include an acetyloxy group, a propyonyloxy group and a butyryloxy group.

Examples of the groups represented by $R^{a34}$ and $R^{a35}$ include those as referred to for $R^{a1'}$ and $R^{a2'}$.

Examples of the groups represented by $R^{a36}$ include those as referred to for $R^{a3'}$.

$R^{a32}$ preferably represents a hydrogen atom.

$R^{a33}$ is preferably a C1-C4 alkoxy group, more preferably a methoxy group and an ethoxy group, and still more preferably a methoxy group.

The symbol "1a" preferably represents 0 or 1, more preferably 1.

$R^{a34}$ preferably represents a hydrogen atom.

$R^{a35}$ is preferably a C1-C12 monovalent hydrocarbon group, more preferably a methyl group and an ethyl group.

The hydrocarbon group represented by $R^{a36}$ includes a C1-C18 alkyl group, a C3-C18 monovalent alicyclic hydrocarbon group, a C6-C18 monovalent aromatic hydrocarbon group, and any combination of them, and preferably a C1-C18 alkyl group, a C3-C18 monovalent alicyclic hydrocarbon group and a C7-C18 aralkyl group. These groups may be unsubstituted or substituted. The alkyl group and the monovalent alicyclic hydrocarbon group are preferably unsubstituted. As the substituent for the monovalent aromatic hydrocarbon group, a C6 to C10 aryloxy group is preferred.

Examples of the monomer from which the structural unit represented by formula (a1-4) is derived include monomers recited in JP2010-204646A1. Among them, the monomers represented by formulae (a1-4-1), (a1-4-2), (a1-4-3), (a1-4-4), (a1-4-5), (a1-4-6), (a1-4-7) and (a1-4-8) are preferred, and the monomers represented by formulae (a1-4-1), (a1-4-2), (a1-4-3), (a1-4-4), (a1-4-5) and (a1-4-8) are more preferred.

(a1-4-1)

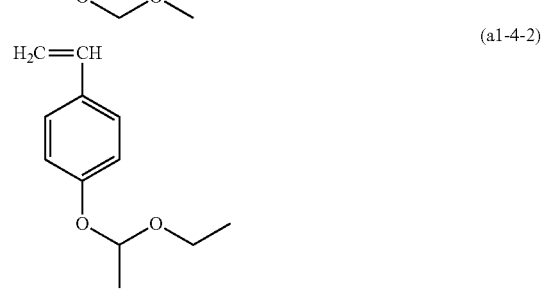

(a1-4-2)

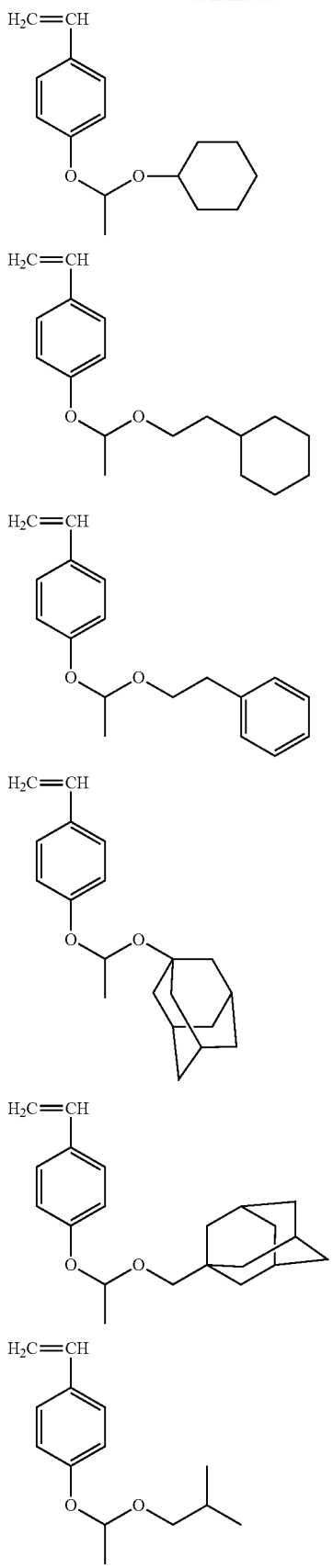

(a1-4-3)

(a1-4-4)

(a1-4-5)

(a1-4-6)

(a1-4-7)

(a1-4-8)

When Resin (A) has a structural unit represented by formula (a1-4), its content is usually 10 to 95% by mole, preferably 15 to 90% by mole and more preferably 20 to 85% by mole based on 100% by mole of all the structural units of the resin.

Other examples of the structural unit having an acid-labile group include one represented by the formula (a1-5).

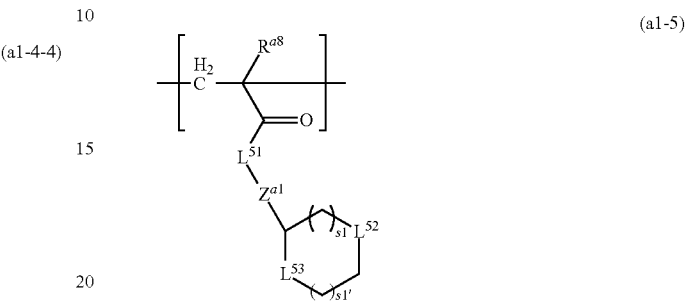

(a1-5)

In formula (a1-5), $R^{a8}$ represents a hydrogen atom, a halogen atom, or a C1-C6 alkyl group which may have a halogen atom, $Z^{a1}$ represents a single bond or *—$(CH_2)_{h3}$—CO-$L^{54}$- in which h3 represents an integer of 1 to 4 and * represents a binding site to $L^{51}$, $L^{51}$, $L^{52}$, $L^{53}$ and $L^{54}$ each independently represent an oxygen atom or a sulfur atom, s1 represents an integer of 1 to 3, and s1' represents an integer of 0 to 3.

Herein, the structural unit represented by formula (a1-5) is sometimes referred to as "structural unit (a1-5)".

Examples of halogen atoms include a fluorine atom and a chlorine atom, preferably a fluorine atom.

Examples of the alkyl group which may have a halogen atom include a methyl group, an ethyl group, n-propyl group, an isopropyl group, an n-butyl group, a sec-butyl group, a tert-butyl group, a pentyl group, a hexyl group, a heptyl group, a 2-ethylhexyl group, an octyl group, a fluoromethyl group, and a trifluoromethyl group.

In the formula (a1-5), $R^{a8}$ preferably represents a hydrogen atom, a methyl group, or a trifluoromethyl group.

$L^{51}$ represents preferably an oxygen atom.

It is preferred that one of $L^{52}$ and $L^{53}$ represents an oxygen atom, while the other represents a sulfur atom.

s1 preferably represents 1. s1' represents an integer of 0 to 2.

$Z^{a1}$ preferably represents a single bond or *—$CH_2$—CO—O— wherein * represents a binding site to $L^{51}$.

Examples of the monomer from which the structural unit (a1-5) is derived include the following ones.

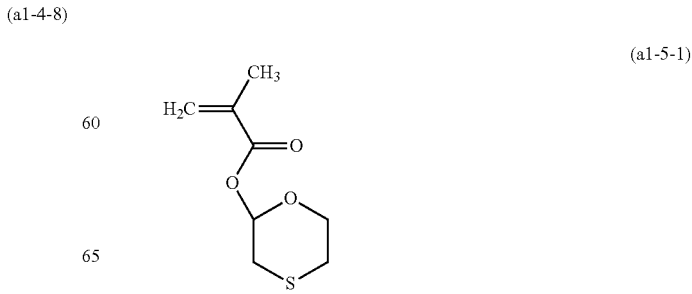

(a1-5-1)

-continued

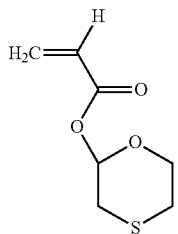
(a1-5-2)

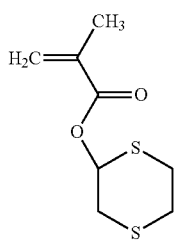
(a1-5-3)

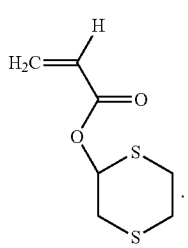
(a1-5-4)

When Resin (A) has a structural unit (a1-5), its content is usually 1 to 50% by mole, preferably 3 to 45% by mole and more preferably 5 to 40% by mole based on 100% by mole of all the structural units of the resin.

Resin (A) has preferably one or more of the structural units (a1-0), (a1-1), (a1-2) and (a1-5), more preferably two or more of these structural units.

Specifically, it has preferably the structural units (a1-1) and (a1-2), the structural units (a1-1) and (a1-5), the structural units (a1-1) and (a1-0), the structural units (a1-5) and (a1-0), the structural units (a1-0), (a1-1) and (a1-2), or the structural units (a1-0), (a1-1) and (a1-5), more preferably the structural units (a1-1) and (a1-2) or the structural units (a1-1) and (a1-5). Resin (A) has preferably the structural unit (a1-1).

The content of the structural unit (a) is usually 10 to 95% by mole, preferably 15 to 90% by mole, and more preferably 20 to 85% by mole based on all the structural units of Resin (A).

The structural unit (s) is derived from a monomer having no acid-labile group.

As to a monomer having no acid-labile group, monomers which have been known to in the art can be used as such monomer, and they are not limited to any specific one provided that it has no acid-labile group.

The structural unit having no acid-labile group preferably has a hydroxyl group or a lactone ring. When the resin (A) has the structural unit derived from the monomer having no acid-labile group and having a hydroxyl group or a lactone ring, a photoresist composition capable of providing a photoresist film with good resolution and adhesiveness of photoresist to a substrate can be obtained.

Hereinafter, the structural unit having no acid-labile group and having a hydroxy group is referred to as "structural unit (a2)", and the structural unit having no acid-labile group and having a lactone ring is referred to as "structural unit (a3)".

The hydroxy group which the structural unit (a2) has may be an alcoholic hydroxy group or a phenolic hydroxy group.

When KrF excimer laser (wavelength: 248 nm) lithography system, or a high energy laser such as electron beam and extreme ultraviolet is used as an exposure system, the resin which has the structural unit (a2) having a phenolic hydroxy group is preferred. When ArF excimer laser (wavelength: 193 nm) is used as an exposure system, the resin which has the structural unit (a2) having an alcoholic hydroxy group is preferred and the resin which has the structural unit (a2-1) described later is more preferred.

Resin (A) may have one or more of the structural units (a2).

Examples of the structural unit (a2) having a phenolic hydroxy group include one represented by the formula (a2-0).

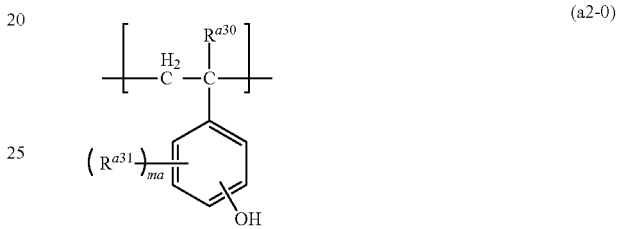
(a2-0)

In formula (a2-0), $R^{a30}$ represents a hydrogen atom, a halogen atom, a C1-C6 alkyl group or a C1 to C6 halogenated alkyl group, $R^{a31}$ is independently in each occurrence a halogen atom, a hydroxyl group, a C1 to C6 alkyl group, a C1 to C6 alkoxy group, a C2 to C4 acyl group, a C2 to C4 acyloxy group, an acryloyl group or a methacryloyl group, "ma" represents an integer of 0 to 4.

In the formula (a2-0), examples of the halogen atom include a fluorine atom, a chlorine atom, a bromine atom or iodine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferred and a C1-C2 alkyl group is more preferred and a methyl group is especially preferred.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferred and a C1-C2 alkoxy group is more preferred and a methoxy group is especially preferred. Examples of the C2-C4 acyl group include an acetyl group, a propyonyl group and a butyryl group, and examples of the C2-C4 acyloxy group include an acetyloxy group, a propyonyloxy group and a butyryloxy group.

In the formula (a2-0), "ma" is preferably 0, 1 or 2, and is more preferably 0 or 1, and especially preferably 0.

Examples of the monomer from which the structural unit (a2-0) is derived include compounds mentioned in JP2010-204634A. Among them, the structural units represented by formulae (a2-0-1), (a2-0-2), (a2-0-3) and (a2-0-4) are preferred as the structural unit represented by formula (a2-0), and those represented by formulae (a2-0-1) and (a2-0-2) are more preferred.

(a2-0-1)
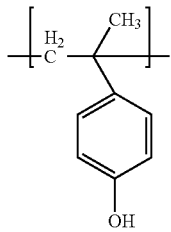

(a2-0-2)
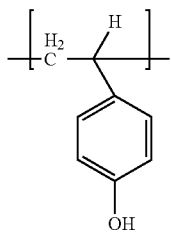

(a2-0-3)
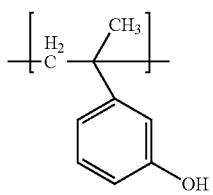

(a2-0-4)
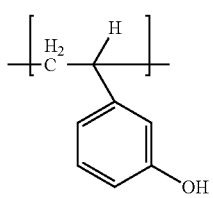

Resin (A) which has a structural unit represented by formula (a2-0) can be produced, for example, by polymerizing a monomer where its phenolic hydroxyl group has been protected with a suitable protecting group, followed by deprotection. Examples of the protecting group for a phenolic hydroxyl group include an acetyl group.

When Resin (A) has the structural unit represented by formula (a2-0), its content is usually 5 to 95% by mole and preferably 10 to 85% by mole and more preferably 15 to 80% by mole based on all the structural units of the resin.

Examples of the structural unit (a2) having an alcoholic hydroxy group include one represented by the formula (a2-1):

(a2-1)
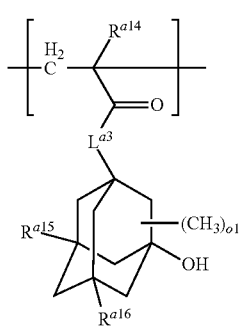

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding site to —CO—, and k2 represents an integer of 1 to 7, and "o1" represents an integer of 0 to 10. Hereinafter, the structural unit represented by formula (a2-1) is referred to as "structural unit (a2-1)".

In the formula (a2-1), $R^{a16}$ is preferably a methyl group. $R^{15}$ is preferably a hydrogen atom. $R^{a16}$ is preferably a hydrogen atom or a hydroxyl group. $L^{a3}$ is preferably *—O— or *—O—$(CH_2)_{f2}$—CO—O— in which * represents a binding site to —CO—, and "f2" represents an integer of 1 to 4, is more preferably *—O— and *—O—$CH_2$—CO—O—, and is still more preferably *—O—, and "o1" is preferably 0, 1, 2 or 3 and is more preferably 0 or 1.

Examples of monomers from which the structural unit represented by formula (a2-1) is derived include compounds mentioned in JP2010-204646A.

Preferred examples of the monomer from which the structural unit represented by formula (a2-1) is derived include those represented by formulae (a2-1-1) to (a2-1-6).

(a2-1-1)
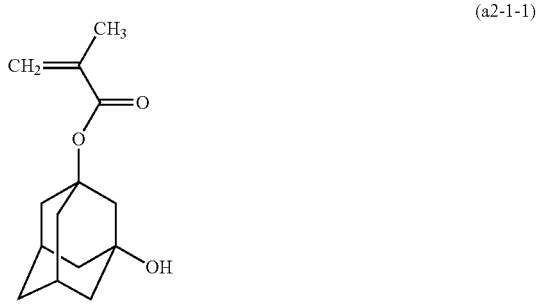

(a2-1-2)
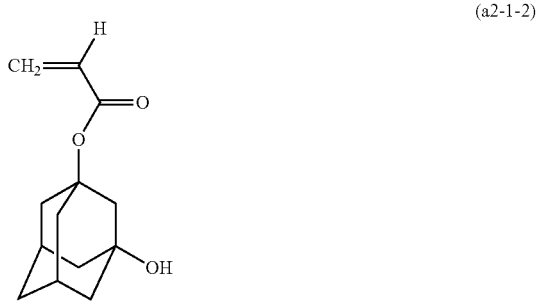

(a2-1-3)
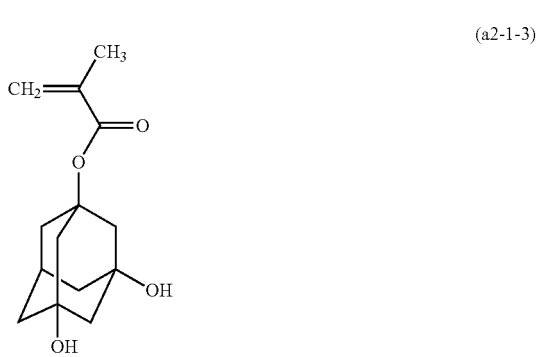

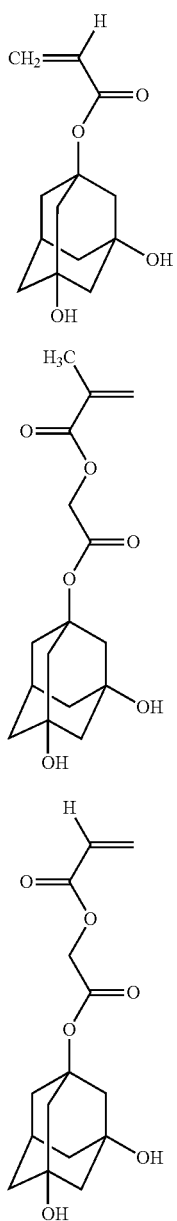
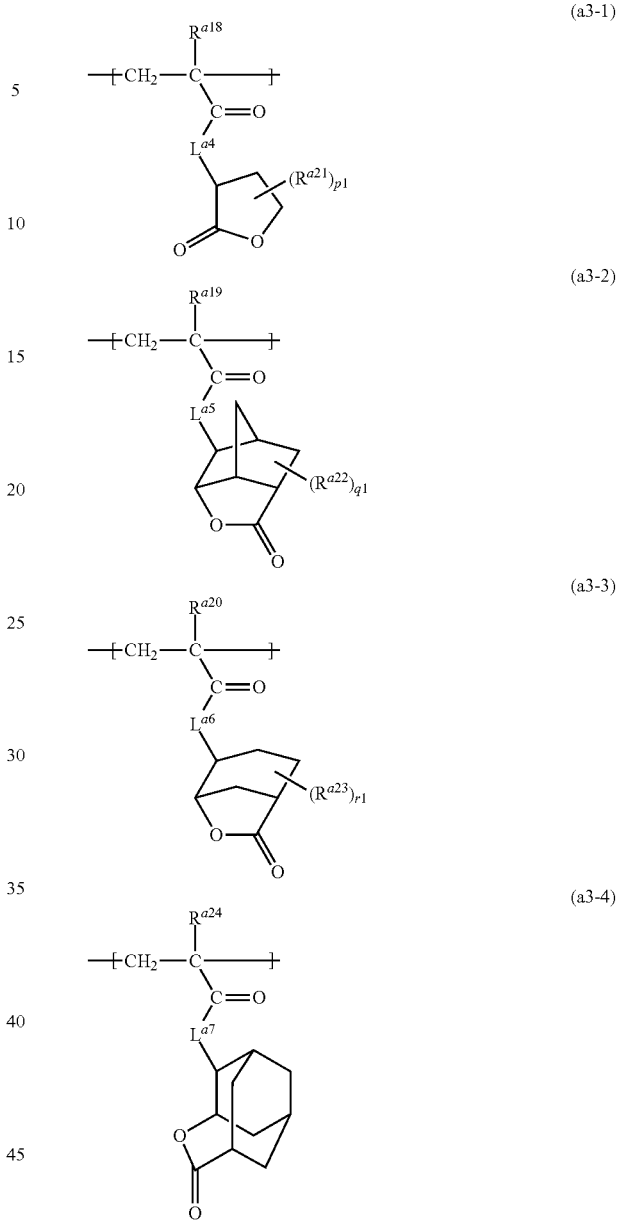

Among them, more preferred are the monomer represented by formulae (a2-1-1), (a2-1-2), (a2-1-3) and (a2-1-4), still more preferred are the monomers represented by formulae (a2-1-1) and (a2-1-3).

When Resin (A) has the structural unit (a2-1), its content is usually 1 to 45% by mole, preferably 1 to 40% by mole, and more preferably 1 to 35% by mole, and especially preferably 2 to 20% by mole, based on all the structural units of the resin.

Examples of the lactone ring contained in the structural unit (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the structural unit (a3) include those represented by the formulae (a3-1), (a3-2), (a3-3) and (a3-4).

In formulae, $L^{a4}$, $L^{a5}$ and $L^{a6}$ each independently represent *—O— or *—O—$(CH_2)_{k3}$—CO—O— in which * represents a binding site to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, $R^{a24}$ each independently represent a hydrogen atom, a halogen atom, or a C1-C6 alkyl group which may have a halogen atom, $L^{a7}$ represents a single bond, $*^1L^{a8}$-O—, $*^1L^{a8}$-CO—O—, $*^1L^{a8}$-CO—O-$L^{a9}$-CO—O— or $*^1$-$L^{a8}$-CO—O—$L^{a9}$-O— in which $L^{a8}$ and $L^{a9}$ each independently represent C1-C6 alkanediyl group, $*^1$ represents a binding site to —CO—, and p1 represents an integer of 0 to 5, q1 and r1 independently each represent an integer of 0 to 3.

Examples of halogen atom represented by $R^{a24}$ include a fluorine atom, a chlorine atom, a bromine atom and an iodine atom.

Examples of the alkyl group represented by $R^{a24}$ include a methyl group, an ethyl group, a propyl group, a butyl group, a pentyl group, and a hexyl group, preferably a C1-C4 alkyl group, and more preferably a methyl group and an ethyl group.

As to $R^{a24}$, examples of the alkyl group having an halogen atom include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a trichloromethyl group, a tribromomethyl group, and a triiodomethyl group.

As to $L^{a8}$ and $L^{a9}$, examples of the alkanediyl group include a methylene group, an ethylene group, a propane-1,3-diyl group, a butane-1,4-diyl group, a pentane-1,5-diyl group and a hexane-1,6-diyl group, a butane-1,3-diyl group, 2-methylpropane-1,3-diyl group, a 2-methylpropane-1,2-diyl group, a pentane-1,4-diyl group and a 2-methylbutane-1,4-diyl group.

It is preferred that $L^{a4}$, $L^{a5}$ and $L^{a6}$ each independently represent *—O— or *—O— $(CH_2)_{d1}$—CO—O— in which * represents a binding site to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group.

It is preferred that p1, q1 and r1 each independently represent an integer of 0 to 2, and it is more preferred that p1, q1 and r1 each independently represent 0 or 1.

$R^{a24}$ is preferably a hydrogen atom or a C1 to C4 alkyl group, more preferably a hydrogen atom, a methyl group or an ethyl group, and still more preferably a hydrogen atom or a methyl group.

$L^{a7}$ represents preferably a single bond or *$^1$-$L^{a8}$-CO—O—, more preferably a single bond, *$^1$—$CH_2$—CO—O— or *$^1$—$C_2H_4$—CO—O—.

Examples of the monomer from which the structural unit (a3) is derived include those mentioned in JP2010-204646A, JP2000-122294A1 and JP2012-41274A1. As the structural unit (a3), preferred are those represented by the formulae (a3-1-1) to (a3-1-4), the formulae (a3-2-1) to (a3-2-4), the formulae (a3-3-1) to (a3-3-4) and the formulae (a3-4-1) to (a3-4-12), more preferred are those represented by the formulae (a3-1-1), (a3-1-2), (a3-2-3), (a3-2-4) and (a3-4-1) to (a3-4-12), still more preferred are those represented by the formulae (a3-4-1) to (a3-4-12), and further still more preferred are those represented by the formulae (a3-4-1) to (a3-4-6).

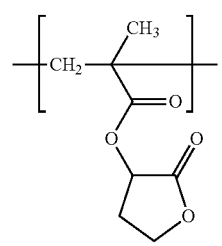

(a3-1-1)

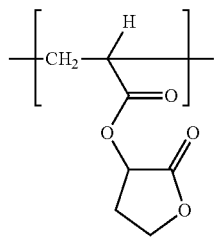

(a3-1-2)

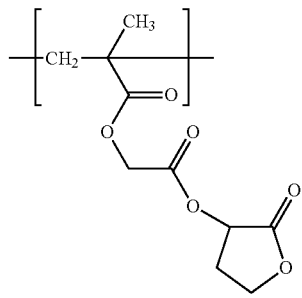

(a3-1-3)

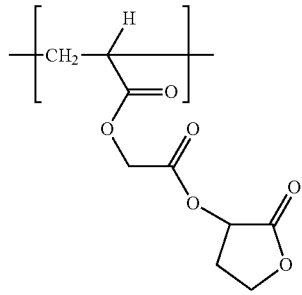

(a3-1-4)

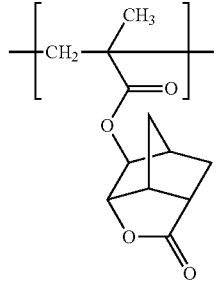

(a3-2-1)

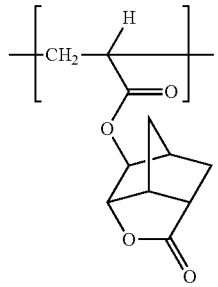

(a3-2-2)

(a3-2-3)
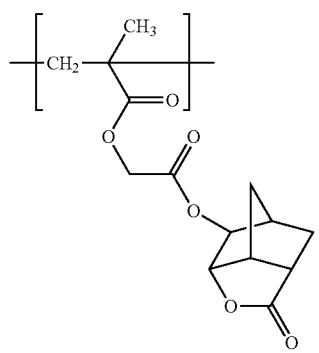
(a3-2-4)
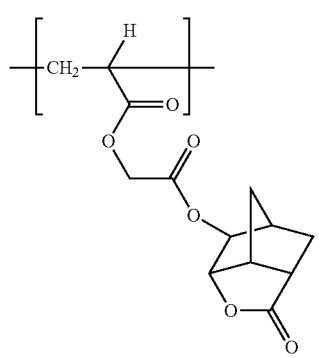
(a3-3-1)
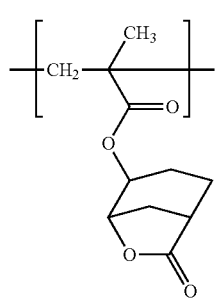
(a3-3-2)
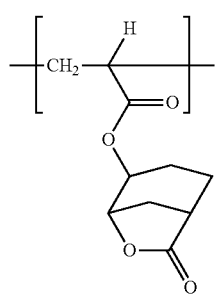
(a3-3-3)
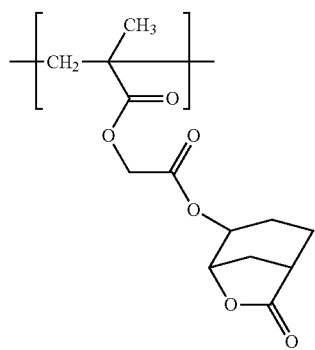
(a3-3-4)
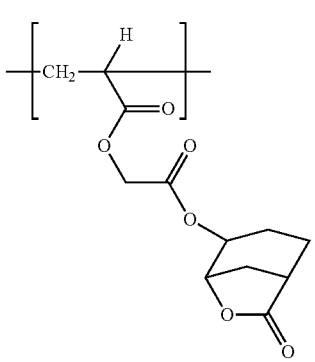
(a3-4-1)
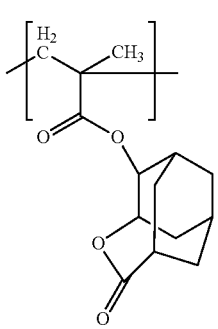
(a3-4-2)
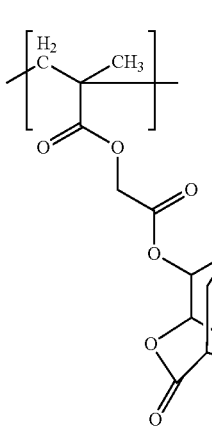
(a3-4-3)
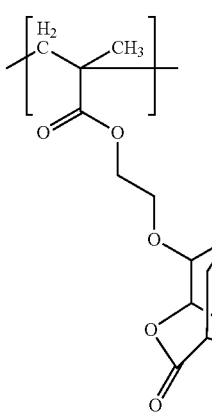

(a3-4-4) 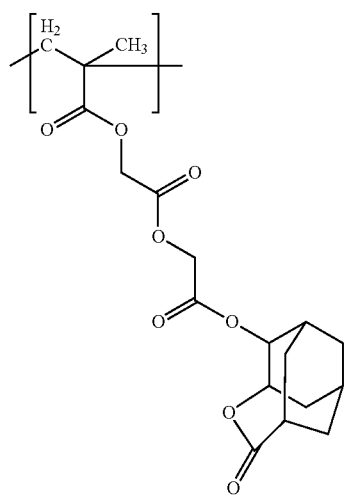
(a3-4-5) 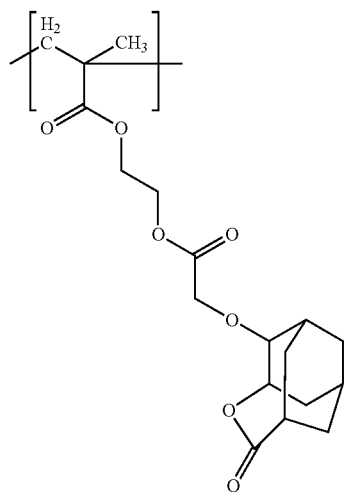
(a3-4-6) 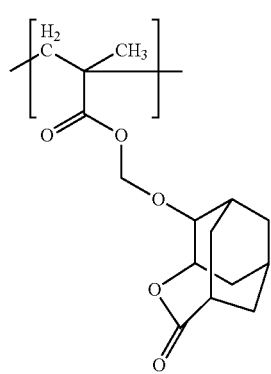
(a3-4-7) 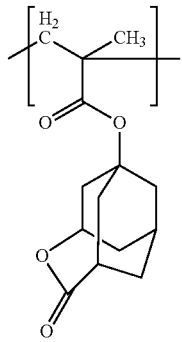
(a3-4-8) 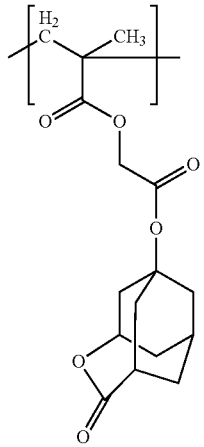
(a3-4-9) 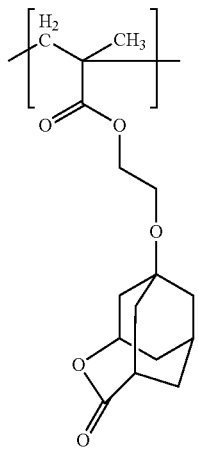

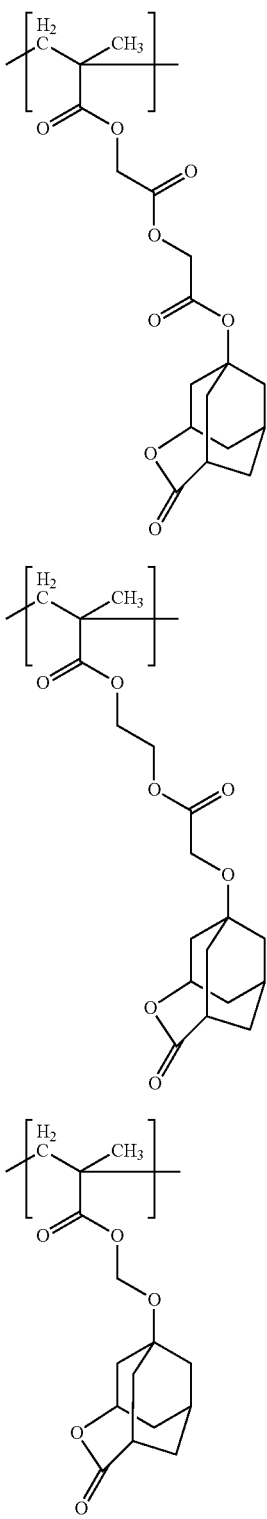

(a3-4-10)

(a3-4-11)

(a3-4-12)

Specific examples of the structural unit (a3) include those where methyl groups of formulae (a3-4-1) to (a3-4-6) have been replaced by hydrogen atoms.

When Resin (A) has the structural unit (a3), its content thereof is preferably 5 to 70% by mole, and more preferably 10 to 65% by mole and more preferably 10 to 60% by mole, based on all the structural units of the resin.

When Resin (A) has the structural unit represented by formula (a3-1), (a3-2), (a3-3) or (a3-4), the total content of them is preferably 5 to 60% by mole, and more preferably 5 to 50% by mole and more preferably 10 to 50% by mole, based on all the structural units of the resin.

Examples of another structural unit having no acid-labile group include a structural unit having a halogen atom and a structural unit which has a hydrocarbon not being removed therefrom by action of an acid.

Examples of the structural unit having a halogen atom, which is sometimes referred to as "structural unit (a4)", include a structural unit represented by formula (a4-0).

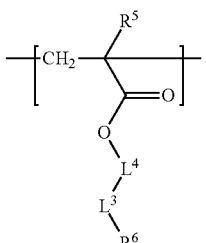

(a4-0)

In the formula (a4-0), $R^5$ represents a hydrogen atom or a methyl group, $L^4$ represents a single bond or a C1 to C4 saturated aliphatic hydrocarbon group, $L^3$ represents a C1 to C8 perfluoroalkanediyl group, or a C3 to C12 perfluorocycloalkanediyl group, and $R^6$ represents a hydrogen atom or a fluorine atom.

Examples of the saturated aliphatic hydrocarbon group for $L^4$ include C1-C4 alkanediyl group, i.e., a linear alkanediyl group such as methylene, ethylene, propane-1,3-diyl, butane-1,4-diyl; and a branched alkanediyl group such as ethane-1,1-diyl, propane-1,2-diyl, butane-1,3-diyl, 2-methylpropane-1,3-diyl and 2-methylpropane-1,2-diyl groups.

$L^4$ is preferably a single bond, methylene or ethylene group, and more preferably a single bond or methylene group.

Examples of the perfluoroalkanediyl group for $L^3$ include difluoromethylene, perfluoroethylene, perfluoroethyl fluoromethylene, perfluoropropane-1,3-diyl, a perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluorocycloalkanediyl group for $L^3$ include perfluorocyclohexanediyl, perfluorocyclopentanediyl, perfluorocycloheptanediyl and perfluoroadamantanediyl groups.

$L^3$ is preferably a C1 to C6 perfluoroalkanediyl group, more preferably a C1 to C3 perfluoroalkanediyl group.

Examples of the structural unit represented by formula (a4-0) include those as follow.

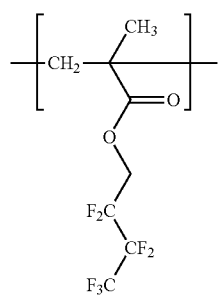 (a4-0-1)
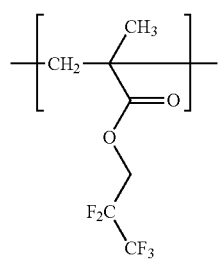 (a4-0-2)
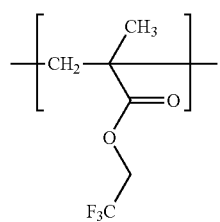 (a4-0-3)
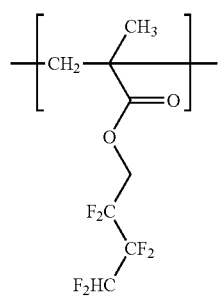 (a4-0-4)
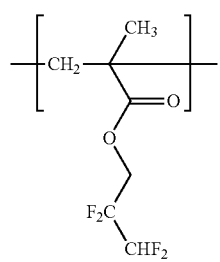 (a4-0-5)
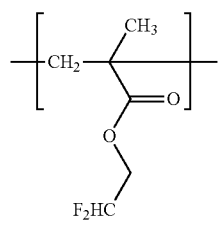 (a4-0-6)
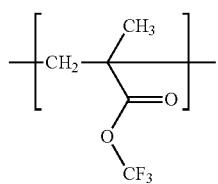 (a4-0-7)
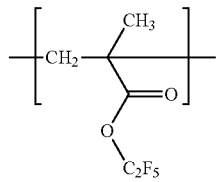 (a4-0-8)
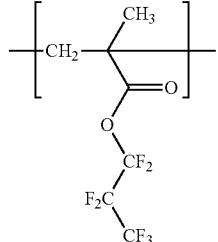 (a4-0-9)
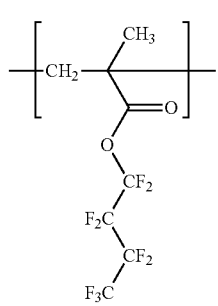 (a4-0-10)
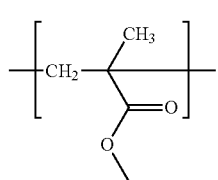 (a4-0-11)
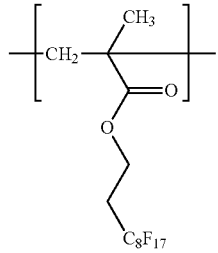
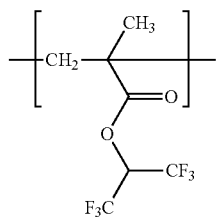 (a4-0-12)

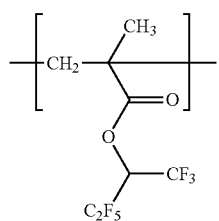
(a4-0-13)
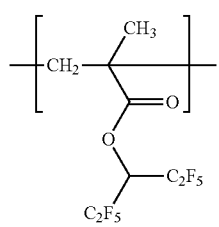
(a4-0-14)
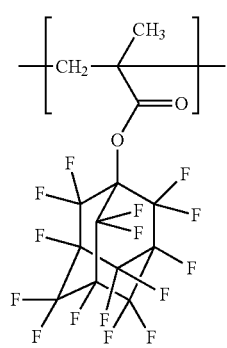
(a4-0-15)
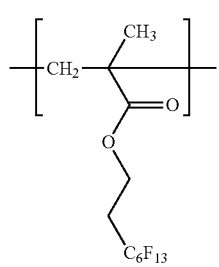
(a4-0-16)
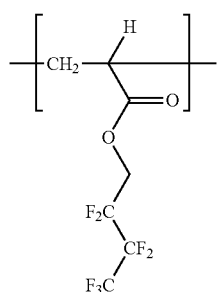
(a4-0-17)
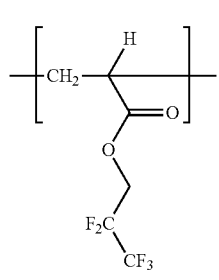
(a4-0-18)
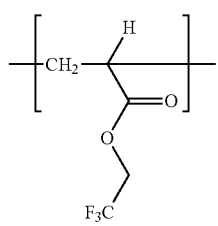
(a4-0-19)
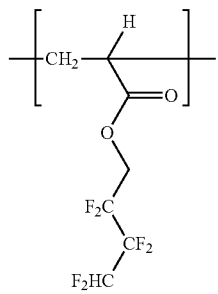
(a4-0-20)
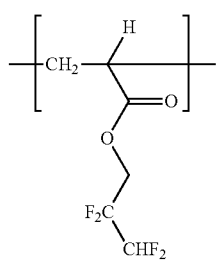
(a4-0-21)
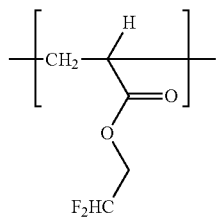
(a4-0-22)
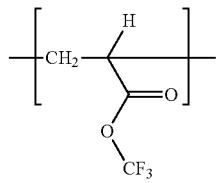
(a4-0-23)
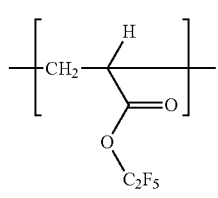
(a4-0-24)

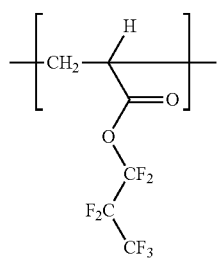
(a4-0-25)

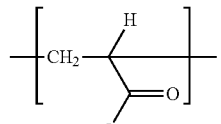
(a4-0-26)

(a4-0-27)

(a4-0-28)

(a4-0-29)

(a4-0-30)

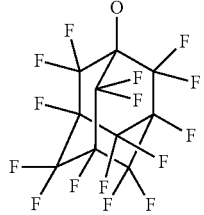
(a4-0-31)

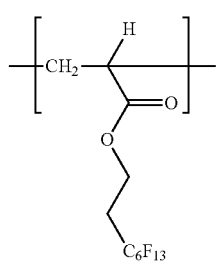
(a4-0-32)

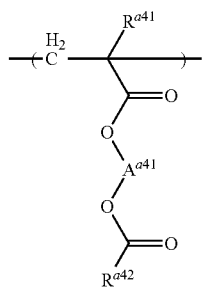

Examples of the structural unit (a4) include those represented by formula (a4-1):

(a4-1)

wherein $R^{a41}$ represents a hydrogen atom or a methyl group, $R^{a42}$ represents an optionally substituted C1-C20 hydrocarbon group where a methylene group can be replaced by an oxygen atom or a carbonyl group, and $A^{a41}$ represents an optionally substituted C1-C6 alkanediyl group or a group represented by formula (a-g1):

$$**—A^{a42}{-}(X^{a41}{-}A^{a43})_{s}{-}X^{a42}{-}A^{a44}{-}*$$ (a-g1)

wherein "s" represents 0 or 1, $A^{a42}$ and $A^{a44}$ each independently represent an optionally substituted C1-5 aliphatic hydrocarbon group, $A^{a43}$ represents a single bond or an optionally substituted $C_1$ to $C_5$ aliphatic hydrocarbon group, and $X^{a41}$ and $X^{a42}$ each independently represent —O—, —CO—, —CO—O— or —O—CO—, provided that the total number of the carbon atoms contained in the group of $A^{a42}$, $A^{a43}$, $A^{a44}$, $X^{a41}$ and $X^{a42}$ is 7 or less, at least one of $A^{a41}$ and $R^{a42}$ has a halogen atom as a substituent, and

* and ** represent a binding site, and * represents a binding site to —O—CO—$R^{a42}$.

The hydrocarbon group for $R^{a42}$ may be a chain aliphatic hydrocarbon group, a cyclic aliphatic hydrocarbon group, an aromatic hydrocarbon group and a combination thereof.

The chain aliphatic hydrocarbon group and the cyclic aliphatic hydrocarbon group may have a carbon-carbon unsaturated bond, and is preferably a chain saturated aliphatic hydrocarbon group and a cyclic saturated aliphatic hydrocarbon group. Examples of the saturated aliphatic hydrocarbon group include a linear or branched alkyl group, a monocyclic or polycyclic alicyclic hydrocarbon group, and an aliphatic hydrocarbon group formed by combining the alkyl group and the alicyclic hydrocarbon group.

Examples of the chain aliphatic hydrocarbon group include an alkyl group such as methyl, ethyl, propyl, butyl, pentyl, hexyl, heptyl, octyl, decyl, dodecyl and hexadecyl groups.

Examples of the alicyclic hydrocarbon group include a cycloalkyl group such as cyclopentyl, cyclohexyl, cycloheptyl, cyclooctyl groups; and polycyclic hydrocarbon groups such as decahydronaphtyl, adamantyl and norbornyl groups as well as groups below. * represents a binding site.

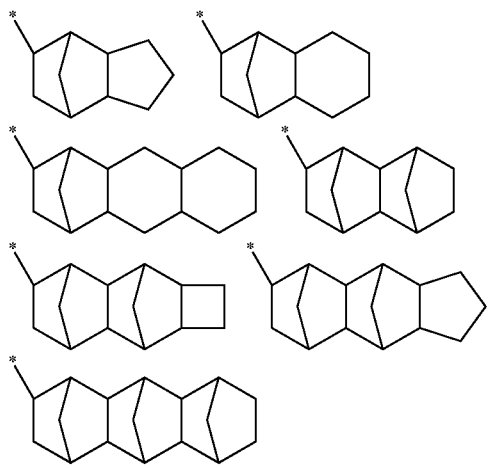

Examples of the aromatic hydrocarbon group include an aryl group such as phenyl, naphthyl, anthryl, biphenyl, phenanthryl and fluorenyl groups.

The hydrocarbon group for $R^{a42}$ is preferably a chain saturated aliphatic hydrocarbon group, a cyclic aliphatic hydrocarbon group, and a combination thereof. The hydrocarbon group may have a carbon-carbon unsaturated bond, is preferably a chain and a cyclic saturated aliphatic hydrocarbon groups, and a combination thereof.

Examples of the substituent for $R^{a42}$ include a halogen atom or a group represented by formula (a-g3):

$$*—X^{a43a}-A^{a45} \quad (a\text{-}g3)$$

wherein $X^{a43}$ represent an oxygen atom, a carbonyl group, a carbonyloxy group or an oxycarbonyl group, $A^{a45}$ represents a C1-C17 aliphatic hydrocarbon group that has a halogen atom, and

* represents a binding site.

Examples of the halogen atom include a fluorine atom, a chlorine atom, a bromine atom and an iodine atom, and preferably a fluorine atom.

Examples of the aliphatic hydrocarbon group for $A^{a45}$ include the same ones as those for $R^{a42}$.

$R^{a42}$ is preferably an aliphatic hydrocarbon group that may have a halogen atom, and more preferably an alkyl group having a halogen atom and/or an aliphatic hydrocarbon group having the group represented by the formula (a-g3).

When $R^{a42}$ is an aliphatic hydrocarbon group having a halogen atom, an aliphatic hydrocarbon group having a fluorine atom is preferred, a perfluoroalkyl group or a perfluorocycloalkyl group are more preferred, a $C_1$ to $C_6$ perfluoroalkyl group is still more preferred, a $C_1$ to $C_3$ perfluoroalkyl group is particularly preferred.

Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

When $R^{a42}$ is an aliphatic hydrocarbon group having the group represented by the formula (a-g3), the total number of the carbon atoms contained in the aliphatic hydrocarbon group including the group represented by the formula (a-g3) is preferably 15 or less, more preferably 12 or less. The number of the group represented by the formula (a-g3) is preferably one when the group represented by the formula (a-g3) is the substituent.

The aliphatic hydrocarbon group having the group represented by the formula (a-g3) is more preferably a group represented by formula (a-g2):

$$*-A^{a46}-X^{a44}-A^{a47} \quad (a\text{-}g2)$$

wherein $A^{a46}$ represents a C1-C17 aliphatic hydrocarbon group that may have a halogen atom, $X^{a44}$ represent a carbonyloxy group or an oxycarbonyl group, $A^{a47}$ represents a C1 to C17 aliphatic hydrocarbon group that may have a halogen atom, provided that the total number of the carbon atoms contained in the group of $A^{a46}$, $X^{a44}$ and $A^{a47}$ is 18 or less, at least one of $A^{a46}$ and $A^{a47}$ has a halogen atom, and

* represents a binding site to a carbonyl group.

The aliphatic hydrocarbon group for $A^{a46}$ has preferably 1 to 6 carbon atoms, more preferably 1 to 3 carbon atoms.

The aliphatic hydrocarbon group for $A^{a47}$ has preferably 4 to 15 carbon atoms, more preferably 5 to 12 carbon atoms. $A^{a47}$ is more preferably a cyclohexyl group or an adamantyl group.

Preferred examples of $*-A^{a46}-X^{a44}-A^{a47}$ include the following ones.

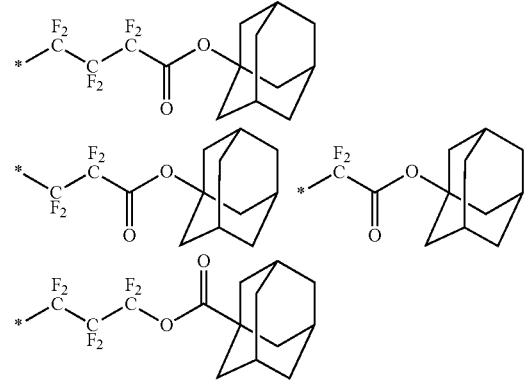

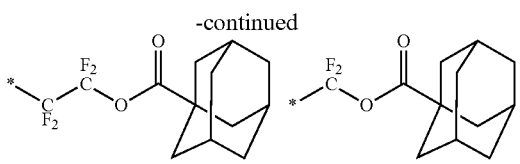
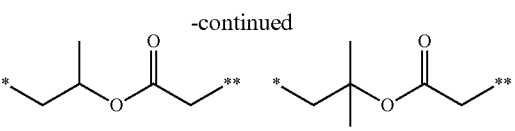

Examples of the alkanediyl group for $A^{a41}$ include a linear alkanediyl group such as methylene, ethylene, propane-1,3-diyl, butane-1,4-diyl, pentane-1,5-diyl and hexane-1,6-diyl groups;

a branched alkanediyl group such as propane-1,2-diyl, butan-1,3-diyl, 2-methylpropane-1,2-diyl, 1-methylbutane-1,4-diyl, 2-methylbutane-1,4-diyl groups.

Examples of the substituent on the alkanediyl group for $A^{a41}$ include a hydroxy group and a C1 to C6 alkoxy group.

$A^{a41}$ is preferably a C1 to C4 alkanediyl group, more preferably a C2 to C4 alkanediyl group, and still more preferably an ethylene group.

In the group represented by the formula (a-g1) (which is sometimes referred to as "group (a-g1)"), examples of the aliphatic hydrocarbon group for $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent on the aliphatic hydrocarbon group for $A^{a}42$, $A^{a43}$ and $A^{a44}$ include a hydroxy group and a C1-C6 alkoxy group.

s is preferably 0.

Examples of the group (a-g1) in which $X^{a42}$ represents an oxygen atom, a carbonyl group, a carbonyloxy group, or an oxycarbonyl group include the following ones. In the formula, * and  each represent a binding site, and  represents a binding site to —O—CO—$R^{a42}$.

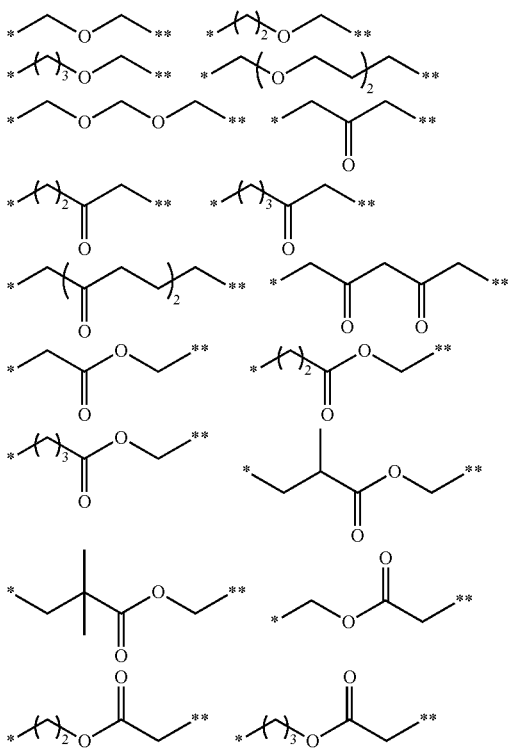

The structural unit represented by the formula (a4-1) is preferably structural units represented by formula (a4-2) and formula (a4-3):

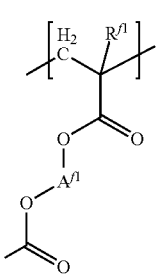

(a4-2)

wherein $R^{f1}$ represents a hydrogen atom or a methyl group, $A^{f1}$ represent a C1-C16 alkanediyl group, and $R^{f2}$ represents a C1-C10 hydrocarbon group that has a fluorine atom;

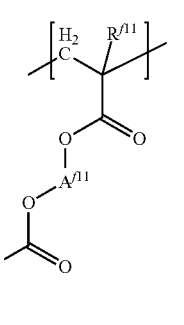

(a4-3)

where $R^{f11}$ represents a hydrogen atom or a methyl group, $A^{f11}$ represent a C1 to C6 alkanediyl group, $A^{f13}$ represents a C1 to C18 aliphatic hydrocarbon group that may have a fluorine atom, $X^{f12}$ represents an oxycarbonyl group or a carbonyloxy group, $A^{f14}$ represents a C1 to C17 aliphatic hydrocarbon group that may have a fluorine atom, and provided that at least one of $A^{f13}$ and $A^{f14}$ represents an aliphatic hydrocarbon group having a fluorine atom.

Examples of the alkanediyl group for $A^{f1}$ include a linear alkanediyl group such as methylene, ethylene, propane-1,3-diyl, propane-1,2-diyl, butane-1,4-diyl, pentane-1,5-diyl and hexane-1,6-diyl groups; and a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

The hydrocarbon group for $R^{f2}$ includes an aliphatic hydrocarbon group and an aromatic hydrocarbon group. The aliphatic hydrocarbon group includes chain and cyclic groups, and a combination thereof.

The aliphatic hydrocarbon group is preferably an alkyl group and a cyclic aliphatic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups. Examples of the polycyclic hydrocarbon groups includes decahydronaphthyl, adamantyl, 2-alkyladamantane-2-yl, 1-(adamantane-1-yl)alkane-1-yl, norbornyl, methylnorbornyl and isobornyl groups.

Examples of the hydrocarbon group having a fluorine atom for $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodeca fluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $A^{f1}$ is preferably a C2-C4 alkanediyl group, and more preferably an ethylene group.

$R^{f2}$ is preferably a C1-C6 fluorinated alkyl group.

Examples of the alkanediyl group for $A^{f11}$ include the same ones as those for $A^{f1}$.

Examples of the aliphatic hydrocarbon group for $A^{f13}$ include any of a divalent chain or cyclic aliphatic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f13}$ is preferably the saturated aliphatic hydrocarbon group that may have a fluorine atom, and more preferably perfluoroalkandiyl group.

Examples of the divalent chain aliphatic hydrocarbon that may have a fluorine atom include an alkanediyl group such as methylene, ethylene, propanediyl, butanediyl and pentanediyl groups; a perfluoroalkanediyl group such as difluoromethylene, perfluoroethylene, perfluoropropanediyl, perfluorobutanediyl and perfluoropentanediyl groups.

The divalent cyclic aliphatic hydrocarbon group that may have a fluorine atom is any of a monocyclic group and a polycyclic group.

Examples of the monocyclic aliphatic hydrocarbon group include cyclohexanediyl and perfluorocyclohexanediyl groups. Examples of the polycyclic aliphatic hydrocarbon group include adamantanediyl, norbornanediyl and perfluoroadamantanediyl groups.

Examples of the aliphatic hydrocarbon group for $A^{f14}$ include a chain aliphatic hydrocarbon group, a cyclic aliphatic hydrocarbon group, and a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f14}$ is preferably the saturated aliphatic hydrocarbon group that may have a fluorine atom.

Examples of the chain aliphatic hydrocarbon group that may have a halogen atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, pentyl, hexyl, perfluorohexyl, hepthyl, perfluoroheptyl, octyl and perfluorooctyl groups.

The cyclic aliphatic hydrocarbon group that may have a fluorine atom may be any of a monocyclic hydrocarbon group and a polycyclic hydrocarbon group. Examples of the group containing the monocyclic aliphatic hydrocarbon group include cyclopropylmethyl, cyclopropyl, cyclobutylmethyl, cyclopentyl, cyclohexyl and perfluorocyclohexyl groups. Examples of the group containing the polycyclic aliphatic hydrocarbon group includes adamantyl, adamantylmethyl, norbornyl, norbornylmethyl, perfluoroadamantyl and perfluoroadamantylmethyl groups.

In the formula (a4-3), $A^{f11}$ is preferably an ethylene group. The aliphatic hydrocarbon group for $A^{f13}$ is preferably a C1 to C6 aliphatic hydrocarbon group, more preferably a C2 to C3 aliphatic hydrocarbon group.

The aliphatic hydrocarbon group for $A^{f14}$ is preferably a C3 to C12 aliphatic hydrocarbon group, more preferably a C3 to C10 aliphatic hydrocarbon group. Among these, $A^{f14}$ is preferably a group containing a C3 to C12 alicyclic hydrocarbon group, more preferably cyclopropylmethyl, cyclopentyl, cyclohexyl, norbornyl and adamantyl groups.

Examples of the structural unit represented by formula (a4-2) include structural units represented by formula (a4-1-1) to formula (a4-1-22).

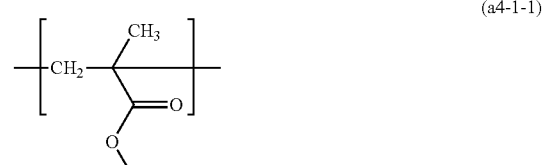

(a4-1-1)

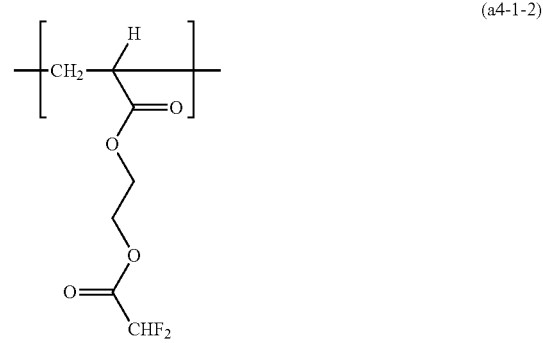

(a4-1-2)

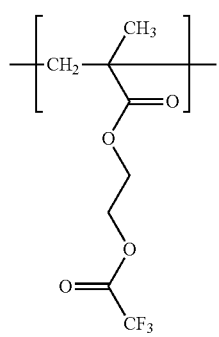
(a4-1-3)
(a4-1-4)
(a4-1-5)
(a4-1-6)
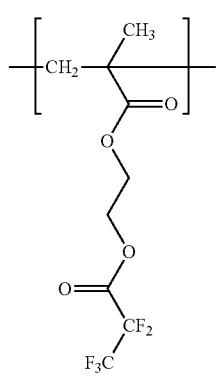
(a4-1-7)
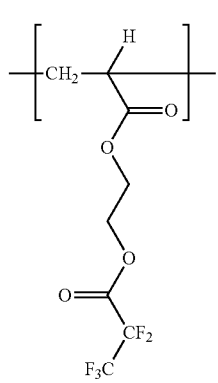
(a4-1-8)
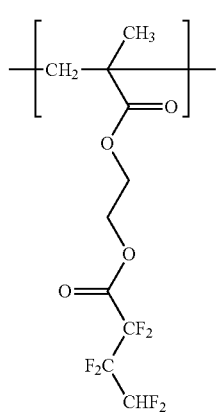
(a4-1-9)
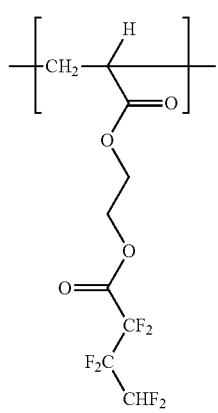
(a4-1-10)

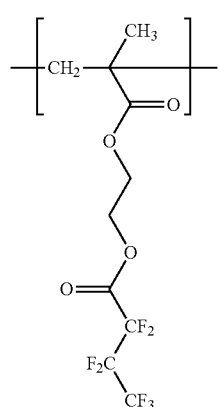
(a4-1-11)
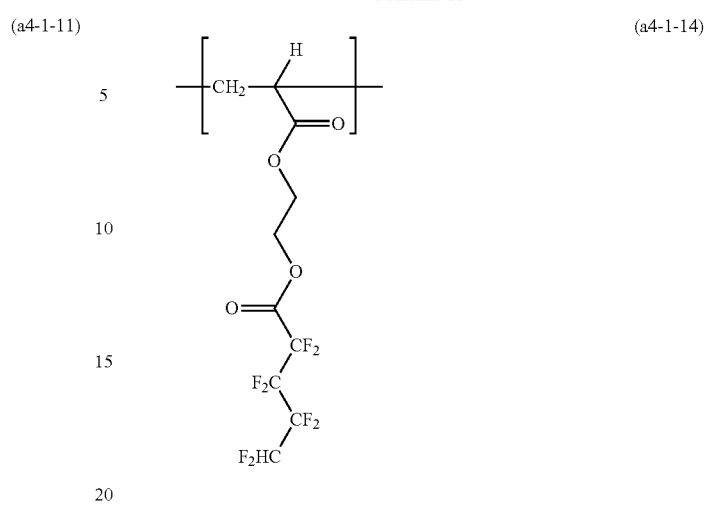
(a4-1-14)
(a4-1-15)
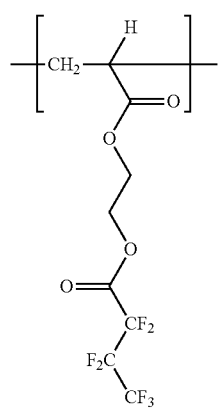
(a4-1-12)
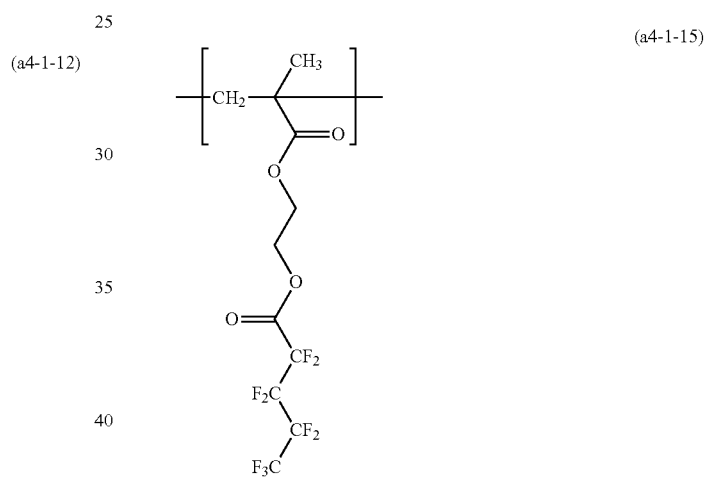
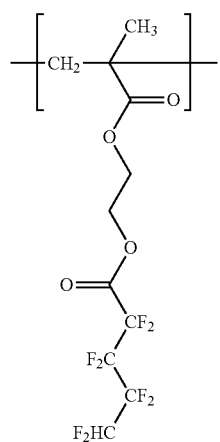
(a4-1-13)
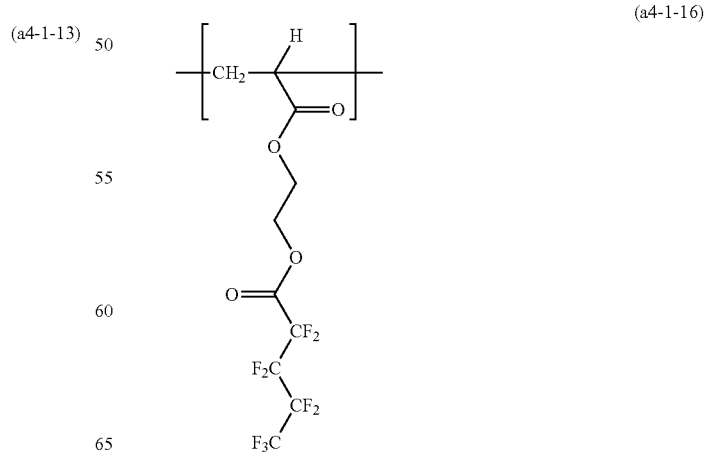
(a4-1-16)

(a4-1-17)
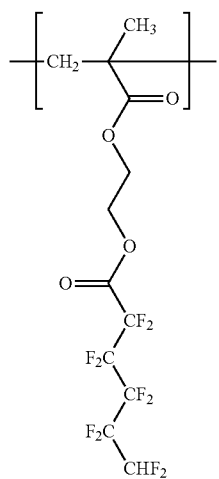
(a4-1-20)
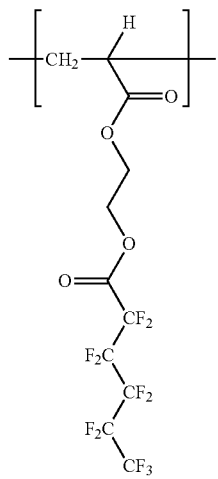
(a4-1-18)
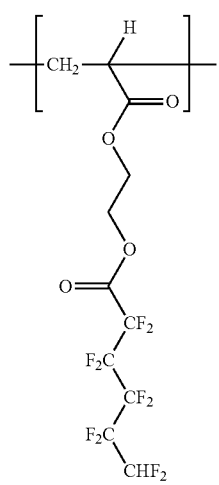
(a4-1-21)
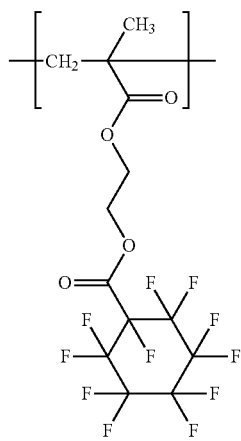
(a4-1-19)
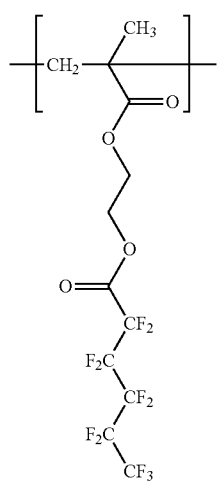
(a4-1-22)
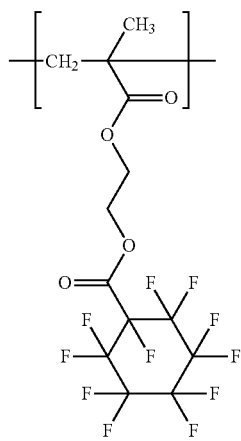
Examples of the structural unit represented by formula (a4-3) include structural units represented by formula (a4-1'-1) to formula (a4-1'-22).

(a4-1'-1) 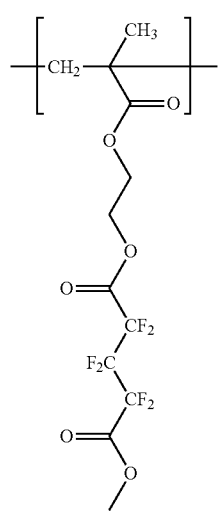
(a4-1'-2) 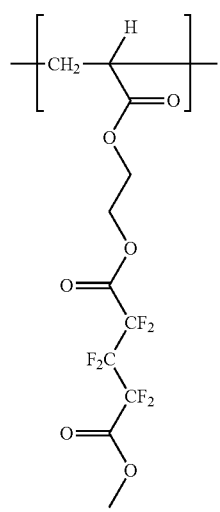
(a4-1'-3) 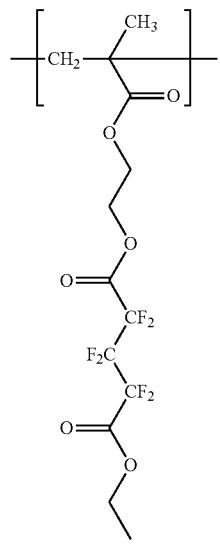
(a4-1'-4) 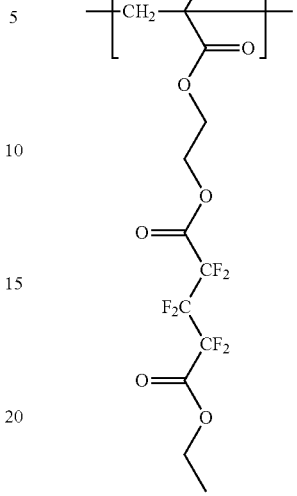
(a4-1'-5) 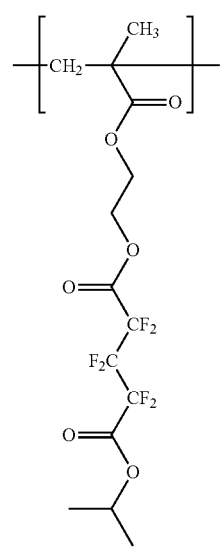
(a4-1'-6) 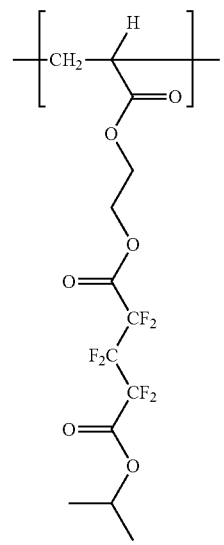

(a4-1'-7)
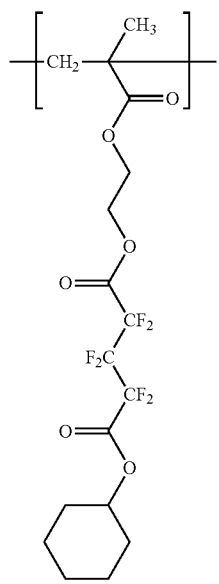
(a4-1'-9)
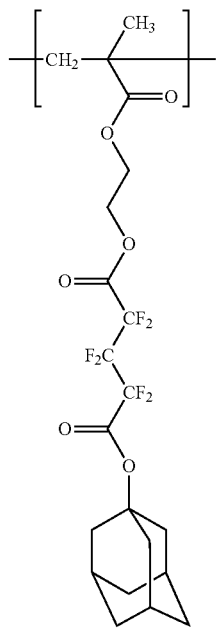
(a4-1'-8)
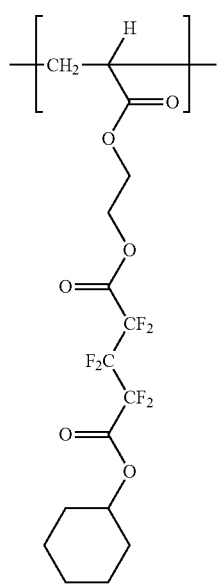
(a4-1'-10)
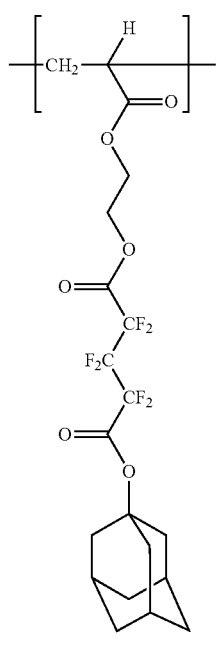

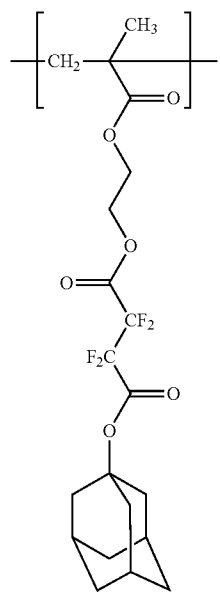
(a4-1′-11)
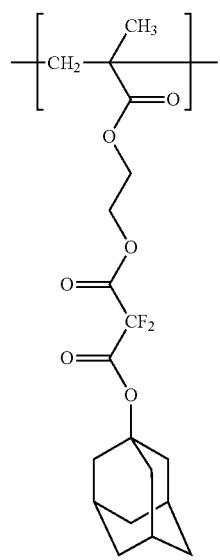
(a4-1′-13)
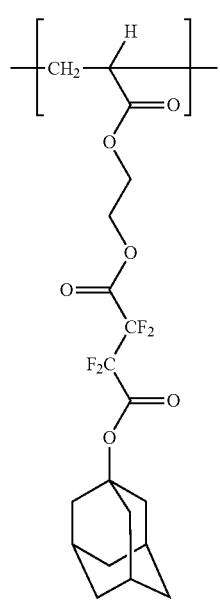
(a4-1′-12)
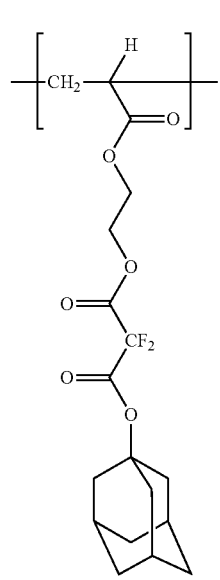
(a4-1′-14)

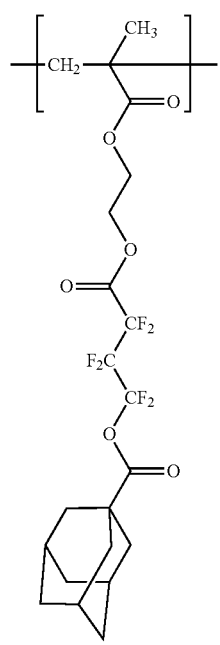 (a4-1'-15)
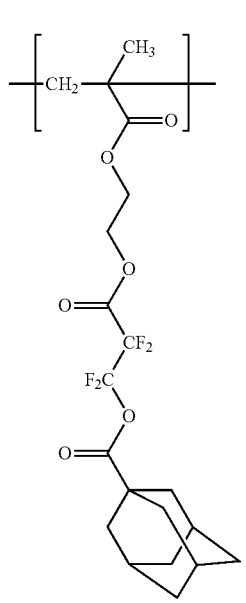 (a4-1'-17)
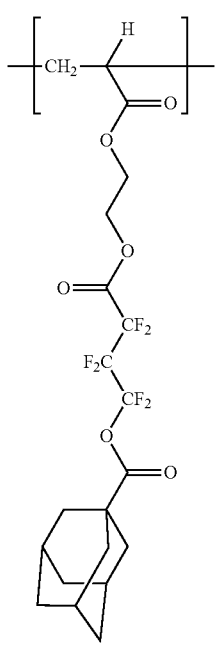 (a4-1'-16)
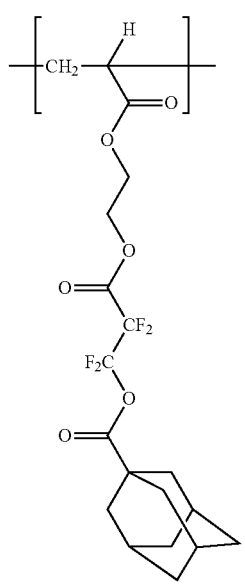 (a4-1'-18)

(a4-1'-19)

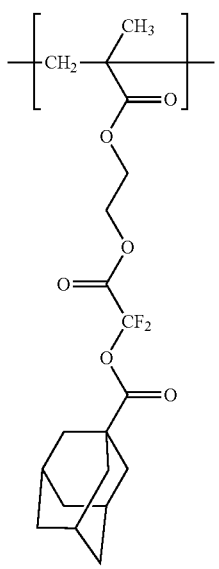

(a4-1'-20)

(a4-1'-21)

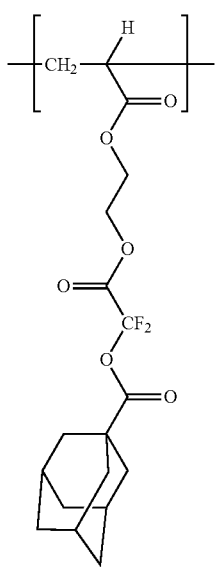

(a4-1'-22)

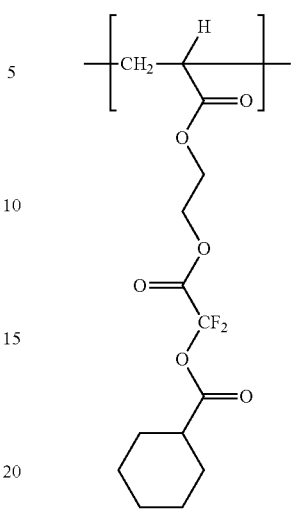

Examples of the structural unit (a4) include a structural unit represented by formula (a4-4):

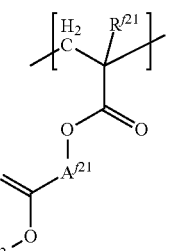

(a4-4)

wherein $R^{/21}$ represents a hydrogen atom or a methyl group, $A^{/21}$ represents *—$(CH_2)_{j1}$—, *—$(CH_2)_{j2}$—O—$(CH_2)_{j3}$— or *—$(CH_2)_{j4}$—CO—O—$(CH_2)_{j5}$—, where * represents a binding site to an oxygen atom, j1 to j5 each independently represents an integer of 1 to 6, and $R^{/22}$ represents a C1 to C10 hydrocarbon group having a fluorine atom.

Examples of the hydrocarbon group having a fluorine atom for $R^{/22}$ include the same ones as those for $R^{/2}$ in the formula (a4-2). $R^{/22}$ is preferably a C1 to C10 alkyl group having a fluorine atom or a C3 to C10 alicyclic hydrocarbon group having a fluorine atom, more preferably a C1 to C10 alkyl group having a fluorine atom, and still more preferably a C1 to C6 alkyl group having a fluorine atom.

In the formula (a4-4), $A^{/21}$ is preferably —$(CH_2)_{j1}$—, more preferably a methylene group or an ethylene group, and still more preferably a methylene group.

Examples of the structural unit represented by the formula (a4-4) include the following ones.

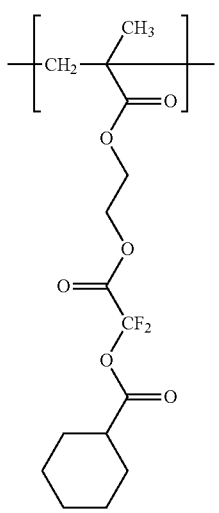

103
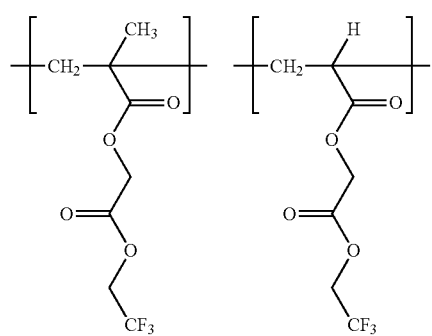
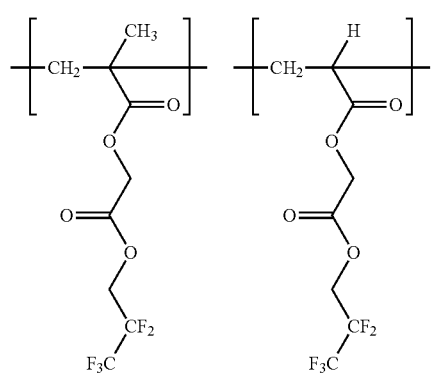
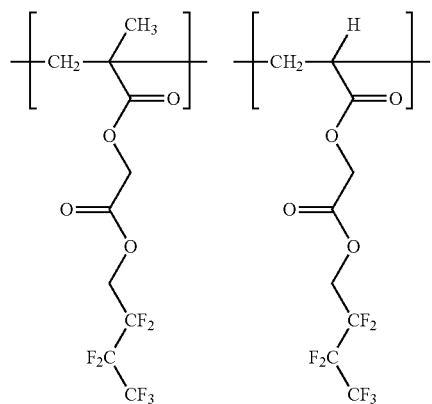
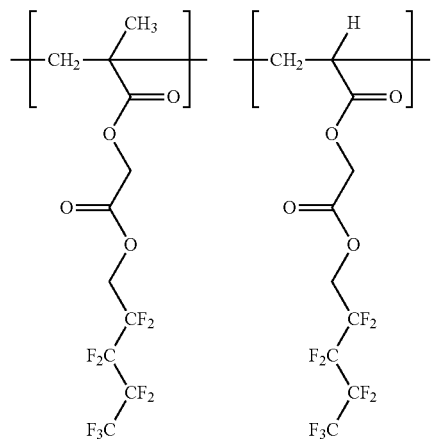
104
-continued
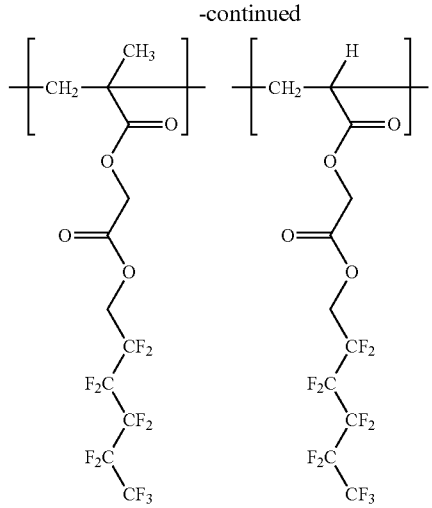
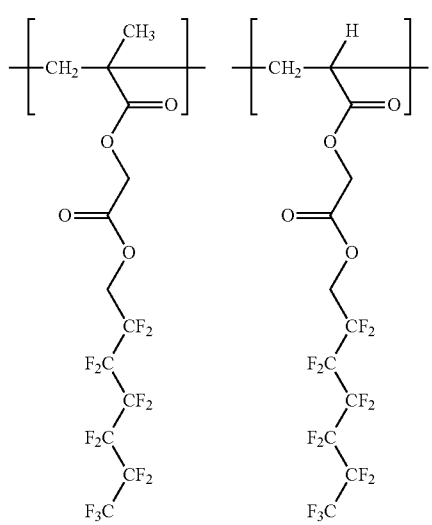
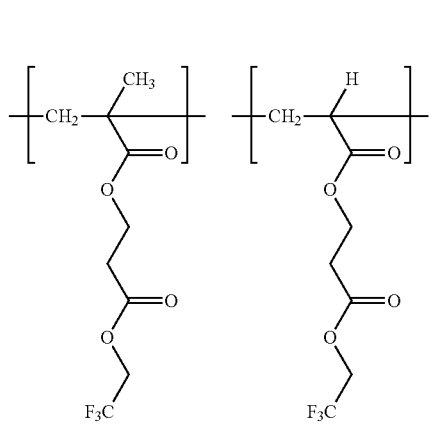

-continued

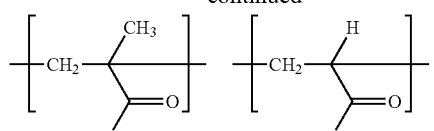

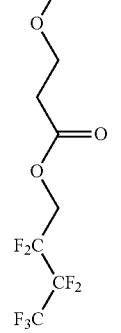

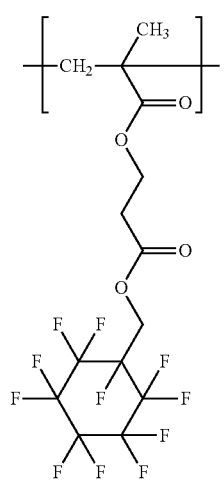
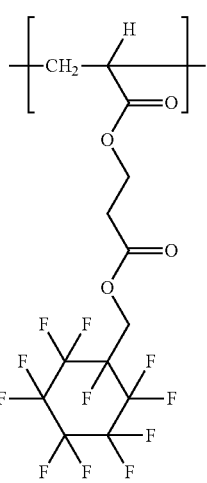

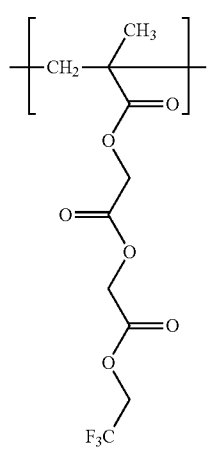
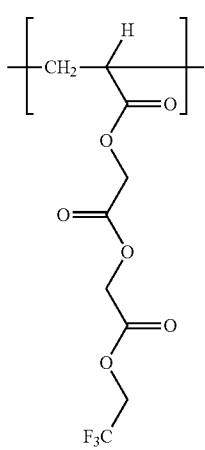

-continued

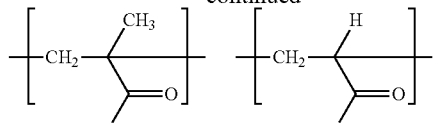

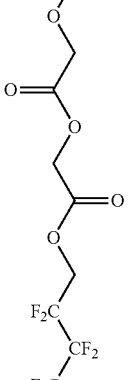

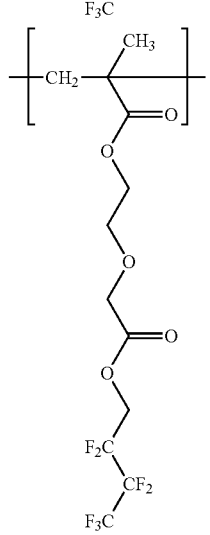
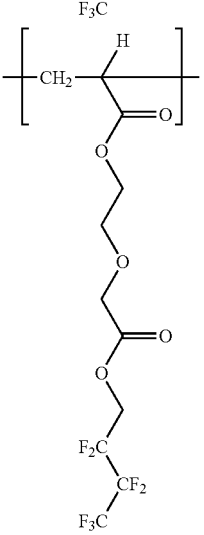

When Resin (A) has the structural unit (a4), the content thereof is usually 1 to 20% by mole, preferably 2 to 15% by mole, and more preferably 3 to 10% by mole, based on all the structural units of the resin.

The structural unit which has a hydrocarbon not being removed therefrom by action of an acid may have a linear, branched or cyclic hydrocarbon, preferably an alicyclic hydrocarbon group.

Examples of the structural unit having a hydrocarbon group not being removed therefrom by action of an acid include one represented by formula (a5-1):

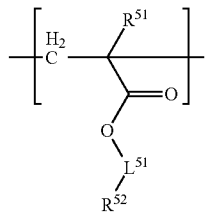

(a5-1)

where $R^{51}$ represents a hydrogen atom or a methyl group;
$R^{52}$ represents a C3 to C18 alicyclic hydrocarbon group, provided that the alicyclic hydrocarbon group has no substituent on the carbon atom bonded to $L^{51}$; and L$^{51}$ represents a single bond or a C1 to C8 alkanediyl group where a methylene group can be replaced by an oxygen atom or carbonyl group.

The alicyclic hydrocarbon group represented by R$^{52}$ may be monocyclic or polycyclic one.

Examples of the alicyclic hydrocarbon group include a monocyclic hydrocarbon group such as a C3 to C18 cycloalkyl group (e.g. a cyclopropyl group, a cyclobutyl group, a cyclopentyl group, and a cyclohexyl group) and a polycyclic alicyclic hydrocarbon group such as an adamantyl group, or a norbornyl group.

Examples of the alicyclic hydrocarbon group having a substituent include a 3-hydroxyadamantyl group, and a 3-methyladamantyl group. Examples of the C1-C8 aliphatic hydrocarbon group include an alkyl group such as methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group having a substituent for R$^{52}$ include 3-hydroxyadamantyl group and 3-methyladamantyl group.

R$^{52}$ is preferably an unsubstituted C3-C18 alicyclic hydrocarbon group, and more preferably an adamantyl, norbornyl or cyclohexyl group.

Examples of the divalent saturated hydrocarbon group for L$^{51}$ include a divalent saturated aliphatic hydrocarbon group and a divalent saturated alicyclic hydrocarbon group, and a divalent saturated aliphatic hydrocarbon group is preferred.

Examples of the divalent saturated aliphatic hydrocarbon group include an alkanediyl group such as methylene, ethylene, propanediyl, butanediyl and pentanediyl groups.

Examples of the divalent saturated alicyclic hydrocarbon group include any of a monocyclic group and a polycyclic group.

Examples of the monocyclic group include a cycloalkanediyl group such as cyclopentanediyl and cyclohexanediyl groups. Examples of the polycyclic group include adamantanediyl and norbornanediyl groups.

Examples of the saturated hydrocarbon group in which a methylene group has been replaced by an oxygen atom or a carbonyl group include groups represented by formula (L1-1) to formula (L1-4). In formula (L1-1) to formula (L1-4), * represents a binding site to an oxygen atom.

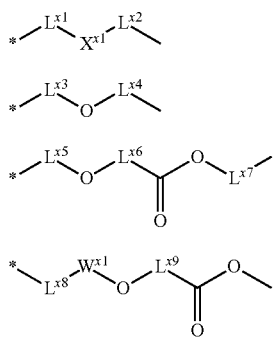

In the formulae, X$^{X1}$ represents an oxycarbonyl group or a carbonyloxy group, L$^{X1}$ represents a C1 to C16 divalent saturated aliphatic hydrocarbon group, L$^{X2}$ represents a single bond or a C1 to C15 divalent saturated aliphatic hydrocarbon group, provided that the total number of the carbon atoms contained in the groups of L$^{X1}$ and L$^{X2}$ is 16 or less;

L$^{X3}$ represents a single bond or a C1 to C17 divalent saturated aliphatic hydrocarbon group, L$^{X4}$ represents a single bond or a C1 to C16 divalent saturated aliphatic hydrocarbon group, provided that the total number of the carbon atoms contained in the groups of L$^{X3}$ and L$^{X4}$ is 17 or less;

L$^{X5}$ represents a C1 to C15 divalent saturated aliphatic hydrocarbon group,

L$^{X6}$ and L$^{X7}$ each independently represent a single bond or a C$_1$ to C$_{14}$ divalent saturated aliphatic hydrocarbon group, provided that the total number of the carbon atoms contained in the groups of L$^{X5}$, L$^{X6}$ and L$^{X7}$ is 15 or less;

L$^{X8}$ and L$^{X9}$ each independently represent a single bond or a C1 to C12 divalent saturated aliphatic hydrocarbon group, W$^{X1}$ represents a C3 to C15 divalent saturated alicyclic hydrocarbon group, provided that the total number of the carbon atoms contained in the groups of L$^{X8}$, L$^{X9}$ and L$^{X1}$ is 15 or less.

L$^{X1}$ is preferably a C1 to C8 divalent saturated aliphatic hydrocarbon group, and more preferably a methylene group or an ethylene group.

L$^{X2}$ is preferably a single bond or a C1 to C8 divalent saturated aliphatic hydrocarbon group, and more preferably a single bond.

L$^{X3}$ is preferably a C1 to C8 divalent saturated aliphatic hydrocarbon group.

L$^{X4}$ is preferably a single bond or a C1 to C8 divalent saturated aliphatic hydrocarbon group.

L$^{X5}$ is preferably a C1 to C8 divalent saturated aliphatic hydrocarbon group, and more preferably a methylene group or an ethylene group.

L$^{X6}$ is preferably a single bond or a C1 to C8 divalent saturated aliphatic hydrocarbon group, and more preferably a methylene group or an ethylene group.

L$^{X7}$ is preferably a single bond or a C1 to C8 divalent saturated aliphatic hydrocarbon group.

L$^{X8}$ is preferably a single bond or a C1 to C8 divalent saturated aliphatic hydrocarbon group, and more preferably a single bond or a methylene group.

L$^{X9}$ is preferably a single bond or a C1 to C8 divalent saturated aliphatic hydrocarbon group, and more preferably a single bond or a methylene group.

W$^{X1}$ is preferably a C3 to C10 divalent saturated alicyclic hydrocarbon group, and more preferably a cyclohexanediyl or adamantanediyl group.

Examples of the group represented by the formula (L1-1) include the following ones.

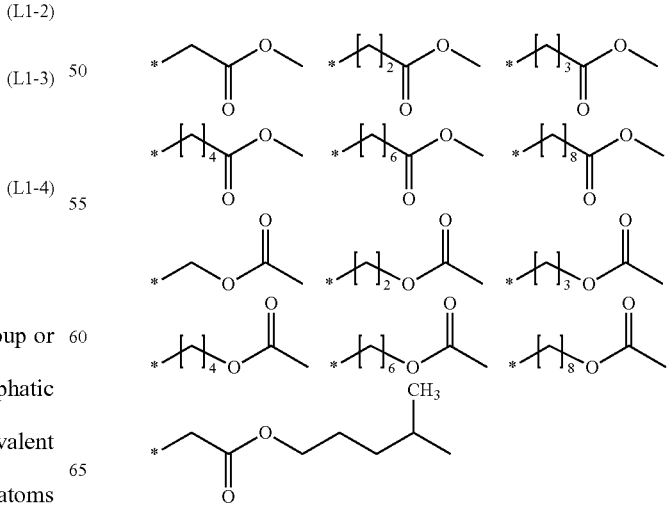

-continued

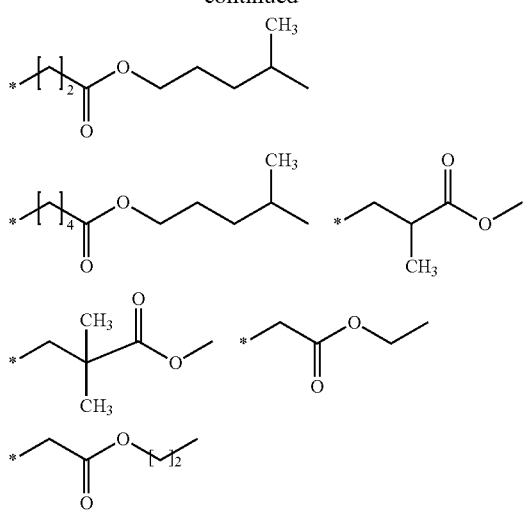

Examples of the group represented by the formula (L1-2) include the following ones.

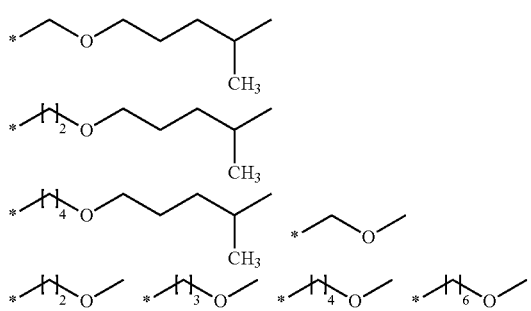

Examples of the group represented by the formula (L1-3) include the following ones.

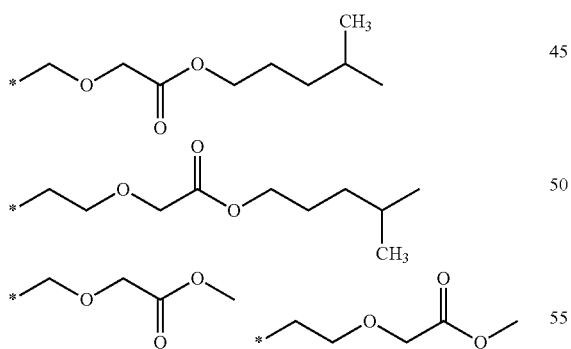

Examples of the group represented by the formula (L1-4) include the following ones.

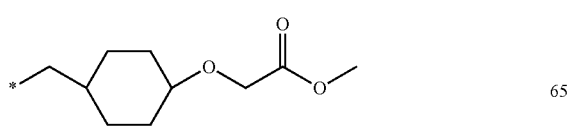

-continued

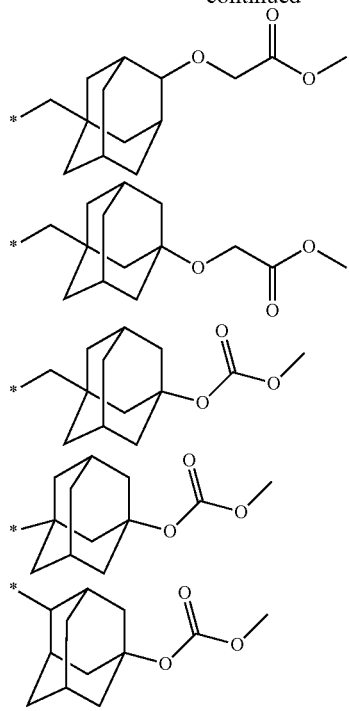

$L^{51}$ is preferably a single bond or the group represented by the formula (L1-1).

Examples of the structural unit represented by formula (a5-1) include the following ones.

(a5-1-1)
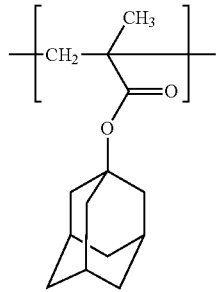

(a5-1-2)
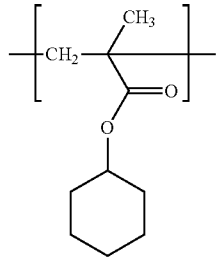

(a5-1-3)
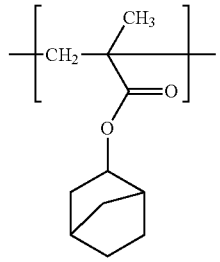

-continued
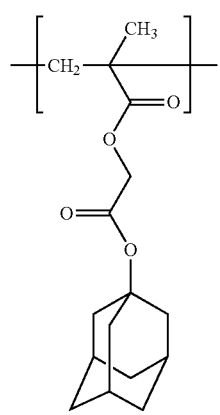
(a5-1-4)
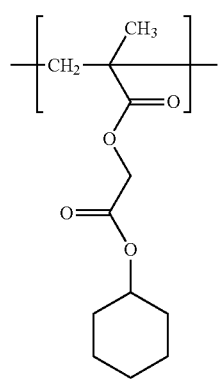
(a5-1-5)
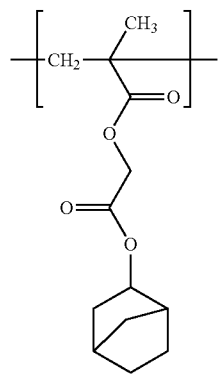
(a5-1-6)
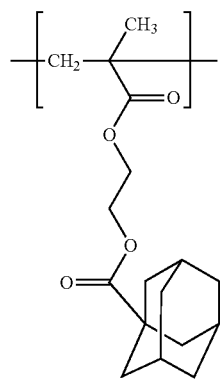
(a5-1-7)
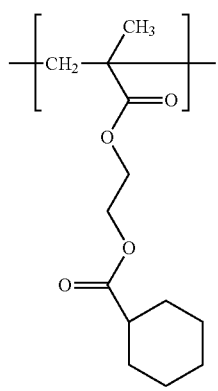
(a5-1-8)
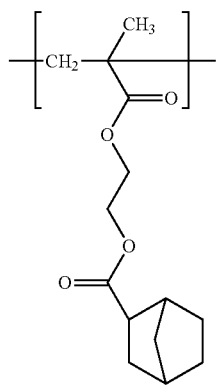
(a5-1-9)
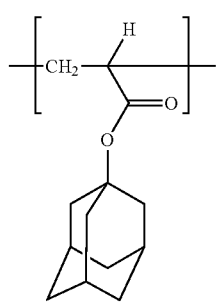
(a5-1-10)
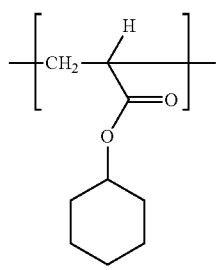
(a5-1-11)
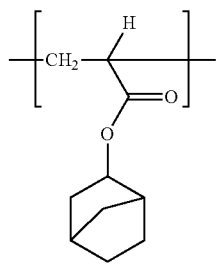
(a5-1-12)

-continued
(a5-1-13) 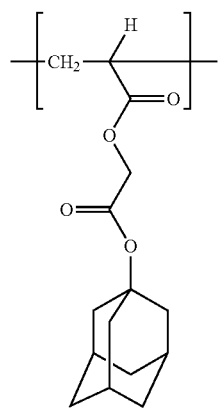
(a5-1-14)
(a5-1-15)
(a5-1-16)
-continued
(a5-1-17) 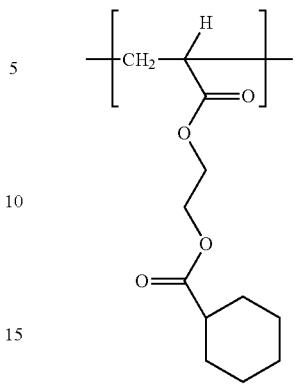
(a5-1-18) 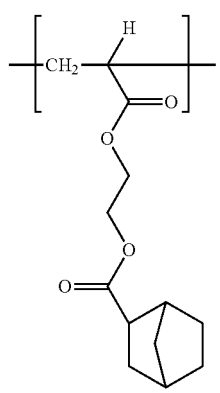
(a5-1-19) 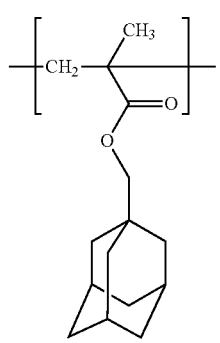
(a5-1-20) 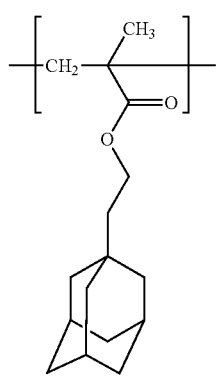

(a5-1-21)
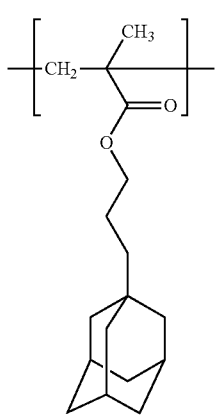

(a5-1-22)
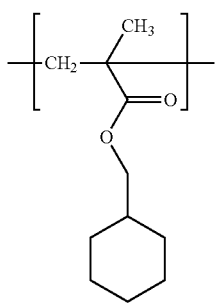

(a5-1-23)
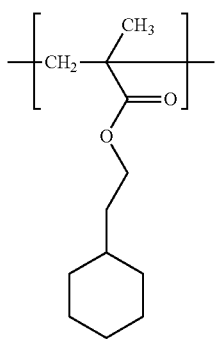

(a5-1-24)
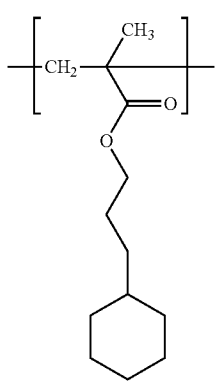

(a5-1-25)
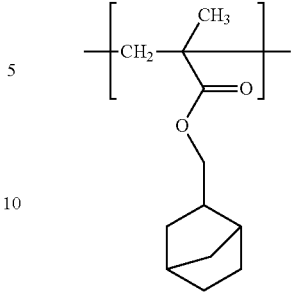

(a5-1-26)
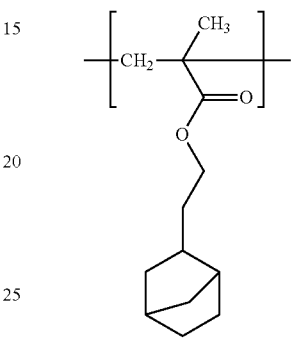

(a5-1-27)
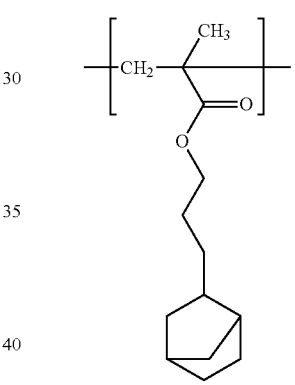

Examples of the structural units represented by formula (a5-1) include structural units represented by the formulae (a5-1-19) to (a5-1-27) in which a methyl group corresponding to $R^{51}$ has been replaced by a hydrogen atom.

When the resin (A) further has the structural unit represented by formula (a5), the content thereof is preferably 1 to 30% by mole, more preferably 2 to 20% by mole, and still more preferably 3 to 15% by mole, based on all the structural units of the resin.

Resin (A) has preferably the structural unit (a) and the structural unit having no acid-labile group.

Resin (A) has one of the structural unit (a1-1) and the structural unit (a1-2), more preferably two or more of them. The structural unit (a1-2) is preferably what comprises a cyclohexyl group or a cyclopentyl group.

The structural unit having no acid-labile group is preferably one of the structural unit (a2) and the structural unit (a3). The structural unit (a2) is preferably the structural unit (a2-1). The structural unit (a3) is preferably one of the structural unit (a3-1), the structural unit (a3-2) and the structural unit (a3-4). Resin (A) has preferably the structural unit (a1-1). The content of the structural unit (a1-1) is preferably 15% by mole or more of the total amount of the structural unit (a). The more is the structural unit having an adamantyl group, the more improved is the resistance of the photoresist film to dry etching.

Resin (A) can be produced according to known polymerization methods such as radical polymerization, using monomers corresponding to the structural units as mentioned above.

The resin has usually 2,000 or more of the weight-average molecular weight, preferably 2,500 or more of the weight-average molecular weight, more preferably 3,000 or more of the weight-average molecular weight. The resin has usually 50,000 or less of the weight-average molecular weight, preferably more 30,000 or less of the weight-average molecular weight, and preferably more 15,000 or less of the weight-average molecular weight.

The weight-average molecular weight can be measured with gel permeation chromatography.

The photoresist composition of the disclosure may further contain another resin than Resin (A).

Examples of another resin than Resin (A) include what consists of structural units having no acid-labile group, preferably what comprises, not the structural unit (a1), but the structural unit (a4). Here, another resin than Resin (A) is sometimes referred to as "Resin (X)".

Resin (X) may be one which consists of the structural unit (a4), or one which further has the structural unit (a2), the structural unit (a3) or another structural unit having no acid-labile group, known in the art.

In Resin (X), the content of the structural unit (a4) is preferably 40% by mole or more, more preferably 45% by mole or more, still more preferably 50% by mole or more, based on all the structural units of the resin.

Resin (X) usually has 6000 or more of the weight-average molecular weight, preferably 7000 or more of the weight-average molecular weight, still more preferably 8000 or more of the weight-average molecular weight.

The resin usually has 80,000 or less of the weight-average molecular weight, preferably has 60,000 or less of the weight-average molecular weight.

The weight-average molecular weight can be measured with known methods such as liquid chromatography or gas chromatography.

Resin (X) can be produced according to known polymerization methods such as radical polymerization, using monomers corresponding to the structural units as mentioned above.

When the photoresist composition contains Resin (X), the content of the resin is preferably 1 to 60 weight parts, more preferably 1 to 50 weight parts, and still more preferably 2 to 40 weight parts, and further still more preferably 2 to 30 weight parts, relative to 100 parts of Resin (A).

The total content of the resins in the photoresist composition is usually 80% by mass or more based on sum of the solid components, and usually 99% by mass or less.

In this specification, "solid component" means components other than solvent in the photoresist composition.

The photoresist composition of the disclosure may further contain a solvent.

The amount of the solvent is usually 90% by weight or more, preferably 92% by weight or more preferably 94% by weight or more based on total amount of the photoresist composition. The amount of the solvent is usually 99.9% by weight or less and preferably 99% by weight or less based on total amount of the photoresist composition. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the disclosure may further contain a quencher. The "quencher" has the property that it can trap an acid, especially an acid generated from the acid generator by applying a radiation.

Examples of the quencher include a basic nitrogen-containing organic compound and a weak acid salt.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine in which an aromatic ring has an amino group such as aniline and a heteroaromatic amine such as pyridine.

Examples of the quencher include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, 2-tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine and bipyridine.

Examples of the quaternary ammonium salts include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

The weak acid salt is usually lower in acidity than the Salt (B1) and Salt (I), examples of which include carboxylic acid salts and sulfonic acid salts.

The photoresist composition of the disclosure preferably further contains a salt which generates an acid weaker in acidity than an acid generated from the Salt (B1) and the salt (I).

The acidity in the weak acid salt is shown by the acid dissociation constant (pKa).

The acid dissociation constant of acid generated from the weak acid salt is usually $-3<pKa$.

The weak acid salt is preferably a salt of $-1<pKa<7$, and more preferably a salt of $0<pKa<5$.

Specific examples of the weak acid salt include JP2012-229206A1, JP2012-6908A1, JP2011-191745A1, JP2012-72109A1, JP2011-39502A1 and the following ones.
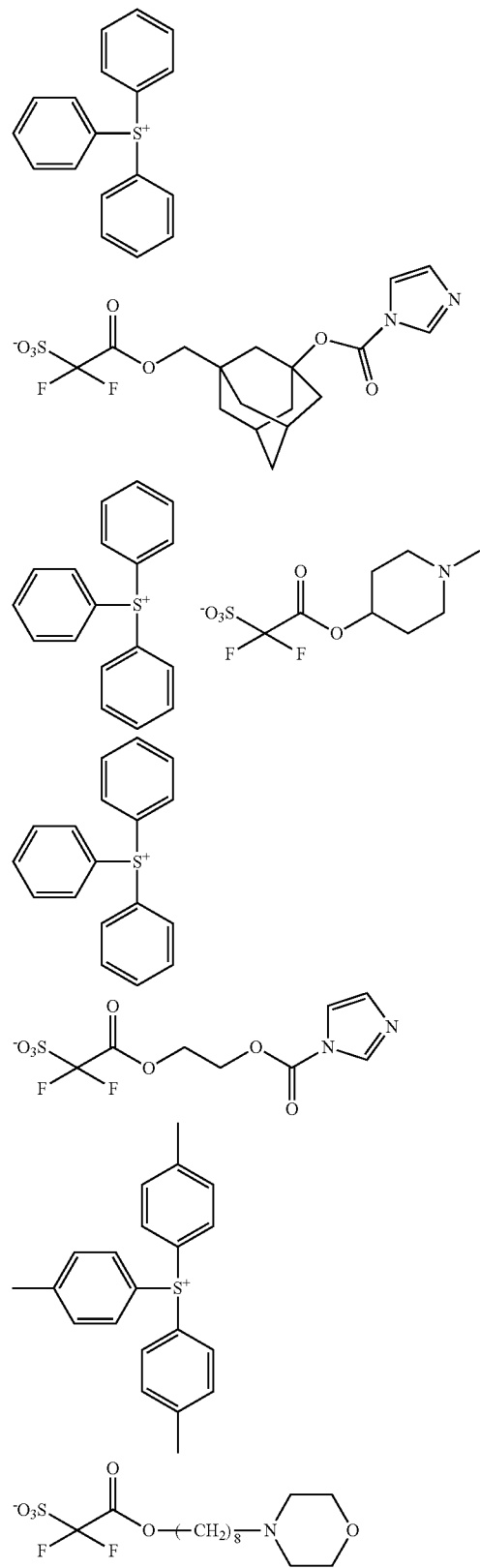
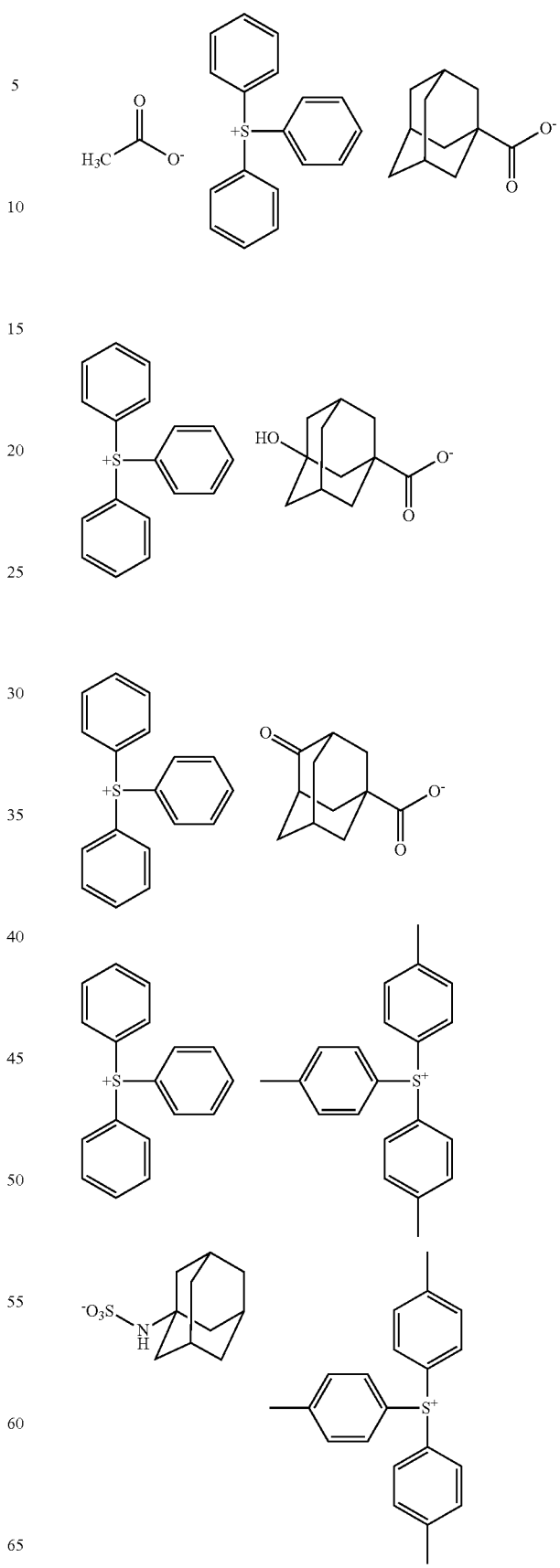

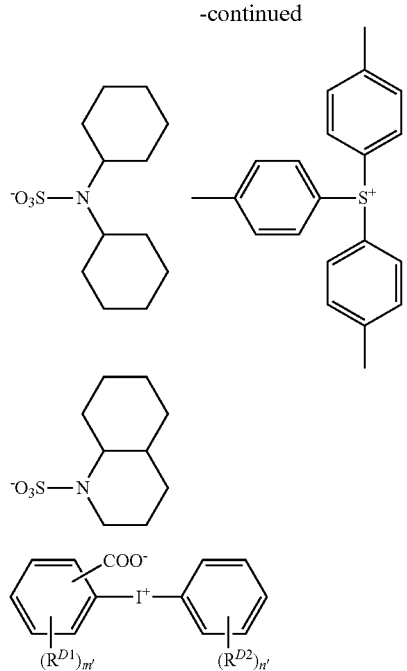

(D)

In the formula (D), $R^{D1}$ and $R^{D2}$ in each occurrence independently represent a $C_1$ to $C_{12}$ hydrocarbon group, a C1 to C6 alkoxyl group, a C2 to C7 acyl group, a C2 to C7 acyloxy group, a C2 to C7 alkoxycarbonyl group, a nitro group or a halogen atom; and m' and n' each independently represent an integer of 0 to 4.

Examples of the hydrocarbon group for $R^{D1}$ and $R^{D2}$ include any of an aliphatic hydrocarbon group, an alicyclic hydrocarbon group, an aromatic hydrocarbon group and a combination thereof.

Examples of the aliphatic hydrocarbon group include an alkyl group such as methyl, ethyl, propyl, isopropyl, butyl, isobutyl, tert-butyl, pentyl, hexyl and nonyl groups.

The alicyclic hydrocarbon group is any one of monocyclic or polycyclic hydrocarbon group, and saturated or unsaturated hydrocarbon group. Examples thereof include a cycloalkyl group such as cyclopropyl, cyclobutyl, cyclopentyl, cyclohexyl, cyclononyl and cyclododecyl groups; adamantyl and norbornyl groups.

Examples of the aromatic hydrocarbon group include an aryl group such as phenyl, 1-naphthyl, 2-naphthyl, 2-methylphenyl, 3-methylphenyl, 4-methylphenyl, 4-ethylphenyl, 4-propylphenyl, 4-isopropylphenyl, 4-butylphenyl, 4-tert-butylphenyl, 4-hexylphenyl, 4-cyclohexylphenyl, anthryl, p-adamantylphenyl, tolyl, xylyl, cumenyl, mesityl, biphenyl, phenanthryl, 2,6-diethylphenyl and 2-methyl-6-ethylphenyl groups.

Examples of the combination thereof include an alkyl-cycloalkyl, a cycloalkyl-alkyl, aralkyl (e.g., phenylmethyl, 1-phenylethyl, 2-phenylethyl, 1-phenyl-1-propyl, 1-phenyl-2-propyl, 2-phenyl-2-propyl, 3-phenyl-1-propyl, 4-phenyl-1-butyl, 5-phenyl-1-pentyl and 6-phenyl-1-hexyl groups) groups.

Examples of the alkoxyl group include methoxy and ethoxy groups.

Examples of the acyl group include acetyl, propanoyl, benzoyl and cyclohexanecarbonyl groups.

Examples of the acyloxy group include a group in which oxy group (—O—) bonds to an acyl group.

Examples of the alkoxycarbonyl group include a group in which the carbonyl group (—CO—) bonds to the alkoxy group.

Example of the halogen atom is a chlorine atom, a fluorine atom and bromine atom.

In the formula (D), $R^{D1}$ and $R^{D2}$ in each occurrence independently preferably represent a C1 to C8 alkyl group, a C3 to C10 cycloalkyl group, a C1 to C6 alkoxyl group, a C2 to C4 acyl group, a C2 to C4 acyloxy group, a C2 to C4 alkoxycarbonyl group, a nitro group or a halogen atom.

m' and n' independently preferably represent an integer of 0 to 3, more preferably an integer of 0 to 2, and more preferably 0.

Specific examples of the salt of the formula (D) include compounds below.

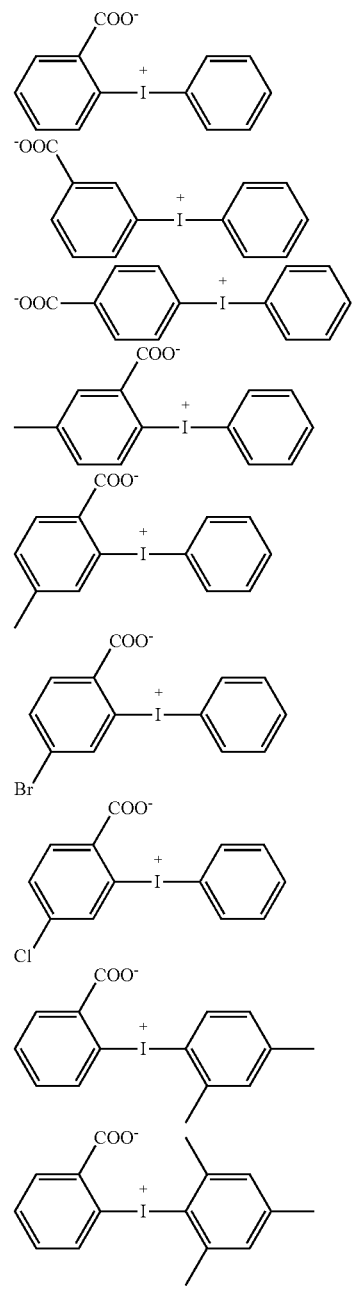

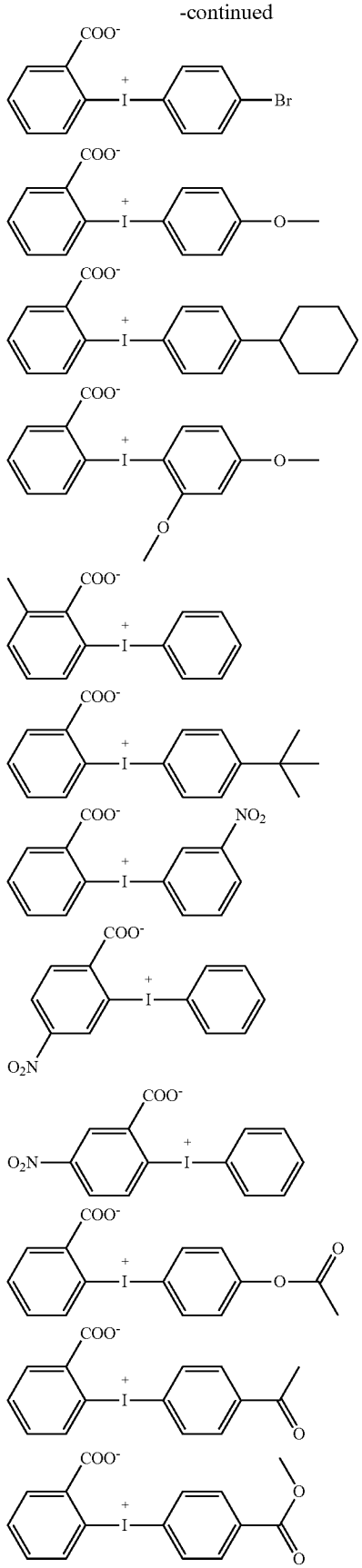

The content of quencher is preferably 0.01 to 5% by mass, more preferably 0.01 to 4% by mass, and still more preferably 0.01 to 3% by mass, based on sum of the solid components.

The photoresist composition of the disclosure may further contain, if necessary, a small amount of various additives known in the art such as a sensitizer, a dissolution inhibitor, other polymers, a surfactant, a stabilizer and a dye.

The photoresist composition of the disclosure can usually be prepared by mixing, in a solvent, Salt (I), Salt (B1) and Resin (A), and if necessary a known acid generator, a quencher, and/or additives at a suitable ratio for the composition, optionally followed by filtrating the mixture with a filter having 0.003 μm to 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the disclosure are useful for a chemically amplified photoresist composition.

Another aspect of the invention is a salt represented by the formula (Ia):

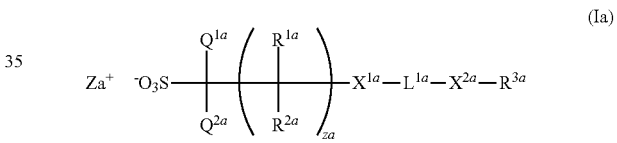

(Ia)

wherein $Q^{1a}$ and $Q^{2a}$ each independently represent a fluorine atom or a C1 to C6 perfluoroalkyl group;

$R^{1a}$ and $R^{2a}$ each independently represent a hydrogen atom, a fluorine atom or a C1 to C6 perfluoroalkyl group;

"za" represents an integer of 0 to 6;

$X^{1a}$ and $X^{2a}$ each independently represent a group having at least one of *—CO—O—, *—O—CO— and *—O— where * represents a binding site to $L^{1a}$, provided that at least one of $X^{1a}$ and $X^{2a}$ represents *—CO—O— or *—O—CO—;

$L^{1a}$ represents —$CH_2$—$(CF_2)_{na}$—$CH_2$— where "na" represents an integer of 2 to 6;

$R^{3a}$ represents a C5 to C18 alicyclic hydrocarbon group in which a hydrogen atom can be replaced by a hydroxy group and a methylene group can be replaced by an oxygen atom, a sulfonyl group or a carbonyl group, and which alicyclic hydrocarbon group may have a cyclic ketal structure optionally having a fluorine atom; and $Za^+$ represents an organic cation.

Examples of $Q^{1a}$, $Q^{2a}$, $R^{1a}$, $R^{2a}$ and $R^{3a}$ are the same as those of $Q^1$, $Q^2$, $R^1$, $R^2$ and $R^{3a}$, respectively.

Each of $Q^{1a}$ and $Q^{2a}$ is preferably a trifluoromethyl group or a fluorine atom, more preferably a fluorine atom.

Preferably, $R^{1a}$ and $R^{2a}$ are each independently a hydrogen atom or a fluorine atom.

"za" is preferably 0 or 1, more preferably 0.

The alicyclic hydrocarbon group for $R^{3a}$ is preferably an adamantyl group. Preferred examples of $R^{3a}$ include an adamantyl group, an oxoadamantyl group, a hydroxyadamantyl group and an adamantyl group having a cyclic ketal structure.

In formula (Ia), at least one of $X^{1a}$ and $X^{2a}$ represents *—CO—O— or *—O—CO—.

In formula (Ia), $X^{1a}$ represents *—CO—O—. $X^{2a}$ preferably represents *—O—CO—.

$L^{1a}$ represents —$CH_2$—$(CF_2)_{na}$—$CH_2$— where "na" represents integer of 2 to 6. "na" is preferably 2 to 4.

In formula (Ia), $Za^+$ represents an organic cation.

Examples of the organic cation represented by $Za^+$ include organic cations represented by formulae (b2-1) and (b2-2) as described above as well as the cations represented by formulae (b2-3) and (b2-4).

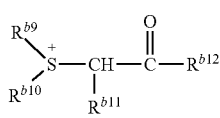

(b2-3)

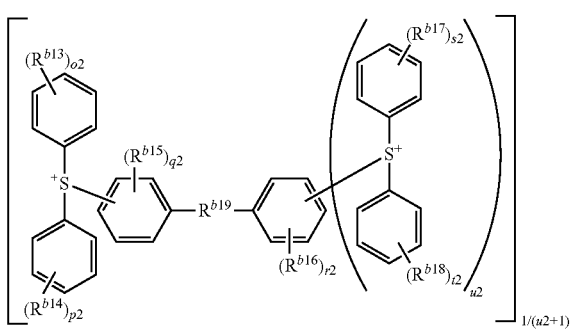

(b2-4)

In formula (b2-3), $R^{b9}$ and $R^{b10}$ each independently represent a C1 to C36 aliphatic hydrocarbon group, a C3 to C36 alicyclic hydrocarbon group, or $R^{b9}$ and $R^{b10}$ may together form a ring containing a sulfur atom to which they are attached, and the methylene groups present in the ring may be substituted with an oxygen atom, a sulfinyl group or a carbonyl group;

$R^{b11}$ represents a hydrogen atom, a C1 to C36 aliphatic hydrocarbon group, a C3 to C36 alicyclic hydrocarbon group, or a C6 to C18 aromatic hydrocarbon group;

$R^{b12}$ represents a C1 to C12 aliphatic hydrocarbon group where a hydrogen atom may be substituted with a C6 to C18 aromatic hydrocarbon group, a C3 to C18 alicyclic hydrocarbon group, or a C6 to C18 aromatic hydrocarbon group where a hydrogen atom may be substituted with a C1 to C12 alkoxy group or a C1 to C12 alkylcarbonyloxy group; or $R^{b11}$ and $R^{b12}$ may together form a ring containing —CH—CO—, and the methylene groups present in the ring may be substituted with an oxygen atom, a sulfinyl group or a carbonyl group.

In formula (b2-4), $R^{b13}$ to $R^{b18}$ each independently represent a hydroxy group, a C1 to C12 aliphatic hydrocarbon group or a C1 to C12 alkoxy group. $R^{b19}$ represents a sulfur atom or an oxygen atom.

o2, p2, s2, and t2 each independently represent an integer of 0 to 5. q2 and r2 each independently represent an integer of 0 to 4. u2 represents 0 or 1.

Examples of an aliphatic hydrocarbon group, an alicyclic hydrocarbon group and an aromatic hydrocarbon group for $R^{b9}$ to $R^{b18}$ include the same as those for $R^{b4}$ to $R^{b8}$ in formulae (b2-1) and (b2-2). When $R^{b9}$ and $R^{b10}$ together form a ring, the ring may be a monocyclic or a polycyclic, an aromatic or a non-aromatic, a saturated or an unsaturated ring. Among them, the ring is a 3-membered to 12-membered ring, preferably a 3-membered to 7-membered ring. Examples include a thiolane-1-ium ring (tetrahydrothiophenium ring), a thian-1-ium ring and a 1,4-oxathian-4-ium ring.

When $R^{b11}$ and $R^{b12}$ together form a ring, the ring may be a monocyclic or a polycyclic, an aromatic or a non-aromatic, a saturated or an unsaturated ring. Among them, the ring is a 3-membered to 12-membered ring, preferably a 3-membered to 7-membered ring. Examples include an oxocycloheptane ring, an oxocyclohexane ring, an oxonorbornane ring and an oxoadamantane ring.

Specific examples of formulae (b2-1) and (b2-2) are the same as mentioned above. Specific examples of formula (b2-3) include the following ones.

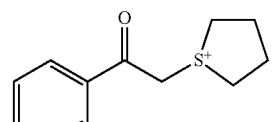

(b2-c-31)

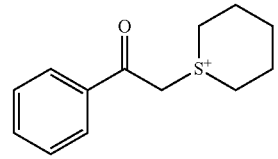

(b2-c-32)

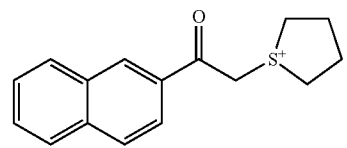

(b2-c-33)

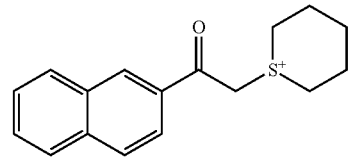

(b2-c-34)

Specific examples of formula (b2-4) include the following ones.

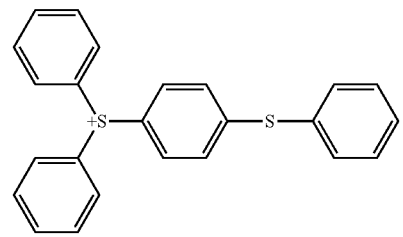

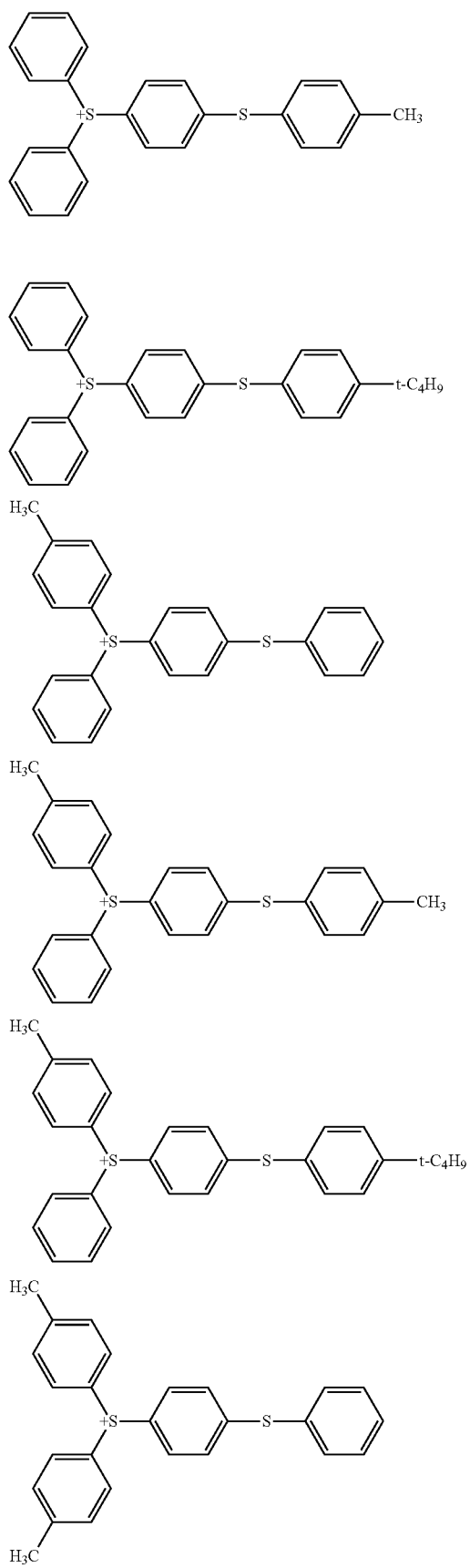

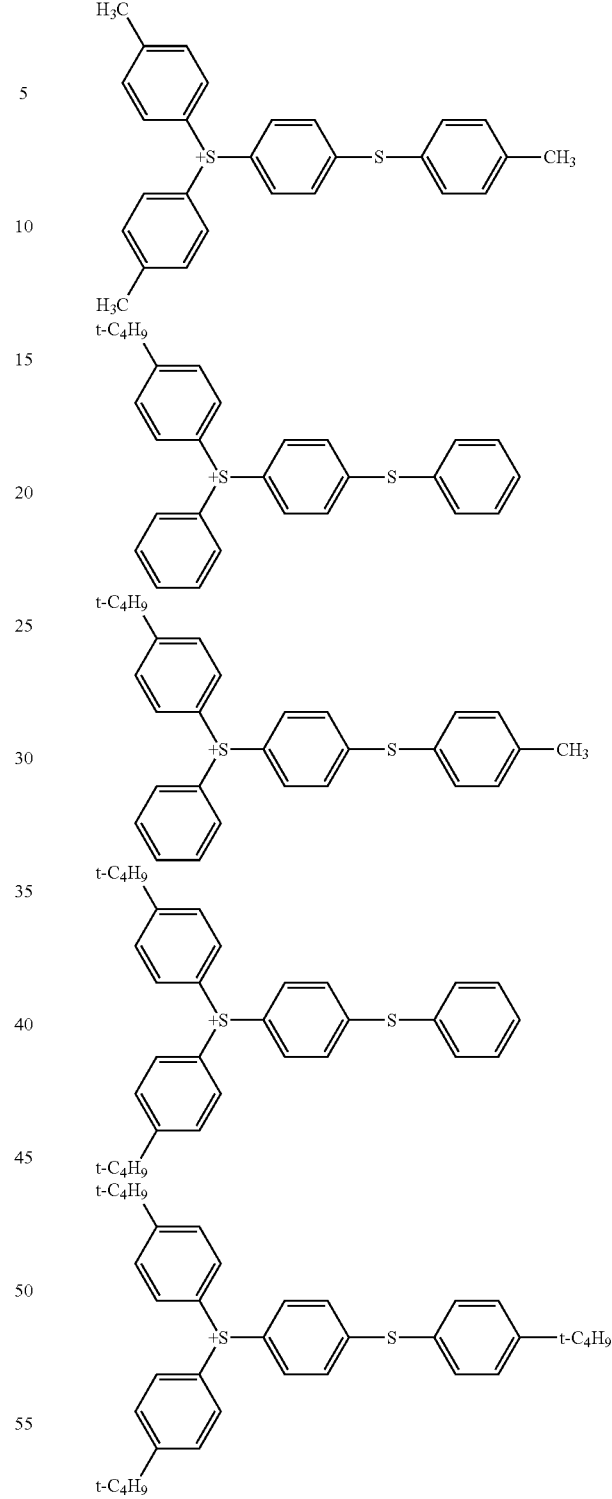

Typical examples of the salt represented by formula (Ia) include those consisting of an organic cation and an anion represented by any one of formulae (Ia-1) to (Ia-12). Among them, preferred are the salt which consists of one of the anions represented by formulae (Ia-1) to (Ia-6) and one of the cations represented by formulae (b2-1) and (b2-2), and more preferred are the salt which consists of one of the anions represented by formulae (Ia-1) to (Ia-4) and one of the cations represented by formulae (b2-c-1) and (b2-c-27).

The salt represented by formula (Ia) can be produced in the same manner as the salt (I).

The salt represented by formula (Ia) is useful for an acid generator for photoresist compositions.

An acid generator which contains a salt is one aspect of the invention. A photoresist composition which contains the salt represented by formula (Ia) and a resin having an acid-labile group, which resin is described above, is another aspect of the invention. The photoresist composition is sometimes referred to as "photoresist composition (Ia)".

The photoresist composition (Ia) may further contain another resin, a quencher, or a solvent.

The photoresist composition (Ia) preferably further contains a quencher, or a solvent, more preferably both of them.

The another resin, the quencher and the solvent for the photoresist composition (Ia) are the same as described above. The photoresist composition (Ia) may further contain, if necessary, a small amount of various additives known in the art such as a sensitizer, a dissolution inhibitor, other polymers, a surfactant, a stabilizer and a dye.

The content of each component in the photoresist composition (Ia) is the same as the photoresist composition (I).

The photoresist composition (Ia) can be produced in the same manner as the photoresist composition (I).

The photoresist compositions of the disclosure are useful for a chemically amplified photoresist composition.

A photoresist pattern can be produced by the following steps (1) to (5):

(1) a step of applying the photoresist composition of the disclosure on a substrate,
(2) a step of forming a composition film by conducting drying,
(3) a step of exposing the composition film to radiation,
(4) a step of baking the exposed composition film, and
(5) a step of developing the baked composition film with an alkaline developer.

The applying of the photoresist composition on a substrate is usually conducted using a conventional apparatus such as spin coater. The photoresist composition is preferably filtrated with filter having a pore size of 0.01 to 0.2 µm before applying. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0*10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds.

The positive and negative type photoresist patterns can be obtained by the development depending on a developer to be used therefor.

When a positive type photoresist pattern is prepared from the photoresist composition of the disclosure, the development can be conducted with an alkaline developer. The alkaline developer to be used may be any one of various aqueous alkaline solution used in the art. Generally, an aqueous solution of tetramethylammonium hydroxide or (2-hydroxyethyl)trimethylammonium hydroxide (commonly known as "choline") is often used. The alkaline developer may contain a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the disclosure, the development can be conducted with a developer containing an organic solvent, such developer is sometimes referred to as "organic developer". Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 50% to 100% by weight, more preferably from 90% to 100% by weight. Preferred is that the organic developer essentially consists of butyl acetate and/or 2-heptanone.

The organic developer may comprise a surfactant or a very small amount of water.

Development with an organic developer can be stopped by replacing the developer by other solvent than it such as alcohol.

The photoresist composition of the disclosure is suitable for KrF excimer laser lithography, ArF excimer laser lithography, EUV (extreme ultraviolet) lithography and EB (electron beam) lithography, particularly for ArF excimer laser lithography.

EXAMPLES

The invention as mentioned above will be described more specifically by Examples, which are not construed to limit the scope of the disclosure.

The "%" and "part(s)" used to represent the content of any component and the amount of any material used in the following examples and comparative examples are on a mass basis unless otherwise specifically noted.

The weight-average molecular weight of any material used in the following examples was determined with gel permeation chromatography under the following condition.

Equipment: HLC-8120 GCP type, manufactured by TOSOH CORPORATION
Column: Three of TSKgel Multipore $H_{XL}$-M with guard column, manufactured by TOSOH CORPORATION
Solvent: tetrahydrofuran
Flow rate: 1.0 mL/min.
Detector: RI Detector
Column temperature: 40° C.
Injection volume: 100 µL
Standard reference material: Standard polystyrene (manufactured by TOSOH CORPORATION)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Here, the values at the peaks of spectrum are referred to as "MASS."

Example 1

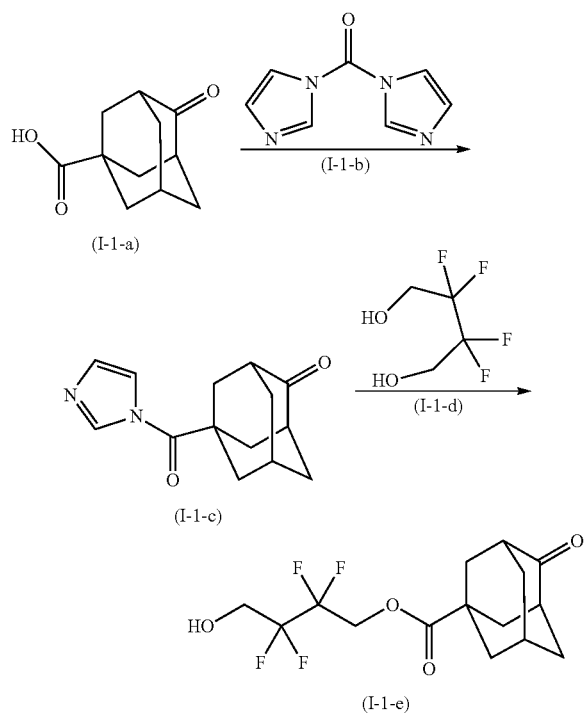

To a reactor, 15 parts of compound represented by the formula (I-1-a) and 75 parts of acetonitrile were added, and the mixture was stirred at 23° C. for 30 minutes. To the resultant mixture, 13.77 parts of the compound represented by the formula (I-1-b) was added and then stirred at 70° C. for 2 hours to thereby obtain a solution containing a compound of the formula (I-1-c). To the obtained solution, 25.03 parts of the compound represented by the formula (I-1-d) was added, and further stirred at 23° C. for 48 hours, followed by being concentrated. To the resultant concentrate, 170 parts of chloroform and 170 parts of 10% aqueous oxalic acid solution were added and stirred at 23° C. for 30 minutes, followed by being filtrated. Then the filtrated solution was separated to thereby collect an organic layer therefrom.

To the obtained organic layer, 170 parts of ion-exchanged water was added and stirred at 23° C. for 30 minutes, followed by separating an organic layer therefrom. This operation was conducted 5 times. The resultant organic layer was concentrated to thereby obtain 24.74 parts of a compound represented by formula (I-1-e).

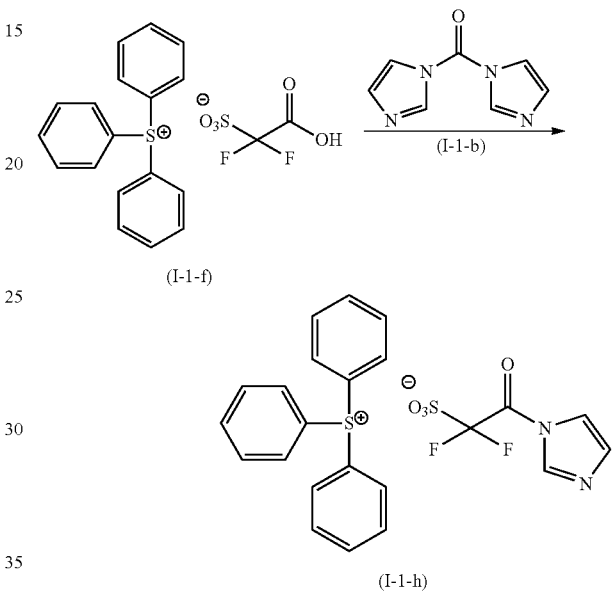

To a reactor, 9.98 parts of the salt represented by formula (I-1-f) and 50 parts of acetonitrile were added, and stirred at 23° C. for 30 minutes. To the resultant mixture, 4.04 parts of the compound represented by formula (I-1-b) was added and then stirred at 70° C. for 2 hours to obtain a solution containing a salt represented by the formula (I-1-h).

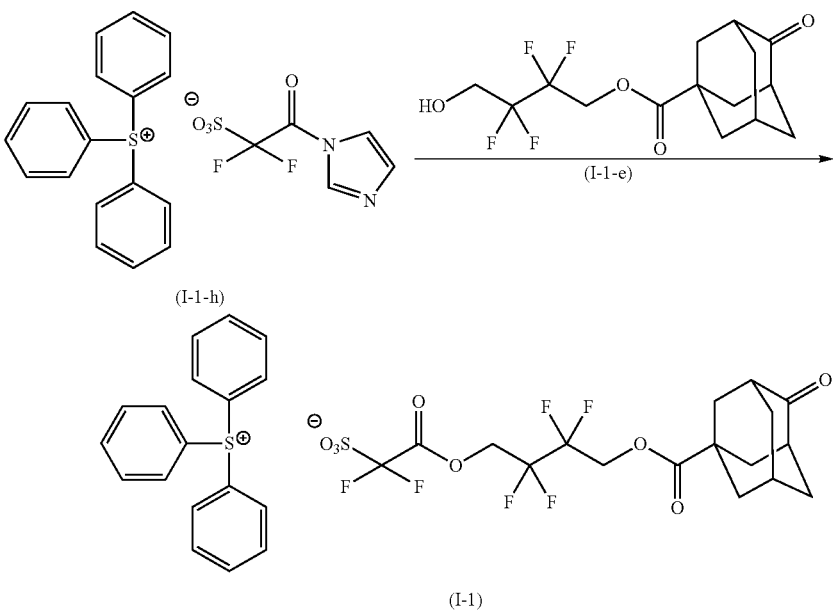

To the resultant solution, 6.93 parts of the compound represented by the formula (I-1-e) was added and then stirred at 23° C. for 18 hours, followed by being concentrated. To the resultant concentrate, 80 parts of chloroform and 80 parts of 10% aqueous oxalic acid solution were added and stirred at 23° C. for 30 minutes, followed by being filtrated. Then the filtrated solution was separated to thereby collect an organic layer therefrom. To the resultant organic layer, 40 parts of ion-exchanged water was added and stirred at 23° C. for 30 minutes, followed by separating the organic layer therefrom. This operation was conducted 5 times. The obtained organic layer was concentrated and the resultant residue was stirred and 70 parts of tert-butylmethylether was added thereto and stirred, followed by removing the supernatant therefrom. The resultant residue was concentrated to thereby obtain 13.96 parts of the salt represented by the formula (I-1).

MASS (ESI(+) Spectrum): M⁺ 263.1
MASS (ESI(−) Spectrum): M⁻ 495.1

Example 2

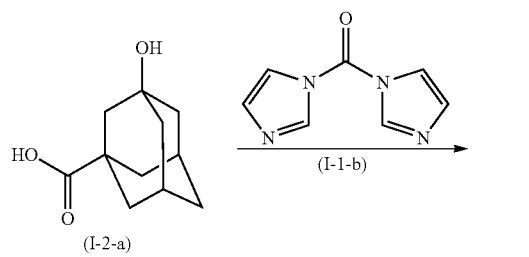

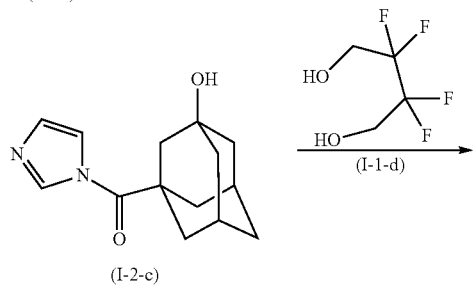

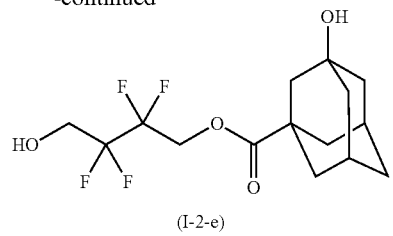

To a reactor, 20 parts of the compound represented by formula (I-2-a) and 100 parts of acetonitrile were added, and the mixture was stirred at 23° C. for 30 minutes. To the resultant mixture, 18.18 parts of the compound represented by formula (I-1-b) was added and further stirred at 70° C. for 2 hours to thereby obtain a solution containing a compound represented by formula (I-2-c). To the resultant solution, 33.04 parts of the compound represented by formula (I-1-d) was added and further stirred at 23° C. for 48 hours, and concentrated.

To the resultant concentrate, 240 parts of chloroform and 240 parts of 10% aqueous oxalic acid solution were added and stirred at 23° C. for 30 minutes, followed by being filtrated. Then the filtrated solution was separated to thereby collect an organic layer. To the resultant organic layer, 120 parts of ion-exchanged water was added and stirred at 23° C. for 30 minutes, followed by separating the organic layer therefrom. This operation was conducted 3 times. The obtained organic layer was concentrated to thereby obtain 30.77 parts of the compound represented by formula (I-2-e).

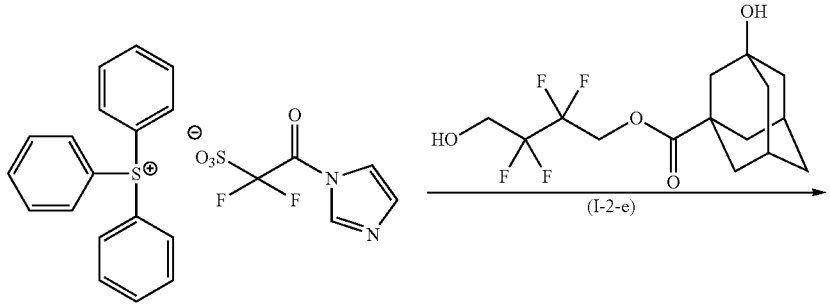

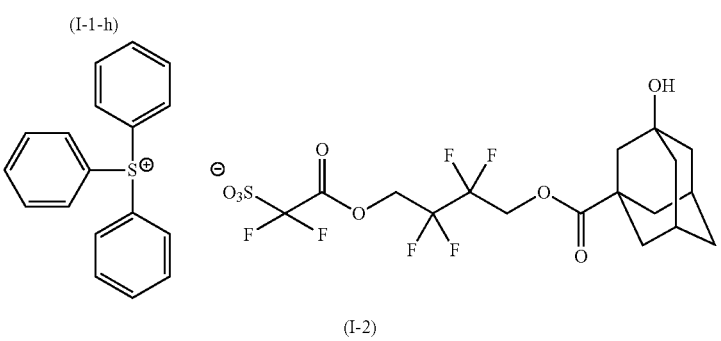

To the resultant solution containing the salt represented by formula (I-1-h), which solution was prepared in the same manner as described in Example 1, 6.97 parts of the compound represented by formula (I-2-e) was added and further stirred at 23° C. for 18 hours, followed by being concentrated. To the resultant concentrate, 70 parts of chloroform and 70 parts of 10% aqueous oxalic acid solution were added and stirred at 23° C. for 30 minutes, followed by being filtrated. Then the filtrated solution was separated to thereby collect an organic layer therefrom. To the resultant organic layer, 40 parts of ion-exchanged water was added and stirred at 23° C. for 30 minutes, followed by separating an organic layer therefrom. This operation was conducted 5 times. The obtained organic layer was concentrated and the resultant residue was stirred and then 70 parts of tert-butylmethylether was added thereto, followed by removing the supernatant therefrom. The resultant residue was concentrated to thereby obtain 12.23 parts of the salt represented by the formula (I-2).

MASS (ESI(+) Spectrum): $M^+$ 263.1
MASS (ESI(−) Spectrum): $M^-$ 497.1

Example 3

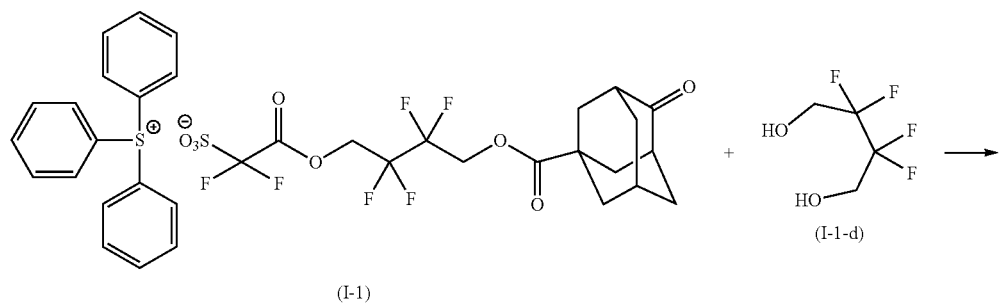

(I-1)

(I-1-d)

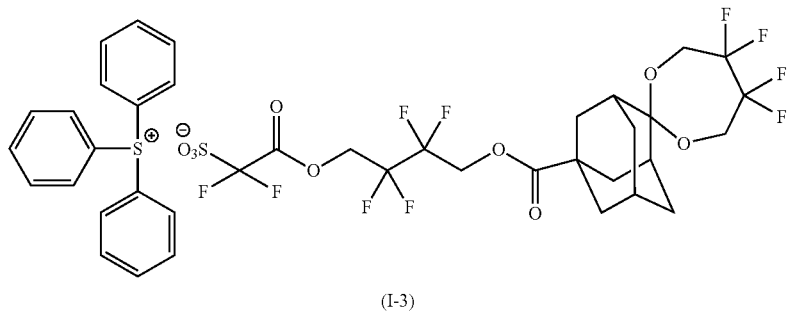

(I-3)

Into a reactor, 2.28 parts of the salt represented by formula (I-1), 0.73 parts of the compound represented by the formula (I-1-d) and 10 parts of 1,2-dichloroethane were added and stirred at 23° C. for 30 minutes.

To the obtained mixture, 0.01 parts of p-toluenesulfonic acid was added, and refluxed and stirred at 60° C. for 3 hours, followed by being cooled to 23° C. Then 30 parts of chloroform and 10 parts of 5% aqueous sodium hydrogen carbonate solution was added thereto, stirred at 23° C. for 30 minutes, followed by setting still and collecting an organic layer therefrom.

To the obtained organic layer, 10 parts of ion-exchanged water was added, and stirred at 23° C. for 30 minutes, followed by separating an organic layer. The washing step with water was conducted seven times.

Then 1 part of active carbon was added to the obtained organic layer and stirred at 23° C. for 30 minutes, followed by being filtrated. The obtained filtrates were concentrated. To the obtained residue, 30 parts of tert-butylmethylether was added and stirred at 23° C. for 30 minutes, and then its supernatant was removed therefrom. The obtained residue was concentrated to obtain 0.78 parts of the salt represented by formula (I-3).

MASS (ESI(+) Spectrum): $M^+$ 263.1
MASS (ESI(−) Spectrum): $M^-$ 639.1

Example 4

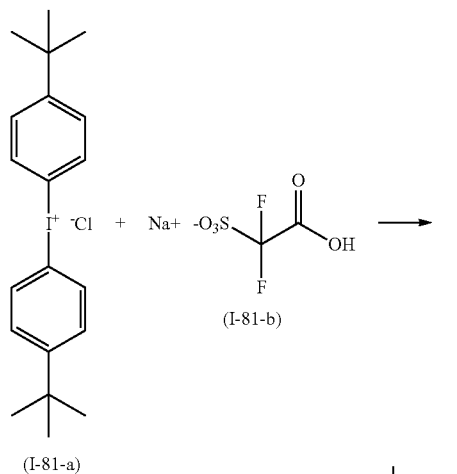

(I-81-a)  +  (I-81-b)  →

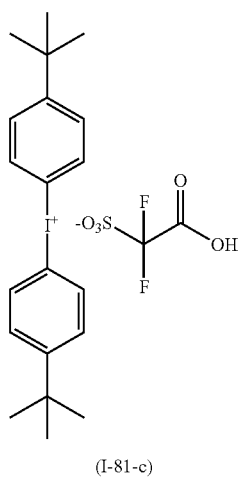

(I-81-c)

Into a reactor, 19.34 parts of the salt represented by formula (I-81-a), 8.96 parts of the salt represented by formula (I-81-b), 100 parts of acetonitrile and 50 parts of ion-exchanged water were charged, and stirred at 23° C. for 15 hours. The obtained reaction mixture was concentrated, followed by extracting an organic layer with 100 parts of chloroform. The obtained organic layer was concentrated to thereby obtain 21.78 parts of the salt represented by formula (I-81-c).

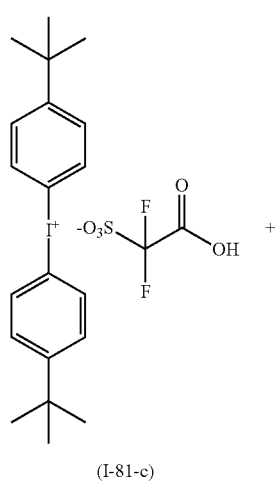

(I-81-c)

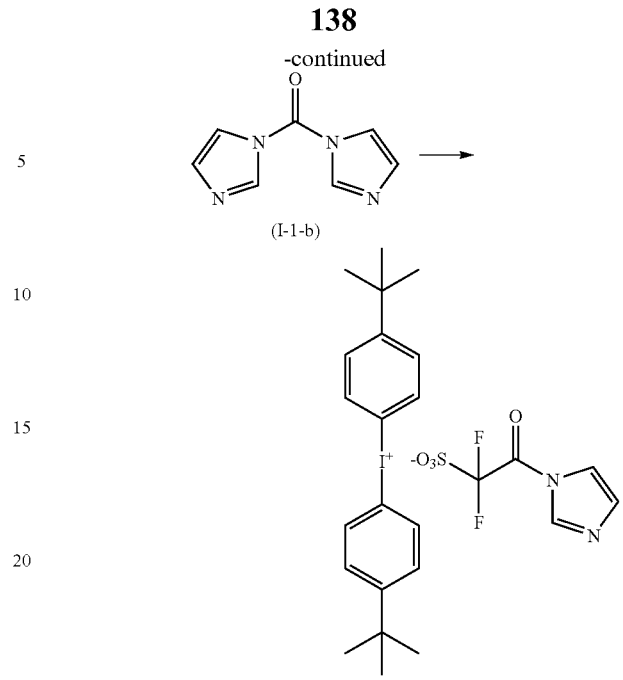

Into a reactor, 19.37 parts of the salt represented by formula (I-81-c), 11.05 parts of the compound represented by formula (I-1-b) and 100 parts of acetonitrile were charged, and stirred at 23° C. for 30 minutes, and then increased the temperature of the mixture to 50° C., followed by being stirred for 2 hours. The obtained reaction mixture was cooled to 23° C., followed by being filtrated to thereby obtain a solution containing 21.08 parts of the salt represented by formula (I-81-e).

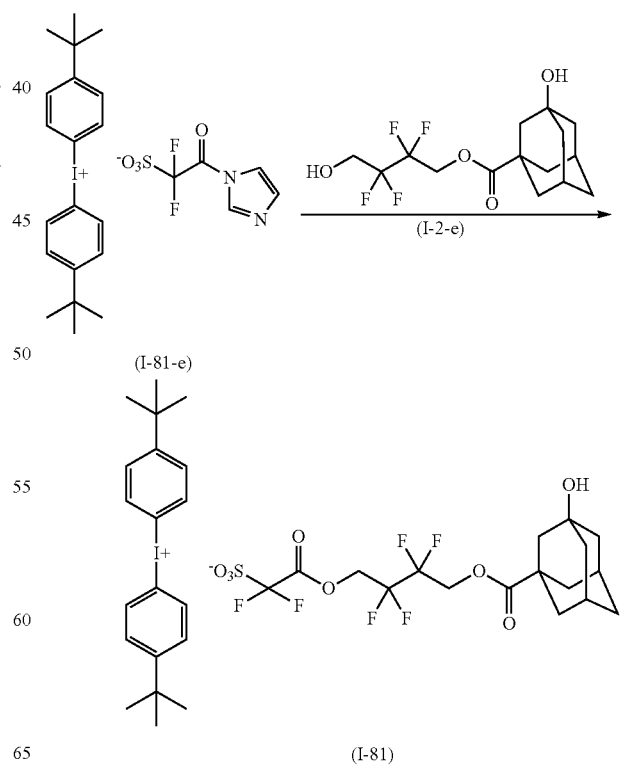

(I-81)

To a solution containing 14.08 parts of the salt represented by formula (I-81-e), 6.97 parts of the compound represented by formula (I-2-e) was added, and stirred at 23° C. for 18 hours. The obtained reaction mixture was concentrated, and then 70 parts of chloroform and 70 parts of 10% aqueous oxalic acid solution were added and then stirred at 23° C. for 30 minutes, followed by being filtrated. Then the filtrated solution was separated to thereby collect an organic layer therefrom.

To the obtained organic layer, 40 parts of ion-exchanged water were added, and stirred at 23° C. for 30 minutes, followed by separating an organic layer therefrom. The washing step was conducted five times. To the obtained organic layer, 70 parts of tert-butylmethylether was added and then stirred, followed by removing the supernatant therefrom. The resultant residue was concentrated to thereby obtain 15.48 parts of the salt represented by the formula (I-81).

MASS (ESI(+) Spectrum): M⁺ 393.1
MASS (ESI(−) Spectrum): M⁻ 497.1

Example 5

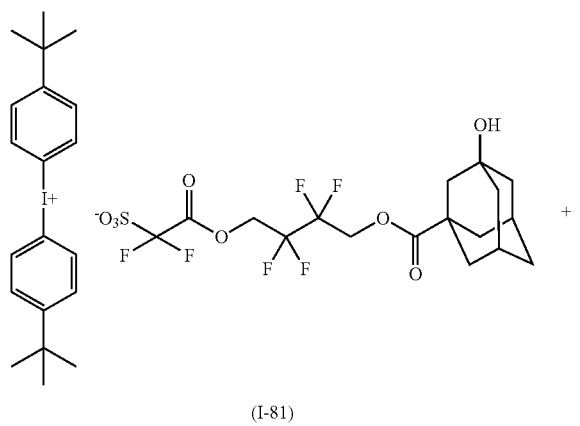

(I-81)

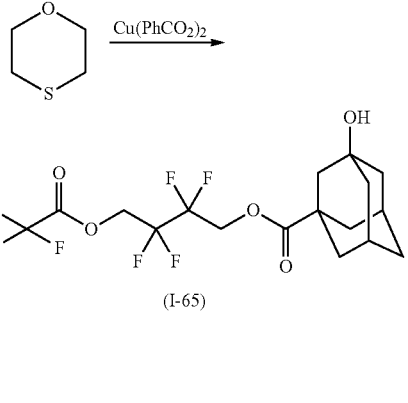

Into a reactor, 2.43 parts of the salt represented by formula (I-81), 0.28 parts of the compound represented by formula (I-65-a) and 30 parts of monochlorobenzene were added and stirred at 23° C. for 30 minutes.

To the obtained mixture, 0.02 parts of copper (II) dibenzoate was added, and stirred at 100° C. for an hour.

The obtained reaction mixture was concentrated, and then 20 parts of chloroform and 10 parts of ion-exchanged water were added thereto and stirred at 23° C. for 30 minutes, followed by separating an organic layer therefrom.

To the obtained organic layer, 10 parts of ion-exchanged water was added, and stirred at 23° C. for 30 minutes, followed by separating an organic layer. The washing step with water was conducted five times.

The resultant organic layer was concentrated, and then 70 parts of tert-butylmethylether was added thereto and then stirred, followed by removing a supernatant therefrom.

The resultant residue was concentrated to thereby obtain 1.24 parts of the salt represented by formula (I-65).

MASS (ESI(+) Spectrum): M⁺ 237.1
MASS (ESI(−) Spectrum): M⁻ 497.1

Synthesis Example 1

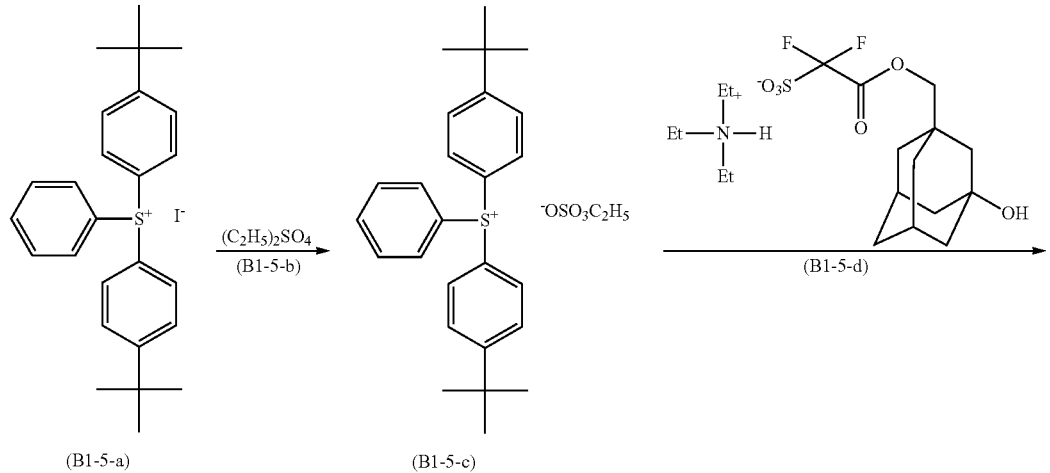

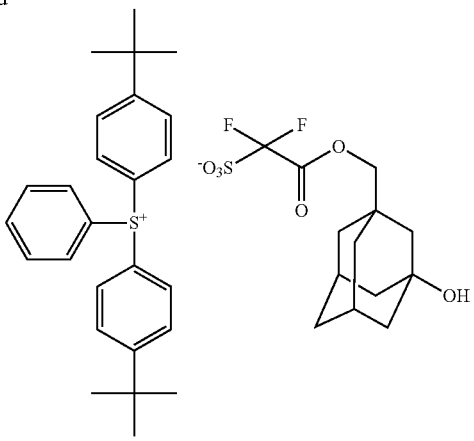

(B1-5)

Into a reactor, 50.49 parts of a salt represented by the formula (B1-5-a) and 252.44 parts of chloroform were charged and stirred at 23° C. for 30 minutes. Then 16.27 parts of a compound represented by the formula (B1-5-b) were dropped thereinto and the obtained mixture was stirred at 23° C. for one hour to obtain a solution containing a salt represented by the formula (B1-5-c). To the obtained solution, 48.80 parts of a salt represented by the formula (B1-5-d) and 84.15 parts of ion-exchanged water were added and the obtained mixture was stirred at 23° C. for 12 hours. From the obtained solution which had two layers, a chloroform layer was collected and then 84.15 parts of ion-exchanged water were added thereto for washing. These step were conducted five times. To the washed chloroform layer, 3.88 parts of active carbon was added and the obtained mixture was stirred, followed by filtrating. The collected filtrate was concentrated and then 125.87 parts of acetonitrile were added thereto and the obtained mixture was stirred, followed by being concentrated.

20.62 parts of acetonitrile and 309.30 parts of tert-butylmethylether were added to the obtained residues, followed by being stirred at 23° C. for about 30 minutes. Then a supernatant was removed therefrom, and the residues were concentrated. To the concentrated residues, 200 parts of n-heptane were added and the obtained mixture was stirred at 23° C. for about 30 minutes, followed by being filtrated to obtain 61.54 parts of the salt represented by the formula (B1-5).

MASS (ESI(+) Spectrum):M+ 375.2
MASS (ESI(−) Spectrum):M− 339.1

Synthesis Example 2

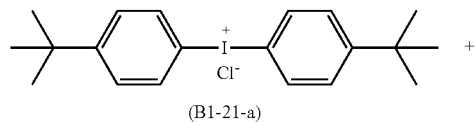

(B1-21-a)

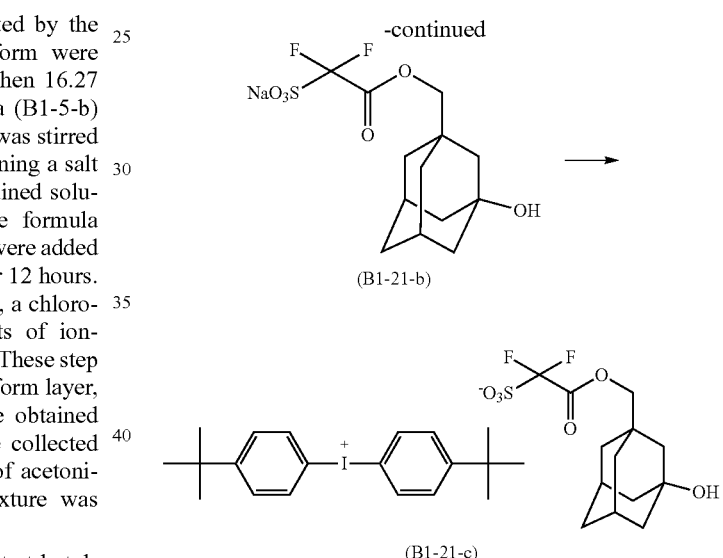

(B1-21-b)

(B1-21-c)

The compound represented by the formula (B1-21-b) was produced according to a method recited in JP2008-209917A1.

Into a reactor, 30.00 parts of the compound represented by the formula (B1-21-b) and 35.50 parts of a salt represented by the formula (B1-21-a), 100 parts of chloroform and 50 parts of ion-exchanged water were charged and stirred at 23° C. for about 15 hours. From the obtained solution which had two layers, a chloroform layer was collected and then 30 parts of ion-exchanged water was added thereto for washing. These steps were conducted five times. Then the washed layer was concentrated, and then, 100 parts of tert-butylmethylether was added to the obtained residues and the obtained mixture was stirred at 23° C. for about 30 minutes. The resulting mixture was filtrated to obtain 48.57 parts of the salt represented by the formula (B1-21-c).

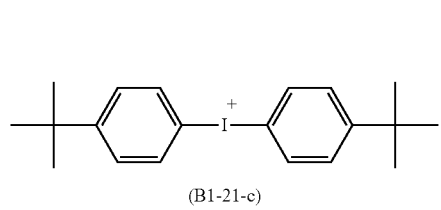

(B1-21-c)

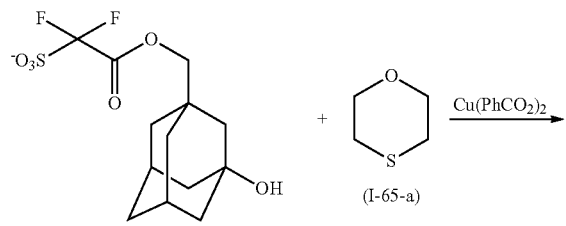

(I-65-a)

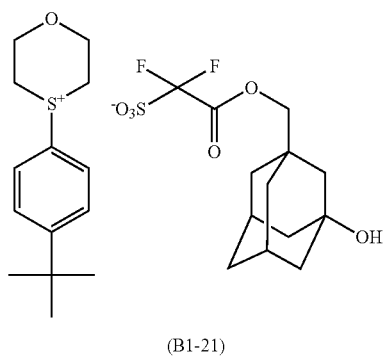

(B1-21)

Into a reactor, 20.00 parts of salt represented by the formula (B1-21-c), 2.84 parts of compound represented by the formula (I-65-a) and 250 parts of monochlorobenzene were charged and stirred at 23° C. for 30 minutes. To the resulting mixture, 0.21 parts of copper (II) dibenzoate was added and the obtained mixture was stirred at 100° C. for 1 hour. The reaction mixture was concentrated, and then, 200 parts of chloroform and 50 parts of ion-exchanged water were added to the obtained residues and the obtained mixture was stirred at 23° C. for 30 minutes, followed by separating an organic layer. 50 parts of ion-exchanged water was added to the obtained organic layer, and the obtained mixture was stirred at 23° C. for 30 minutes, followed by separating an organic layer. The washing step with water was conducted five times. The obtained organic layer was concentrated, and then the obtained residues were dissolved in 53.51 parts of acetonitrile. Then the mixture was concentrated, and 113.05 parts of tert-butylmethylether was added thereto and the obtained mixture was stirred, followed by filtrating it to obtain 10.47 parts of the salt represented by the formula (B1-21).

MASS(ESI(+)Spectrum):M+ 237.1

MASS(ESI(−)Spectrum):M− 339.1

Synthesis Example 3

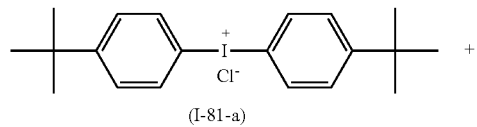

(I-81-a)

-continued

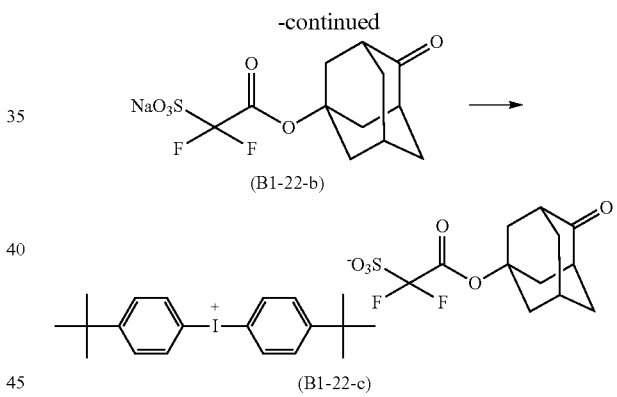

Into a reactor, 11.26 parts of the salt represented by the formula (I-81-a), 10.00 parts of the compound represented by the formula (B1-22-b), 50 parts of chloroform and 25 parts of ion-exchanged water was fed and then they were stirred at 23° C. for 15 hours. From the obtained reaction mixture which had two phases, a chloroform phase was collected with separation.

The chloroform phase was washed with 15 parts of ion-exchanged water for washing: This washing was conducted five times. The washed chloroform phase was concentrated. To the obtained residue, 50 parts of tert-butylmethylether was added and then stirred at 23° C. for 30 minutes, followed by being filtrated to obtain 11.75 parts of the salt represented by the formula (B1-22-c).

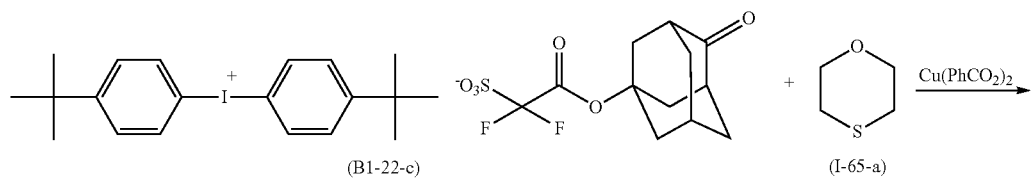

(B1-22-c)         (I-65-a)

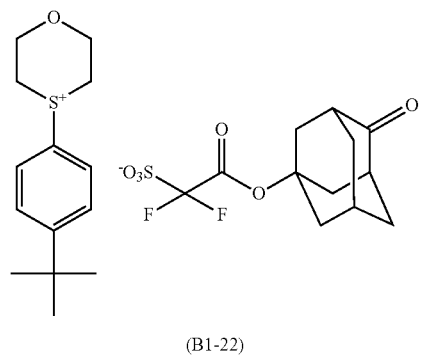

(B1-22)

Into a reactor, 11.71 parts of the salt represented by the formula (B1-22-c), 1.70 parts of the compound represented by the formula (I-65-a) and 46.84 parts of monochlorobenzene were fed and then they were stirred at 23° C. for 30 minutes.

To the resultant mixture, 0.12 part of copper (II) dibenzoate was added. The resultant mixture was stirred at 100° C. for 30 minutes. The mixture was concentrated, and then 50 parts of chloroform and 12.50 parts of ion-exchanged water were added to the obtained residue, followed by being stirred at 23° C. for 30 minutes. Then the organic phase was collected by separation. Then 12.50 parts of ion-exchanged water was added to the organic layer and they were stirred at 23° C. for 30 minutes, followed by collecting an organic phase by separation: This washing was conducted eight times. The washed organic layer was concentrated. To the residue, 50 parts of tert-butylmethylether was added, followed by being filtrated to obtain 6.84 parts of the salt represented by the formula (B1-22).

MASS (ESI(+) Spectrum): M⁺ 237.1

MASS (ESI(−) Spectrum): M⁻ 323.0

Compounds used as monomers in the following Synthesis Examples are shown as follow.

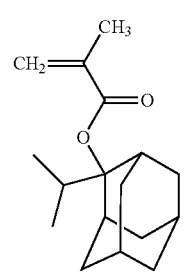

(a1-1-3)

-continued

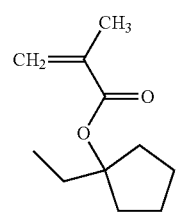

(a1-2-9)

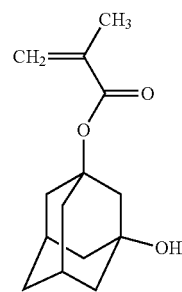

(a2-1-1)

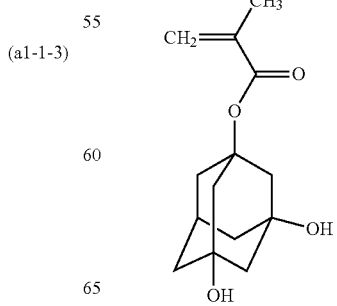

(a2-1-3)

(a3-4-2)

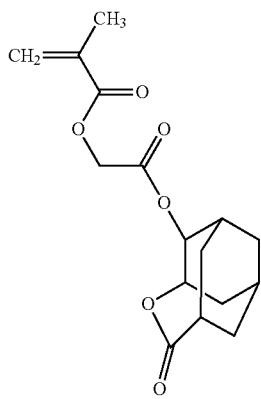

(a4-0-1)

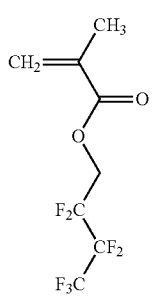

(a4-0-12)

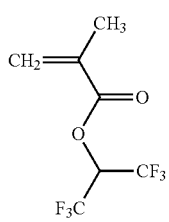

(a4-1-7)

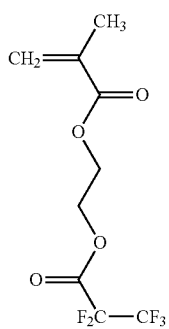

(a5-1-1)

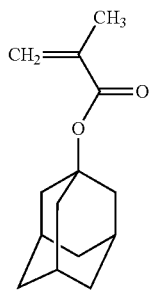

Here, each of the compounds is referred as to "monomer (X)" where "X" is the symbol of the formula representing the monomer.

Synthesis Example 4

Monomers (a1-1-3), (a1-2-9), (a2-1-3) and (a3-4-2) were mixed in a molar ratio of 45/14/2.5/38.5 (monomer (a1-1-3)/monomer (a1-2-9)/monomer (a2-1-3)/monomer (a3-4-2)), and propyleneglycolmonomethylether acetate was added thereto in the amount of 1.5 times on weight basis relative to all monomers to prepare a mixture. To the mixture, azobisisobutyronitrile and azobis(2,4-dimethylvaleronitrile) were added as initiators in the ratio of 1% by mole and 3% by mole with respect to molar amounts of all the monomers, and the obtained mixture was heated at 73° C. for about 5 hours. The reaction mixture was poured into a large amount of a mixture of methanol and water to cause precipitation. The precipitate was collected by filtration.

Then the filtrates were dissolved in propyleneglycolmonomethylether acetate and poured the resultant solution into a large amount of a mixture of methanol and water to cause precipitation, followed by being filtrated: This operation was conducted twice for purification.

As a result, a resin having a weight-average molecular weight of about $7.6 \times 10^3$ was obtained in yield of 68%. This resin is referred to as Resin A1. Resin A1 had the following structural units.

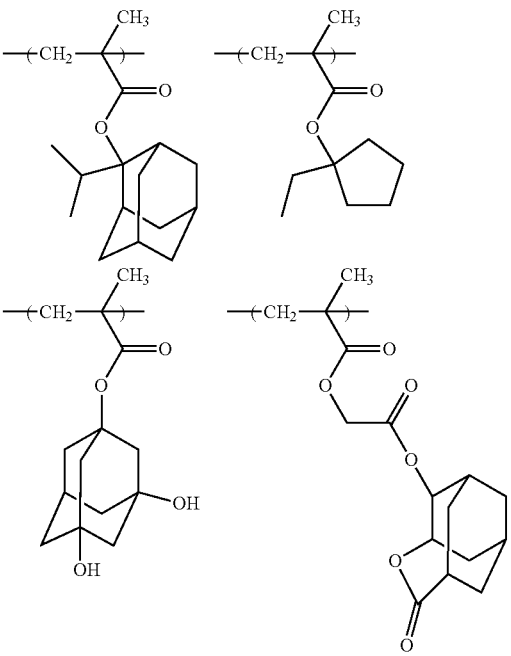

Synthesis Example 5

Monomers (a1-1-3), (a1-2-9), (a2-1-1) and (a3-4-2) were mixed in a molar ratio of 45/14/2.5/38.5 (monomer (a1-1-3)/monomer (a1-2-9)/monomer (a2-1-1)/monomer (a3-4-2)), and propyleneglycolmonomethylether acetate was added thereto in the amount of 1.5 times on weight basis relative to all monomers to prepare a mixture. To the mixture, azobisisobutyronitrile and azobis(2,4-dimethylvaleronitrile) were added as initiators in the ratio of 1% by mole and 3% by mole with respect to molar amounts of all the monomers, and the obtained mixture was heated at 73°

C. for about 5 hours. The reaction mixture was poured into a large amount of a mixture of methanol and water to cause precipitation.

The precipitate was collected by filtration.

Then the filtrates were dissolved in propyleneglycolmonomethylether acetate and poured the resultant solution into a large amount of a mixture of methanol and water to cause precipitation, followed by being filtrated: This operation was conducted twice for purification.

As a result, a resin having a weight-average molecular weight of about $7.9 \times 10^3$ was obtained in yield of 70%. This resin is referred to as Resin A1-2. Resin A1-2 had the following structural units.

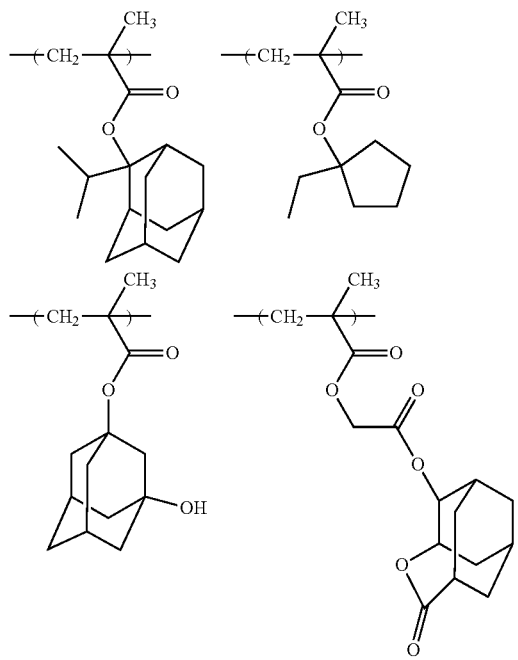

Synthesis Example 6

To monomer (a4-1-7), dioxane was added in the amount of 1.5 times on weight basis relative to all monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. The filtrates were dissolved in dioxane, and the resultant solution was poured into a large amount of a mixture of methanol and water to precipitate the resin, followed by being filtrated: This operation was conducted twice for purification.

The obtained resin had a weight average molecular weight of about 18000 in yield 77%. This resin, which had the structural unit of the following formula, is referred to as Resin X1.

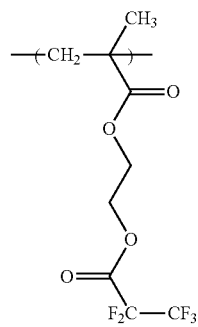

Synthesis Example 7

Monomer (a5-1-1) and monomer (a4-0-1) were mixed together with the mole ratio of monomer (a5-1-1) and monomer (a4-0-1)=50:50, and methylisobutylketone was added thereto in the amount of 1.2 times on weight basis relative to all monomers to obtain a solution. Azobis(2,4-dimethylvaleronitrile) was added as an initiator to the solution in the amounts of 4% by mole with respect to the total amount of monomers, and the resultant mixture was heated for about 5 hours at 70° C. Then, the obtained reaction mixture was poured into a large amount of a mixture of methanol and water to precipitate a resin. The obtained resin had a weight average molecular weight of about 18000 in 85% yield. This resin, which had the structural units of the following formulae, was referred to as Resin X2.

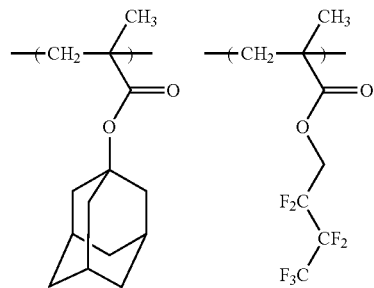

Synthesis Example 8

Monomer (a5-1-1) and monomer (a4-0-12) were mixed together with the mole ratio of monomer (a5-1-1) and monomer (a4-0-12)=50:50, and methylisobutylketone was added thereto in the amount of 1.2 times on weight basis relative to all monomers to obtain a solution.

Azobis(2,4-dimethylvaleronitrile) was added as an initiator to the solution in the amounts of 3% by mole with respect to the total amount of monomers, and the resultant mixture was heated for about 5 hours at 70° C. Then, the obtained reaction mixture was poured into a large amount of a mixture of methanol and water to precipitate a resin. The obtained resin had a weight average molecular weight of about 10000 in 91% yield. This resin, which had the structural units of the following formulae, was referred to as Resin X3.

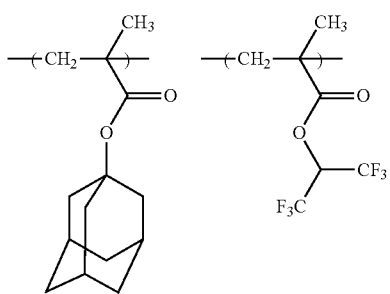

Examples 6 to 16, Test Examples 1 to 2 and Comparative Example 1

Production of Photoresist Compositions

The following components as listed in Table 4 were mixed and dissolved in the solvent as mentioned below, and then filtrated through a fluorine resin filter having pore diameter of 0.2 μm, to prepare photoresist compositions.

TABLE 4

| Comp. No. | Resin (kind/ amount (part)) | Salt (B1) (kind/ amount (part)) | Salt (I) (kind/ amount (part)) | Quencher (kind/ amount (part)) | PB(° C.)/ PEB (° C.) |
|---|---|---|---|---|---|
| Comp. 1 | X1/0.2 A1/10 | B1-21/0.9 | I-1/0.2 | D1/0.28 | 90/85 |
| Comp. 2 | X1/0.2 A1/10 | B1-5/0.2 | I-1/0.4 | D1/0.28 | 90/85 |
| Comp. 3 | X1/0.2 A1/10 | None | I-1/0.6 | D1/0.28 | 90/85 |
| Comp. 4 | X1/0.2 A1/10 | B1-21/0.9 | I-2/0.3 | D1/0.28 | 90/85 |
| Comp. 5 | X1/0.2 A1/10 | B1-5/0.2 | I-2/0.4 | D1/0.28 | 90/85 |
| Comp. 6 | X1/0.2 A1/10 | None | I-2/0.6 | D1/0.28 | 90/85 |
| Comp. 7 | X2/0.2 A1/10 | B1-21/0.9 | I-1/0.2 | D1/0.28 | 90/85 |
| Comp. 8 | X3/0.2 A1/10 | B1-21/0.9 | I-1/0.2 | D1/0.28 | 90/85 |
| Comp. 9 | X3/0.2 A2/10 | B1-21/0.9 | I-1/0.2 | D1/0.28 | 90/85 |
| Comp. 10 | X3/0.2 A2/10 | B1-22/0.5 | I-2/0.3 | D1/0.28 | 90/85 |
| Comp. 11 | X3/0.2 A2/10 | B1-22/0.5 | I-3/0.3 | D1/0.28 | 90/85 |
| Comp. 12 | X3/0.2 A2/10 | B1-21/0.9 | I-65/0.2 | D1/0.28 | 90/85 |
| Comp. 13 | X3/0.2 A2/10 | B1-21/0.9 | I-81/0.2 | D1/0.28 | 90/85 |
| Compar. Comp. 1 | A1/10 X1/0.2 | None | B1-X/0.6 | D1/0.28 | 90/85 |

In Table 4, symbols represent the following components.
<Resin>
A1: Resin A1, A2: Resin A2,
X1: Resin X1, X2: Resin X2, X3: Resin X3
<Salt (I)>
I-1: Salt represented by formula (I-1)
I-2: Salt represented by formula (I-2)
I-3: Salt represented by formula (I-3)
I-65: Salt represented by formula (I-65)
I-81: Salt represented by formula (I-81)
<Salt (B1)>
B1-21: Salt represented by formula (B1-21)
B1-22: Salt represented by formula (B1-22)

B1-X: Salt represented by the following formula, produced according to JP2011-16794A1.

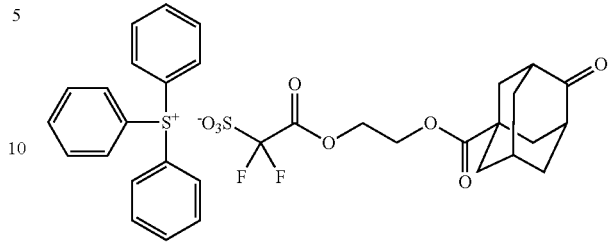

<Quencher>
D1: The compound of the following formula, which was manufactured by Tokyo Chemical Industries, Co., Ltd.

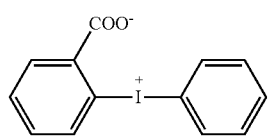

<Solvent>

| E1: Mixture of the following ones | |
|---|---|
| propyleneglycolmonomethylether acetate | 265 parts |
| propyleneglycolmonomethylether | 20 parts |
| 2-heptanone | 20 parts |
| γ-butyrolactone | 3.5 parts |

<Evaluation>

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating.

One of the photo resist compositions prepared as above was spin-coated over the anti-reflective coating so that the thickness of the resulting film became 85 nm after drying.

The silicon wafer thus coated with the photoresist composition was prebaked on a direct hotplate at a temperature shown in the column "PB" in Table 4 for 60 seconds.

Using an ArF excimer stepper for immersion exposure ("XT: 1900Gi" manufactured by ASML, NA=1.35, ¾ Annular, XY-pol.) and a mask for preparing a contact hole pattern (pitch: 90 nm, hole diameter: 55 nm), the wafer thus formed with the composition film was subjected to the exposure with the exposure quantity being varied stepwise.

Ultrapure water was used for immersion solvent. After the exposure, the wafer was subjected to post-exposure baking on a hotplate at a temperature shown in the column "PEB" in Table 4 for 60 seconds and then to conduct development in the manner of dynamic dispense method for 20 seconds at 23° C. with butyl acetate, product of Tokyo Chemical Industry, Co., Ltd to thereby obtain a negative type photoresist pattern.

Effective sensitivity (ES): It was defined as the exposure quantity that the hole diameter of the pattern became 50 nm after exposure and development.

(Critical Dimension Uniformity (CDU) Evaluation)

The photoresist patterns were formed in the same manner as described above with the exposure at the effective sensitivity, using a mask having 55 nm of the hole diameter. The hole diameter of each hole was measured at 24 points, and the average of those measured values was determined as the average hole diameter of the hole. The standard deviation of the average hole diameter was obtained taking, as its population, the above average hole diameters of 400 holes within the same wafer.

Table 5 illustrates the results thereof. In the table, the result that the value of the standard deviation was less than 1.85 nm was evaluated as excellent and represented by "oo";

the result that the value was 1.85 nm or more and less than 2.00 nm was evaluated as very good and represented by "o", and the result that the value was 2.00 nm or more was evaluated as bad and represented by "x".

TABLE 5

| Ex. No. | Composition | CDU(nm) |
|---|---|---|
| Ex. 6 | Comp. 1 | oo (1.81) |
| Ex. 7 | Comp. 2 | o (1.90) |
| Test Ex. 1 | Comp. 3 | o (1.87) |
| Ex. 8 | Comp. 4 | oo (1.79) |
| Ex. 9 | Comp. 5 | o (1.88) |
| Test Ex. 2 | Comp. 6 | o (1.86) |
| Ex. 10 | Comp. 7 | oo (1.73) |
| Ex. 11 | Comp. 8 | oo (1.68) |
| Ex. 12 | Comp. 9 | oo (1.62) |
| Ex. 13 | Comp. 10 | oo (1.63) |
| Ex. 14 | Comp. 11 | oo (1.59) |
| Ex. 15 | Comp. 12 | o (1.88) |
| Ex. 16 | Comp. 13 | oo (1.58) |
| Comparative Ex. 1 | Compar. Comp. 1 | x (2.01) |

The salt of the disclosure is suitable for an acid generator, and the photoresist compositions of the disclosure provide a good photoresist pattern with better critical dimension uniformity. Therefore, the photoresist composition is suitable for processing semiconductors.

What is claimed is:

1. A photoresist composition comprising
a resin having an acid-labile group;
a salt represented by the formula (I); and
a salt represented by the formula (B1):

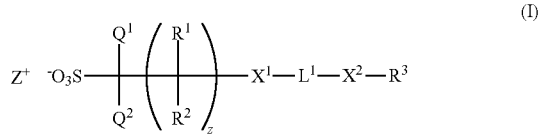
(I)

wherein $Q^1$ and $Q^2$ each independently represent a fluorine atom or a C1 to C6 perfluoroalkyl group;
$R^1$ and $R^2$ each independently represent a hydrogen atom, a fluorine atom or a C1 to C6 perfluoroalkyl group;
"z" represents an integer of 0 to 6;
$X^1$ and $X^2$ each independently represent a group having at least one of *—CO—O—, *—O—CO— and *—O— where * represents a binding site to $L^1$;
$L^1$ represents a C1 to C8 fluoroalkanediyl group; and
$R^3$ represents a C5 to C18 alicyclic hydrocarbon group in which a hydrogen atom can be replaced by a hydroxy group and a methylene group can be replaced by an oxygen atom, a sulfonyl group or a carbonyl group, and which alicyclic hydrocarbon group may have a cyclic ketal structure optionally having a fluorine atom; and $Z^+$ represents an organic cation represented by any one of formulae (b2-1) and (b2-2):

(b2-1)

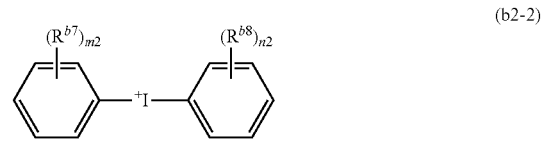
(b2-2)

wherein $R^{b4}$, $R^{b5}$ and $R^{b6}$ independently represent a C1 to C30 aliphatic hydrocarbon group in which a hydrogen atom can be replaced by a hydroxy group, a C1 to C12 alkoxy group, a C3 to C12 alicyclic hydrocarbon group, or a C6 to C18 aromatic hydrocarbon group,
a C3 to C36 alicyclic hydrocarbon group in which a hydrogen atom can be replaced by a halogen atom, a C2 to C4 acyl group or a glycidyloxy group, or
a C6 to C36 aromatic hydrocarbon group in which a hydrogen atom can be replaced by a halogen atom, a hydroxy group, or a C1 to C12 alkoxy group, and $R^{b4}$ and $R^{b5}$ each independently represent a ring together with $S^+$,
$R^{b7}$ and $R^{b8}$ each independently represent a hydroxy group, a C1 to C12 alkyl group or a C1 to C12 alkoxy group, and
m2 and n2 each independently represent an integer of 0 to 5;

(B1)

wherein $Q^{21b}$ and $Q^{22b}$ each independently represent a fluorine atom or a C1 to C6 perfluoroalkyl group,
$L^{b21}$ represents a single bond or a C1 to C24 divalent saturated hydrocarbon group where a methylene group can be replaced by an oxygen atom or a carbonyl group and where a hydrogen atom can be replaced by a hydroxy group,
$Y^{21}$ represents a C3 to C18 alicyclic hydrocarbon group where a methylene group can be replaced by an oxygen atom or a carbonyl group and where a hydrogen atom can be replaced by a hydroxyl group or a fluorine atom, and
$Zb^+$ represents an organic cation represented by any one of the formula (b2-1) and the formula (b2-2).

2. The photoresist composition according to claim 1 wherein $X^1$ represents *—CO—O—.

3. The photoresist composition according to claim 1 wherein $X^2$ represents *—CO—O—.

4. The photoresist composition according to claim 1 wherein $X^1$ represents —$CH_2$—$(CF_2)_n$—$CH_2$— where n represents integer of 1 to 6.

5. The photoresist composition according to claim 1 wherein the alicyclic hydrocarbon group for $R^3$ is an adamantyl group.

6. The photoresist composition according to claim 1 wherein $L^{b21}$ L represents a group represented by formula (b1-4):

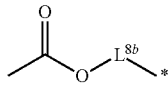

(b1-4)

wherein $L^{b8}$ represents a single bond or a $C_1$ to $C_{22}$ divalent saturated hydrocarbon group where a hydrogen atom can be replaced by a hydroxy group, and * represents a binding site to $Y^{21}$.

7. The photoresist composition according to claim 1, which further comprises a salt which generates an acid weaker in acidity than an acid generated from the salt represented by the formula (B1) and an acid generated from the salt represented by the formula (I).

8. A salt represented by the formula (Ia):

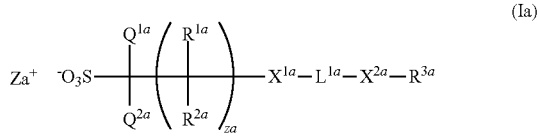

(Ia)

wherein $Q^{1a}$ and $Q^{2a}$ each independently represent a fluorine atom or a C1 to C6 perfluoroalkyl group;

$R^{1a}$ and $R^{2a}$ each independently represent a hydrogen atom, a fluorine atom or a C1 to C6 perfluoroalkyl group;

"za" represents an integer of 0 to 6;

$X^{1a}$ and $X^{2a}$ each independently represent a group having at least one of *—CO—O—, *—O—CO— and *—O— group where * represents a binding site to $L^{1a}$, provided that at least one of $X^{1a}$ and $X^{2a}$ represents *—CO—O— or *—O—CO—;

$L^{1a}$ represents —$CH_2$—$(CF_2)_{na}$—$CH_2$— where "na" represents an integer of 2 to 6;

$R^{3a}$ represents a C5 to C18 alicyclic hydrocarbon group in which a hydrogen atom can be replaced by a hydroxy group and a methylene group can be replaced by an oxygen atom, a sulfonyl group or a carbonyl group, and which alicyclic hydrocarbon group may have a cyclic ketal structure optionally having a fluorine atom; and $Za^+$ represents an organic cation.

9. The salt according to claim 8 wherein $X^{1a}$ represents *—CO—O—.

10. The salt according to claim 8 wherein $X^{2a}$ represents *—O—CO—.

11. The salt according to claim 8 wherein the alicyclic hydrocarbon group for $R^{3a}$ is an adamantyl group.

12. A photoresist composition which comprises the salt according to claim 8 and a resin having an acid-labile group.

13. A process for producing a photoresist pattern comprising the following steps (1) to (5):
(1) a step of applying the photoresist composition according to claim 1 on a substrate,
(2) a step of forming a composition film by conducting drying,
(3) a step of exposing the composition film to radiation,
(4) a step of baking the exposed composition film, and
(5) a step of developing the baked composition film.

* * * * *